United States Patent
Ashby et al.

(10) Patent No.: US 9,028,368 B2
(45) Date of Patent: *May 12, 2015

(54) SYSTEMS, METHODS, AND DEVICES FOR SIMULATING REAL WORLD TERRAIN ON AN EXERCISE DEVICE

(75) Inventors: Darren C. Ashby, Richmond, UT (US); Scott R. Watterson, Logan, UT (US); Kirk Lorrigan, Millville, UT (US); William T. Dalebout, Logan, UT (US)

(73) Assignee: ICON Health & Fitness, Inc., Logan, UT (US)

(*) Notice: Subject to any disclaimer, the term of this patent is extended or adjusted under 35 U.S.C. 154(b) by 126 days.

This patent is subject to a terminal disclaimer.

(21) Appl. No.: 13/176,510

(22) Filed: Jul. 5, 2011

(65) Prior Publication Data

US 2012/0220427 A1 Aug. 30, 2012

Related U.S. Application Data

(60) Continuation of application No. 12/413,362, filed on Mar. 27, 2009, now Pat. No. 8,029,415, which is a continuation-in-part of application No. 11/849,068, filed on Aug. 31, 2007, now abandoned, which is a (Continued)

(51) Int. Cl.
*A63B 15/02* (2006.01)
*A63B 24/00* (2006.01)
(Continued)

(52) U.S. Cl.
CPC ........... *A63B 24/0075* (2013.01); *A63B 21/015* (2013.01); *A63B 21/225* (2013.01);
(Continued)

(58) Field of Classification Search
CPC ........... A63B 22/0023; A63B 22/0605; A63B 24/0075; A63B 71/0622; A63B 2024/009; A63B 2220/70; A63B 2220/73; A63B 2071/0636; A63B 2071/0638; A63B 2071/0644; A63B 2071/0691
USPC .......... 482/1–9, 51, 57–65, 900–902
See application file for complete search history.

(56) References Cited

U.S. PATENT DOCUMENTS

D211,801 S 7/1968 Quinton
3,408,067 A 10/1968 Armstrong
(Continued)

FOREIGN PATENT DOCUMENTS

CN 1162495 A 10/1997
CN 2449755 Y 9/2001
(Continued)

OTHER PUBLICATIONS

Trackmaster Online http://web.archive.org./web/19991012091810/ http://www.trackmastertreadmills.com available on information and belief at least as early as Oct. 1999.
(Continued)

*Primary Examiner* — Stephen Crow
*Assistant Examiner* — Gregory Winter
(74) *Attorney, Agent, or Firm* — Workman Nydegger

(57) ABSTRACT

An exercise system includes one or more exercise devices that communicate via a network with a communication system. The communication system stores and/or generates exercise programming for use on the exercise device. The exercise programming is able to control one or more operating parameters of the exercise device to simulate terrain found at a remote, real world location. The exercise programming can include images/videos of the remote, real world location. The control signals and the images/videos can be synchronized so that a user of the exercise device is able to experience, via the changing operating parameters, the topographical characteristics of the remote, real world location as well as see images of the location.

19 Claims, 14 Drawing Sheets

Related U.S. Application Data continuation-in-part of application No. 10/916,687, filed on Aug. 11, 2004, now Pat. No. 7,628,737, and a continuation-in-part of application No. 11/315,682, filed on Dec. 21, 2005, now Pat. No. 7,985,164, which is a continuation-in-part of application No. 10/856,676, filed on May 28, 2004, now Pat. No. 7,628,730, which is a continuation-in-part of application No. 09/776,410, filed on Feb. 2, 2001, now Pat. No. 6,997,852, which is a continuation-in-part of application No. 09/641,220, filed on Aug. 18, 2000, now Pat. No. 6,458,060, and a continuation-in-part of application No. 09/641,600, filed on Aug. 18, 2000, now Pat. No. 7,060,006, and a continuation-in-part of application No. 09/641,627, filed on Aug. 18, 2000, now Pat. No. 7,166,062, said application No. 09/641,220 is a continuation-in-part of application No. 09/496,560, filed on Feb. 2, 2000, now Pat. No. 6,447,424, said application No. 09/641,627 is a continuation-in-part of application No. 09/496,560, filed on Feb. 2, 2000, now Pat. No. 6,447,424, said application No. 09/641,220 is a continuation-in-part of application No. 09/349,608, filed on Jul. 8, 1999, now Pat. No. 6,312,363, and a continuation-in-part of application No. 09/496,560, filed on Feb. 2, 2000, now Pat. No. 6,447,424, said application No. 12/413,362 is a continuation-in-part of application No. 11/429,725, filed on May 8, 2006, now Pat. No. 7,556,590, which is a division of application No. 09/947,193, filed on Sep. 5, 2001, now Pat. No. 7,166,064, which is a continuation-in-part of application No. 09/641,600, filed on Aug. 18, 2000, now Pat. No. 7,060,006, and a continuation-in-part of application No. 09/641,220, filed on Aug. 18, 2000, now Pat. No. 6,458,060, and a continuation-in-part of application No. 09/641,627, filed on Aug. 18, 2000, now Pat. No. 7,166,062, said application No. 09/641,600 is a continuation-in-part of application No. 09/496,560, filed on Feb. 2, 2000, now Pat. No. 6,447,424, said application No. 09/641,220 is a continuation-in-part of application No. 09/496,560, filed on Feb. 2, 2000, now Pat. No. 6,447,424, said application No. 09/641,627 is a continuation-in-part of application No. 09/496,560, filed on Feb. 2, 2000, now Pat. No. 6,447,424, said application No. 09/641,600 is a continuation-in-part of application No. 09/349,608, filed on Jul. 8, 1999, now Pat. No. 6,312,363, said application No. 09/641,220 is a continuation-in-part of application No. 09/349,608, filed on Jul. 8, 1999, now Pat. No. 6,312,363, said application No. 09/641,627 is a continuation-in-part of application No. 09/349,608, filed on Jul. 8, 1999, now Pat. No. 6,312,363, said application No. 12/413,362 is a continuation-in-part of application No. 10/674,911, filed on Sep. 29, 2003, now Pat. No. 7,537,546, which is a continuation-in-part of application No. 09/933,701, filed on Aug. 20, 2001, now Pat. No. 6,626,799, which is a continuation of application No. 09/349,608, filed on Jul. 8, 1999, now Pat. No. 6,312,363, said application No. 10/674,911 is a continuation-in-part of application No. 09/641,627, filed on Aug. 18, 2000, now Pat. No. 7,166,062, which is a continuation-in-part of application No. 09/349,608, filed on Jul. 8, 1999, now Pat. No. 6,312,363, and a continuation-in-part of application No. 09/496,560, filed on Feb. 2, 2000, now Pat. No. 6,447,424.

(60) Provisional application No. 60/918,250, filed on Mar. 14, 2007.

(51) Int. Cl.
A63B 71/00 (2006.01)
A63B 22/00 (2006.01)
A63B 22/02 (2006.01)
A63B 71/06 (2006.01)
A63B 22/06 (2006.01)
A63B 21/015 (2006.01)
A63B 21/22 (2006.01)

(52) U.S. Cl.
CPC ............. *A63B22/0023* (2013.01); *A63B 22/02* (2013.01); *A63B 22/0235* (2013.01); *A63B 24/0087* (2013.01); *A63B 71/0622* (2013.01); *A63B 2024/009* (2013.01); *A63B 2071/063* (2013.01); *A63B 2071/0691* (2013.01); *A63B 2220/17* (2013.01); *A63B 2220/70* (2013.01); *A63B 2220/73* (2013.01); *A63B 2220/78* (2013.01); *A63B 22/0605* (2013.01)

(56) References Cited

U.S. PATENT DOCUMENTS

| | | | |
|---|---|---|---|
| 3,518,985 A | | 7/1970 | Quinton |
| 3,592,466 A | | 7/1971 | Parsons |
| 3,602,502 A | | 8/1971 | Hampl |
| 3,659,845 A | | 5/1972 | Quinton |
| 3,744,712 A | | 7/1973 | Papadopoulos et al. |
| 3,802,698 A | | 4/1974 | Burian et al. |
| 3,845,756 A | | 11/1974 | Olsson |
| 3,903,613 A | | 9/1975 | Bisberg |
| 4,020,795 A | | 5/1977 | Marks |
| 4,082,267 A | | 4/1978 | Flavell |
| 4,112,928 A | | 9/1978 | Putsch |
| 4,120,294 A | | 10/1978 | Wolfe |
| 4,151,988 A | | 5/1979 | Nabinger |
| 4,220,996 A | | 9/1980 | Searcy |
| 4,278,095 A | | 7/1981 | Lapeyre |
| 4,358,105 A | | 11/1982 | Sweeney, Jr. |
| 4,408,613 A | | 10/1983 | Relyea |
| 4,423,864 A | | 1/1984 | Wiik |
| 4,504,055 A | | 3/1985 | Wells |
| 4,542,897 A | | 9/1985 | Melton et al. |
| 4,544,152 A | | 10/1985 | Taitel |
| 4,549,044 A | | 10/1985 | Durham |
| 4,556,216 A | | 12/1985 | Pitkanen |
| 4,571,682 A | | 2/1986 | Silverman et al. |
| 4,586,495 A | | 5/1986 | Petrofsky |
| 4,602,779 A | | 7/1986 | Ogden |
| 4,642,769 A | | 2/1987 | Petrofsky |
| 4,643,418 A | | 2/1987 | Bart |
| 4,659,074 A | | 4/1987 | Taitel et al. |
| 4,659,078 A | | 4/1987 | Blome |
| 4,671,257 A | | 6/1987 | Kaiser et al. |
| 4,687,195 A | | 8/1987 | Potts |
| 4,702,475 A | | 10/1987 | Elstein et al. |
| 4,708,337 A | | 11/1987 | Shyu |
| 4,708,837 A | | 11/1987 | Baxter et al. |
| 4,709,917 A | | 12/1987 | Yang |
| 4,750,738 A | | 6/1988 | Dang |
| 4,757,495 A | | 7/1988 | Decker et al. |
| 4,759,540 A | | 7/1988 | Yu et al. |
| 4,763,284 A | | 8/1988 | Carlin |
| 4,765,613 A | | 8/1988 | Voris |
| 4,786,049 A | * | 11/1988 | Lautenschlager ................ 482/9 |
| 4,790,528 A | | 12/1988 | Nakao et al. |
| 4,818,234 A | | 4/1989 | Redington et al. |
| 4,828,257 A | | 5/1989 | Dyer et al. |
| 4,837,157 A | | 6/1989 | Turnell et al. |
| 4,842,266 A | | 6/1989 | Sweeney, Sr. et al. |
| 4,842,274 A | | 6/1989 | Oosthuizen et al. |
| 4,848,737 A | | 7/1989 | Ehrenfield |
| 4,860,763 A | | 8/1989 | Schminke |
| 4,866,704 A | | 9/1989 | Bergman |
| 4,867,442 A | | 9/1989 | Matthews |
| 4,869,497 A | | 9/1989 | Stewart et al. |

(56) References Cited

U.S. PATENT DOCUMENTS

| | | |
|---|---|---|
| 4,889,108 A | 12/1989 | Bond et al. |
| 4,907,795 A | 3/1990 | Shaw et al. |
| 4,919,418 A | 4/1990 | Miller |
| 4,925,183 A | 5/1990 | Kim |
| 4,925,189 A | 5/1990 | Braeunig |
| 4,927,136 A | 5/1990 | Leask |
| 4,934,694 A | 6/1990 | McIntosh |
| 4,938,474 A | 7/1990 | Sweeney et al. |
| 4,949,993 A | 8/1990 | Stark et al. |
| 4,959,713 A | 9/1990 | Morotomi et al. |
| 4,976,435 A | 12/1990 | Shatford et al. |
| 4,998,725 A | 3/1991 | Watterson et al. |
| 5,020,795 A | 6/1991 | Airy et al. |
| 5,035,418 A | 7/1991 | Harabayashi |
| 5,037,089 A | 8/1991 | Spagnuolo et al. |
| 5,054,774 A | 10/1991 | Belsito |
| 5,062,632 A | 11/1991 | Dalebout et al. |
| 5,067,710 A | 11/1991 | Watterson et al. |
| 5,078,152 A | 1/1992 | Bond et al. |
| 5,086,385 A | 2/1992 | Launey et al. |
| 5,088,729 A | 2/1992 | Dalebout |
| 5,089,960 A | 2/1992 | Sweeney, Jr. |
| 5,104,120 A | 4/1992 | Watterson et al. |
| 5,113,427 A | 5/1992 | Ryoichi et al. |
| 5,137,501 A | 8/1992 | Mertesdorf |
| 5,142,358 A | 8/1992 | Jason |
| 5,145,475 A | 9/1992 | Cares |
| 5,149,084 A | 9/1992 | Dalebout et al. |
| 5,180,347 A | 1/1993 | Chen |
| 5,195,935 A | 3/1993 | Fencel |
| 5,201,772 A | 4/1993 | Maxwell |
| 5,213,555 A | 5/1993 | Hood et al. |
| 5,230,673 A | 7/1993 | Maeyama et al. |
| 5,240,417 A | 8/1993 | Smithson et al. |
| 5,243,998 A | 9/1993 | Silverman et al. |
| 5,254,066 A | 10/1993 | Brown et al. |
| 5,256,115 A | 10/1993 | Scholder et al. |
| 5,277,678 A | 1/1994 | Friedebach et al. |
| 5,290,205 A | 3/1994 | Densmore et al. |
| 5,292,293 A | 3/1994 | Schumacher |
| 5,299,810 A | 4/1994 | Pierce et al. |
| 5,308,296 A | 5/1994 | Eckstein |
| 5,308,300 A | 5/1994 | Chino et al. |
| 5,313,942 A | 5/1994 | Platzker |
| 5,314,389 A | 5/1994 | Dotan |
| 5,314,391 A | 5/1994 | Potash et al. |
| 5,316,534 A | 5/1994 | Dalebout et al. |
| 5,318,487 A | 6/1994 | Golen et al. |
| 5,318,491 A | 6/1994 | Houston |
| 5,323,784 A | 6/1994 | Shu |
| D348,493 S | 7/1994 | Ashby |
| 5,328,420 A | 7/1994 | Allen |
| 5,328,422 A | 7/1994 | Nichols |
| 5,335,188 A | 8/1994 | Brisson |
| 5,352,166 A | 10/1994 | Chang |
| 5,361,091 A | 11/1994 | Hoarty et al. |
| 5,375,068 A | 12/1994 | Palmer et al. |
| 5,382,207 A | 1/1995 | Skowronski et al. |
| 5,382,209 A | 1/1995 | Pasier et al. |
| 5,385,519 A | 1/1995 | Hsu et al. |
| 5,385,520 A | 1/1995 | Lepine et al. |
| 5,387,164 A | 2/1995 | Brown, Jr. |
| 5,391,080 A | 2/1995 | Bernacki et al. |
| 5,403,252 A | 4/1995 | Leon et al. |
| 5,407,402 A | 4/1995 | Brown et al. |
| 5,410,471 A | 4/1995 | Alyfuku et al. |
| 5,410,472 A | 4/1995 | Anderson |
| 5,417,222 A | 5/1995 | Dempsey et al. |
| 5,431,612 A | 7/1995 | Holden |
| 5,433,679 A | 7/1995 | Szymczak et al. |
| 5,435,799 A | 7/1995 | Lundin |
| 5,451,922 A | 9/1995 | Hamilton |
| 5,462,051 A | 10/1995 | Oka et al. |
| 5,462,503 A | 10/1995 | Benjamin et al. |
| 5,462,504 A | 10/1995 | Trulaske et al. |
| 5,466,200 A | 11/1995 | Ulrich et al. |
| 5,474,090 A | 12/1995 | Begun et al. |
| 5,476,430 A | 12/1995 | Lee et al. |
| 5,484,389 A | 1/1996 | Stark et al. |
| 5,489,249 A | 2/1996 | Brewer et al. |
| 5,489,250 A | 2/1996 | Densmore et al. |
| 5,512,025 A | 4/1996 | Dalebout et al. |
| 5,518,471 A | 5/1996 | Hettinger et al. |
| 5,527,239 A | 6/1996 | Abbondanza |
| 5,527,245 A | 6/1996 | Dalebout et al. |
| 5,535,664 A | 7/1996 | Rokowski |
| 5,538,486 A | 7/1996 | France et al. |
| 5,545,112 A | 8/1996 | Densmore et al. |
| 5,546,324 A | 8/1996 | Palmer et al. |
| 5,547,439 A | 8/1996 | Rawls et al. |
| 5,572,643 A | 11/1996 | Judson |
| 5,577,981 A | 11/1996 | Jarvik |
| 5,584,779 A | 12/1996 | Knecht et al. |
| 5,590,128 A | 12/1996 | Maloney et al. |
| 5,591,104 A | 1/1997 | Andrus et al. |
| 5,598,849 A | 2/1997 | Browne |
| 5,600,310 A | 2/1997 | Whipple, III et al. |
| 5,605,336 A | 2/1997 | Gaoiran et al. |
| 5,619,412 A | 4/1997 | Hapka |
| 5,619,991 A | 4/1997 | Sloane |
| 5,626,539 A | 5/1997 | Piaget et al. |
| 5,645,509 A | 7/1997 | Brewer et al. |
| 5,645,513 A | 7/1997 | Haydocy et al. |
| 5,655,997 A | 8/1997 | Greenberg et al. |
| 5,663,951 A | 9/1997 | Danneels et al. |
| 5,667,459 A | 9/1997 | Su |
| 5,674,453 A | 10/1997 | Watterson et al. |
| 5,676,138 A | 10/1997 | Zawilinski |
| 5,690,582 A | 11/1997 | Ulrich et al. |
| 5,695,400 A | 12/1997 | Fennell, Jr. et al. |
| 5,697,834 A | 12/1997 | Heumann et al. |
| 5,702,323 A | 12/1997 | Poulton |
| 5,704,875 A | 1/1998 | Tanabe |
| 5,713,794 A | 2/1998 | Shimojima et al. |
| 5,719,825 A | 2/1998 | Dotter |
| 5,720,771 A | 2/1998 | Snell |
| 5,721,539 A | 2/1998 | Goetzl |
| 5,722,418 A | 3/1998 | Bro |
| 5,733,228 A | 3/1998 | Stevens |
| 5,738,612 A | 4/1998 | Tsuda |
| 5,741,205 A | 4/1998 | Doll et al. |
| 5,743,833 A | 4/1998 | Watterson et al. |
| 5,749,372 A | 5/1998 | Allen |
| 5,752,883 A | 5/1998 | Butcher |
| 5,752,897 A | 5/1998 | Skowronski |
| 5,754,765 A | 5/1998 | Danneels |
| 5,759,199 A | 6/1998 | Snell |
| 5,771,354 A | 6/1998 | Crawford |
| 5,777,678 A | 7/1998 | Ogata et al. |
| 5,779,596 A | 7/1998 | Weber |
| 5,782,639 A | 7/1998 | Beal |
| 5,785,630 A | 7/1998 | Bobick et al. |
| 5,785,631 A | 7/1998 | Heidecke |
| 5,810,696 A | 9/1998 | Webb |
| 5,810,747 A | 9/1998 | Brudny et al. |
| 5,813,864 A | 9/1998 | Ikuta |
| 5,820,525 A | 10/1998 | Riley |
| 5,827,155 A | 10/1998 | Jensen et al. |
| 5,830,113 A | 11/1998 | Coody |
| 5,833,577 A | 11/1998 | Hurt |
| 5,836,770 A | 11/1998 | Powers |
| 5,838,906 A | 11/1998 | Doyle |
| 5,845,230 A | 12/1998 | Lamberson |
| 5,854,833 A | 12/1998 | Hogan |
| 5,855,537 A | 1/1999 | Coody |
| 5,857,939 A | 1/1999 | Kaufman |
| 5,860,893 A | 1/1999 | Watterson et al. |
| 5,860,894 A | 1/1999 | Dalebout et al. |
| 5,865,733 A | 2/1999 | Malinouskas |
| 5,868,648 A | 2/1999 | Coody |
| 5,873,369 A | 2/1999 | Lanaido et al. |
| 5,879,270 A | 3/1999 | Huish |
| 5,880,677 A | 3/1999 | Lestician |
| 5,888,172 A | 3/1999 | Andrus et al. |

(56) References Cited

U.S. PATENT DOCUMENTS

| | | | |
|---|---|---|---|
| 5,890,906 A | 4/1999 | Macri |
| 5,890,995 A | 4/1999 | Bobick et al. |
| 5,890,997 A | 4/1999 | Roth |
| 5,891,042 A | 4/1999 | Sham et al. |
| 5,899,834 A | 5/1999 | Dalebout et al. |
| 5,905,442 A | 5/1999 | Mosebrook et al. |
| 5,906,581 A | 5/1999 | Tsuda |
| 5,909,544 A | 6/1999 | Anderson, II et al. |
| 5,910,070 A | 6/1999 | Henry et al. |
| 5,911,132 A | 6/1999 | Sloane |
| 5,911,687 A | 6/1999 | Sato et al. |
| 5,916,063 A | 6/1999 | Alessandri |
| 5,917,405 A | 6/1999 | Joao |
| 5,929,748 A | 7/1999 | Odinak |
| 5,929,782 A | 7/1999 | Stark |
| 5,931,763 A | 8/1999 | Alessandri |
| 5,947,869 A | 9/1999 | Shea |
| 5,947,872 A | 9/1999 | Ryan et al. |
| 5,956,509 A | 9/1999 | Kevner |
| 5,961,561 A | 10/1999 | Wakefield, II |
| 5,964,701 A | 10/1999 | Asada et al. |
| 5,967,975 A | 10/1999 | Ridgeway |
| 5,993,356 A | 11/1999 | Houston et al. |
| 5,995,868 A | 11/1999 | Dorfmeister et al. |
| 5,997,476 A | 12/1999 | Brown |
| 6,004,243 A | 12/1999 | Ewert |
| 6,010,451 A | 1/2000 | Clawson |
| 6,013,007 A | 1/2000 | Root et al. |
| 6,013,011 A | 1/2000 | Moore et al. |
| 6,014,432 A | 1/2000 | Modney |
| 6,022,272 A | 2/2000 | Sano |
| 6,027,429 A | 2/2000 | Daniels |
| 6,033,344 A | 3/2000 | Trulaske et al. |
| 6,033,347 A | 3/2000 | Dalebout et al. |
| 6,042,519 A | 3/2000 | Shea |
| 6,045,490 A | 4/2000 | Shafer et al. |
| 6,050,822 A | 4/2000 | Faughn |
| 6,050,921 A | 4/2000 | Wang |
| 6,050,923 A | 4/2000 | Yu |
| 6,050,924 A | 4/2000 | Shea |
| 6,050,942 A | 4/2000 | Rust |
| 6,053,737 A | 4/2000 | Babbit et al. |
| 6,053,844 A | 4/2000 | Clem |
| 6,056,670 A | 5/2000 | Shu et al. |
| 6,059,692 A | 5/2000 | Hickman |
| 6,066,075 A | 5/2000 | Poulton |
| 6,066,705 A | 5/2000 | Calderon |
| 6,068,578 A | 5/2000 | Wang |
| 6,103,203 A | 8/2000 | Fisher |
| 6,106,297 A | 8/2000 | Pollak et al. |
| 6,110,076 A | 8/2000 | Hurt |
| 6,126,577 A | 10/2000 | Chang |
| 6,132,337 A | 10/2000 | Krupka et al. |
| 6,132,340 A | 10/2000 | Wang et al. |
| 6,142,913 A * | 11/2000 | Ewert ............................... 482/8 |
| 6,148,262 A | 11/2000 | Fry |
| 6,152,854 A | 11/2000 | Carmein |
| 6,152,856 A * | 11/2000 | Studor et al. ..................... 482/8 |
| 6,162,151 A | 12/2000 | Tani et al. |
| 6,162,189 A | 12/2000 | Girone |
| 6,171,186 B1 | 1/2001 | Kurosawa et al. |
| 6,171,218 B1 | 1/2001 | Shea |
| 6,174,268 B1 | 1/2001 | Novak |
| 6,175,608 B1 | 1/2001 | Pyles et al. |
| 6,179,753 B1 | 1/2001 | Barker et al. |
| 6,193,631 B1 | 2/2001 | Hickman |
| 6,198,394 B1 | 3/2001 | Jacobsen et al. |
| 6,211,451 B1 | 4/2001 | Tohgi et al. |
| 6,231,481 B1 | 5/2001 | Brock |
| 6,231,482 B1 | 5/2001 | Thompson |
| 6,234,936 B1 | 5/2001 | Wang |
| 6,241,524 B1 | 6/2001 | Aoshima et al. |
| 6,244,987 B1 | 6/2001 | Ohsuga et al. |
| 6,244,988 B1 | 6/2001 | Delman |
| 6,251,048 B1 | 6/2001 | Kaufman |
| 6,259,944 B1 | 7/2001 | Margulis et al. |
| 6,280,362 B1 | 8/2001 | Dalebout et al. |
| 6,283,896 B1 | 9/2001 | Grunfeld et al. |
| 6,287,239 B1 | 9/2001 | Hernandez |
| 6,292,688 B1 | 9/2001 | Patton |
| 6,312,363 B1 | 11/2001 | Watterson et al. |
| 6,322,451 B1 | 11/2001 | Miura |
| 6,336,891 B1 | 1/2002 | Fedrigon et al. |
| 6,342,028 B1 | 1/2002 | De Sane |
| 6,356,856 B1 | 3/2002 | Damen et al. |
| 6,358,187 B1 | 3/2002 | Smith |
| 6,371,850 B1 | 4/2002 | Sonoda |
| 6,402,558 B1 | 6/2002 | Hung-Ju et al. |
| 6,447,424 B1 | 9/2002 | Ashby et al. |
| 6,450,922 B1 | 9/2002 | Henderson |
| 6,458,060 B1 | 10/2002 | Watterson et al. |
| 6,458,061 B2 | 10/2002 | Simonson |
| 6,463,385 B1 | 10/2002 | Fry |
| 6,464,618 B1 | 10/2002 | Shea |
| 6,475,115 B1 | 11/2002 | Candito et al. |
| 6,478,736 B1 | 11/2002 | Mault |
| 6,493,652 B1 | 12/2002 | Ohlenbusch et al. |
| 6,497,638 B1 | 12/2002 | Shea |
| 6,503,173 B2 | 1/2003 | Clem |
| 6,513,532 B2 | 2/2003 | Mault et al. |
| 6,572,512 B2 | 6/2003 | Anderson et al. |
| 6,582,342 B2 | 6/2003 | Kaufman et al. |
| 6,585,622 B1 | 7/2003 | Shum |
| 6,601,016 B1 | 7/2003 | Brown et al. |
| 6,605,020 B1 | 8/2003 | Huang |
| 6,605,038 B1 | 8/2003 | Teller |
| 6,612,492 B1 | 9/2003 | Yen |
| 6,616,578 B2 | 9/2003 | Alessandri |
| 6,626,799 B2 | 9/2003 | Watterson et al. |
| 6,626,803 B1 | 9/2003 | Oglesby et al. |
| 6,634,992 B1 | 10/2003 | Ogawa |
| 6,638,198 B1 | 10/2003 | Shea |
| 6,645,124 B1 | 11/2003 | Clem |
| 6,645,125 B1 | 11/2003 | Stearns et al. |
| 6,648,798 B2 | 11/2003 | Yoo |
| 6,648,802 B2 | 11/2003 | Ware |
| 6,659,916 B1 | 12/2003 | Shea |
| 6,659,946 B1 | 12/2003 | Batchelor et al. |
| 6,669,600 B2 | 12/2003 | Warner |
| 6,685,607 B1 | 2/2004 | Olson |
| 6,687,535 B2 | 2/2004 | Hautala et al. |
| 6,689,057 B1 | 2/2004 | Shinsel et al. |
| 6,700,788 B2 | 3/2004 | Matsushita et al. |
| 6,701,271 B2 | 3/2004 | Willner et al. |
| 6,702,719 B1 | 3/2004 | Brown et al. |
| 6,712,737 B1 | 3/2004 | Nusbaum |
| 6,736,759 B1 | 5/2004 | Stubbs |
| 6,740,007 B2 | 5/2004 | Gordon et al. |
| 6,746,371 B1 | 6/2004 | Brown et al. |
| 6,749,537 B1 | 6/2004 | Hickman |
| 6,761,667 B1 | 7/2004 | Cutler et al. |
| 6,776,740 B1 | 8/2004 | Anderson et al. |
| 6,783,482 B2 | 8/2004 | Oglesby et al. |
| 6,786,848 B2 | 9/2004 | Yamashita et al. |
| 6,790,178 B1 | 9/2004 | Mault et al. |
| 6,793,607 B2 | 9/2004 | Neil |
| 6,808,472 B1 | 10/2004 | Hickman |
| 6,808,473 B2 | 10/2004 | Hisano et al. |
| 6,824,502 B1 | 11/2004 | Huang |
| 6,825,876 B1 | 11/2004 | Easwar et al. |
| 6,863,641 B1 | 3/2005 | Brown et al. |
| 6,866,613 B1 | 3/2005 | Brown et al. |
| 6,918,858 B2 | 7/2005 | Watterson et al. |
| 6,921,351 B1 | 7/2005 | Hickman et al. |
| 6,976,624 B2 | 12/2005 | Hsiao |
| 6,991,586 B2 | 1/2006 | Lapcevic |
| 6,997,852 B2 | 2/2006 | Watterson et al. |
| 7,008,356 B2 | 3/2006 | Hung |
| 7,022,047 B2 | 4/2006 | Cohen et al. |
| 7,044,891 B1 | 5/2006 | Rivera |
| 7,056,265 B1 | 6/2006 | Shea |
| 7,060,006 B1 | 6/2006 | Watterson et al. |
| 7,060,008 B2 | 6/2006 | Watterson et al. |
| 7,070,539 B2 | 7/2006 | Brown et al. |

(56) References Cited

U.S. PATENT DOCUMENTS

| | | | |
|---|---|---|---|
| 7,072,789 B2 | 7/2006 | Vock et al. | |
| 7,115,076 B2 | 10/2006 | Oglesby et al. | |
| 7,128,693 B2 | 10/2006 | Brown et al. | |
| 7,166,062 B1 | 1/2007 | Watterson et al. | |
| 7,166,064 B2 | 1/2007 | Watterson et al. | |
| 7,169,093 B2 | 1/2007 | Simonson et al. | |
| 7,197,029 B1 | 3/2007 | Osterhout et al. | |
| 7,217,224 B2 | 5/2007 | Thomas | |
| 7,254,516 B2 | 8/2007 | Case, Jr. et al. | |
| 7,350,787 B2 | 4/2008 | Voss | |
| 7,354,380 B2 | 4/2008 | Volpe, Jr. | |
| 7,454,002 B1 | 11/2008 | Gardner et al. | |
| 7,455,622 B2 | 11/2008 | Watterson et al. | |
| 7,477,890 B1 | 1/2009 | Narayanaswami | |
| 7,510,509 B2 | 3/2009 | Hickman | |
| 7,537,546 B2 | 5/2009 | Watterson et al. | |
| 7,537,552 B2 | 5/2009 | Dalebout et al. | |
| 7,549,947 B2* | 6/2009 | Hickman et al. | 482/8 |
| 7,556,590 B2 | 7/2009 | Watterson | |
| 7,575,536 B1 | 8/2009 | Hickman | |
| 7,601,097 B2 | 10/2009 | Miyamaru et al. | |
| 7,625,315 B2 | 12/2009 | Hickman | |
| 7,628,730 B1 | 12/2009 | Watterson | |
| 7,628,737 B2 | 12/2009 | Kowallis | |
| 7,637,847 B1 | 12/2009 | Hickman | |
| 7,645,212 B2 | 1/2010 | Ashby | |
| 7,645,213 B2 | 1/2010 | Watterson | |
| 7,682,286 B2 | 3/2010 | Badarneh et al. | |
| 7,689,437 B1 | 3/2010 | Teller et al. | |
| 7,713,171 B1 | 5/2010 | Hickman | |
| 7,717,827 B2* | 5/2010 | Kurunmaki et al. | 482/8 |
| 7,766,798 B2 | 8/2010 | Hamilton | |
| 7,789,800 B1 | 9/2010 | Watterson et al. | |
| 7,798,942 B2 | 9/2010 | Digiulio et al. | |
| 7,811,201 B1* | 10/2010 | Mikan et al. | 482/4 |
| 7,833,129 B2 | 11/2010 | Badarneh et al. | |
| 7,857,731 B2 | 12/2010 | Hickman et al. | |
| 7,862,478 B2 | 1/2011 | Watterson et al. | |
| 7,927,258 B2 | 4/2011 | Irving et al. | |
| 7,963,889 B2 | 6/2011 | Badarneh et al. | |
| 7,980,996 B2 | 7/2011 | Hickman | |
| 7,981,000 B2 | 7/2011 | Watterson et al. | |
| 7,985,164 B2 | 7/2011 | Ashby | |
| 8,029,415 B2 | 10/2011 | Ashby | |
| 8,298,123 B2 | 10/2012 | Hickman | |
| 2001/0028350 A1 | 10/2001 | Matsuoka et al. | |
| 2002/0016235 A1 | 2/2002 | Ashby et al. | |
| 2002/0042328 A1 | 4/2002 | Yoo | |
| 2002/0055422 A1* | 5/2002 | Airmet et al. | 482/61 |
| 2002/0077221 A1 | 6/2002 | Dalebout et al. | |
| 2002/0091796 A1 | 7/2002 | Higginson et al. | |
| 2002/0111541 A1 | 8/2002 | Bible et al. | |
| 2003/0126593 A1 | 7/2003 | Mault | |
| 2003/0148857 A1* | 8/2003 | Yu | 482/57 |
| 2003/0232707 A1 | 12/2003 | Dalebout et al. | |
| 2004/0012335 A1 | 1/2004 | Shon et al. | |
| 2004/0127335 A1 | 7/2004 | Watterson et al. | |
| 2004/0157709 A1 | 8/2004 | Olson | |
| 2004/0162189 A1 | 8/2004 | Hickman | |
| 2005/0026750 A1 | 2/2005 | Oglesby et al. | |
| 2005/0049121 A1 | 3/2005 | Dalebout et al. | |
| 2005/0209052 A1 | 9/2005 | Ashby et al. | |
| 2005/0233859 A1 | 10/2005 | Takai et al. | |
| 2005/0233861 A1 | 10/2005 | Hickman et al. | |
| 2005/0239601 A1 | 10/2005 | Thomas | |
| 2005/0261609 A1 | 11/2005 | Collings et al. | |
| 2005/0272564 A1 | 12/2005 | Pyles et al. | |
| 2005/0272577 A1 | 12/2005 | Olson et al. | |
| 2006/0003872 A1 | 1/2006 | Chiles et al. | |
| 2006/0035768 A1 | 2/2006 | Kowallis et al. | |
| 2006/0063645 A1 | 3/2006 | Chiang | |
| 2006/0122035 A1 | 6/2006 | Felix | |
| 2006/0205566 A1 | 9/2006 | Watterson et al. | |
| 2006/0205569 A1 | 9/2006 | Watterson et al. | |
| 2006/0281603 A1 | 12/2006 | Hickman | |
| 2007/0004565 A1 | 1/2007 | Gebhardt | |
| 2007/0197345 A1* | 8/2007 | Wallace et al. | 482/8 |
| 2007/0265138 A1 | 11/2007 | Ashby | |
| 2008/0051256 A1 | 2/2008 | Ashby et al. | |
| 2008/0097633 A1 | 4/2008 | Jochelson et al. | |
| 2008/0200310 A1* | 8/2008 | Tagliabue | 482/8 |
| 2008/0300110 A1 | 12/2008 | Smith et al. | |
| 2009/0209393 A1* | 8/2009 | Crater et al. | 482/9 |
| 2009/0258758 A1 | 10/2009 | Hickman | |
| 2009/0270226 A1 | 10/2009 | Watterson et al. | |
| 2009/0270227 A1 | 10/2009 | Ashby | |
| 2010/0035726 A1 | 2/2010 | Fisher et al. | |
| 2010/0113222 A1 | 5/2010 | Radow | |
| 2010/0113223 A1 | 5/2010 | Chiles et al. | |
| 2010/0125029 A1* | 5/2010 | Nielson et al. | 482/61 |
| 2010/0179028 A1 | 7/2010 | Watterson et al. | |
| 2010/0248900 A1 | 9/2010 | Ashby et al. | |
| 2011/0071003 A1 | 3/2011 | Watterson et al. | |

FOREIGN PATENT DOCUMENTS

| | | |
|---|---|---|
| DE | 41 00 559 A1 | 7/1991 |
| EP | 0199 442 | 10/1986 |
| EP | 0790034 | 8/1997 |
| EP | 1683550 | 7/2006 |
| JP | H10-243979 | 9/1998 |
| WO | WO 8101507 | 6/1981 |
| WO | WO 8705727 | 9/1987 |
| WO | WO 9107214 | 5/1991 |
| WO | WO 9417860 | 8/1994 |
| WO | WO 9638205 | 12/1996 |
| WO | WO 9800204 | 1/1998 |
| WO | WO 9832496 | 7/1998 |
| WO | WO 9944016 | 2/1999 |
| WO | WO 9930613 | 6/1999 |
| WO | WO 0139089 | 5/2001 |
| WO | WO 2007049077 | 5/2007 |
| WO | WO 2007081607 | 7/2007 |

OTHER PUBLICATIONS

Trackmaster Online: History http://web/archive.org/web/19991012112927/www.trackmaster.com/history.html, available on information and belief at least as early as Oct. 1999, 1 page.

Trackmaster Online: Treadmills http://web.archive.org/web/19991012162015/www.trackmastertreadmills.com/treadmills.html available on information and belief at least as early as Oct. 1999.

Trackmaster Online: Treadmill Controllers: http://web.archive.org/web/20010124093300/www.trackmastertreadmills.com/contrlr.html, available on information and belief at least as early as Oct. 2001, 1 page.

Trackmaster Treadmill Manual, p. 8, "Control Box and Functions."

Trackmaster TM500-E AC Owner's Manual Operation & Maintenance Guide, pp. 1-52, available on information and belief at least as early as Jan. 2001.

Proform Trail Runner Advertisement, copyright 2001 (1 page).

Horizon Fitness Paragon II Owner's Guide, pp. 1-27, available on information and belief at least as early as Aug. 2001.

Horizon Fitness Advance Series Treadmill Owner's Guide, pp. 1-40, available on information and belief at least as early as 2003.

Horizon Fitness Elite 2.0T, Elite 3.0T, Elite 4.0T, Elite 5.0T Treadmill Owner's Guide, pp. 1-40, available on information and belief at least as early as 2004.

Horizon Fitness Horizon T20, Horizon T30, Horizon T40 Treadmill Owner's Guide, pp. 1-40, available on information and belief at least as early as 2004.

Horizon Fitness Alpine Owner's Guide, pp. 1-29, available on information and belief at least as early as Aug. 2001.

Trotter Advertisement: "Introducing the 575 Club Trainer: One Piece of Equipment for Walking, Jogging, Running, and Climbing," available on information and belief at least as early as 1992 (2 pages).

Reebok ACD4 User's Manual, copyright 1998, 34 pages.

Netpulse, Ultra-Wired—Infotech is supposed to make life easier—remember? Here's how to be sure it does., www.netpulse.com, Aug. 1998.

(56) References Cited

OTHER PUBLICATIONS

Trackmaster Online: Treadmills http://web.archive.org/web/20010819045524/www.trackmastertreadmills.com/500.htm, available on information and belief at least as early as Aug. 2001, 2 pages.
Trackmaster Online: Treadmills http://web.archive.org/web/20010819045539/www.trackmastertreadmills.com/500controla.htm, available on information and belief at least as early as Aug. 2001, 2 pages.
Trackmaster Online: Treadmills http://web.archive.org/web/20010815085501/www.trackmastertreadmills.com/treadmills.html, available on information and belief at least as early as Aug. 2001, 2 pages.
Treadmills' Ratings, http://web.archive.org/web/20010505011643/www.treadmillwarehouse.net/rating.htm, available on information and belief at least as early as May 2001, 3 pages.
U.S. Appl. No. 60/152,657, filed Sep. 7, 1999 to James B. Fox et al., entitled Exercise Treadmill (73 pages).
International Search Report and Written Opinion in PCT/US2010/028502 mailed May 21, 2010.
3422 Hall-Effect, Direction-Detection sensor, copyright 2001, 2003, Allegro MicroSystems, Inc., available online at www.allegromicro.com, pp. 1-10.
A3425 Ultra-Sensitive Dual-Channel Quadrature Hall-Effect Bipolar Switch, Copyright 2005, Allegro Microsystems, Inc., available online at www.allegomicro.com, pp. 1-21.
*ICON Health & Fitness, Inc.* v. *Tacx International et al.* (Case No. SACV12-00257 AN): Complaint for Patent Infringement, signed by Tyson K. Hottinger on Feb. 15, 2012.
CNET News: Diamond Faces the Music , Nov. 23, 1998.
CNET News: Surfing at the Gym (C. Macavinta)—news.cnetcom/Surfing-at-the-gym/2100-1023_3-213332.html Jul. 14, 1998.
CNN: Working Out with the Web (E. Knefel)—www.cnn.com/TECH/computing/9805/15/workout/index.html May 15, 1998.
CNN Money: FitLinxx Firms Up Sales (V. Morris)—money.com/1997/01/31/busunu/fitlinxx_pkg/index.htm Jan. 31, 1997.
eCompany Now: Let the Monitoring Begin (Schonfeld)—http://web.archive.org/web/200012011958/http://www.ecompany.com/articles/web/0,1653,8746,00.html Oct. 20, 2000.
FitLinxx Sees Web Site as Health Tonic (B. Dean)—www.dmnews.com/fitlinxx-sees-web-site-ashealth-tonix/article/66598 Jun. 2, 2000.
Forbes: Pumping Software—www.forbes.com/1997/12/19/feat_print.html.
Netpulse Workouts (K. Donnelly)—articles.chicagotribune.com/.../9804280123_1_netpulse-stationsexercise-and-joy-health-clubs Aug. 27, 1998.
The Free Library: 24 Hour Fitness Partners with Netpulse; Members Will Now Get Web Surfing, TV, Music CDs, News Mar. 10, 1998.
Polar Vantage NV User's Manual.
Value Proposition Netpulse: IHRSA Report Sep. 2011.
Washington Post: In Motion Logging on to Work Out (D. Hudgens)—www.washingtonpost.com/wpsrv/WPcap/1999.
UltraCoach Multi-Sport Fitness Data Management Manual.
Grant of Reexam 95/002359 dated Dec. 6, 2012.
Non-Final Office Action 95/002359 dated Dec. 6, 2012.
Request for Reexam 95/002359 dated Sep. 14, 2012.
Response to Office Action 95/002359 dated Mar. 6, 2013.
Comments by Third Party Requesters to Patent Owner's Response in 95/002359 dated Apr. 5, 2013.
Letter to 2peak AG dated Oct. 12, 2012 regarding US Patent No. 6701271 and 7789800.
Letter to Activio AB dated Oct. 12, 2012 regarding US Patent No. 6701271 and 7789800.
Letter to Angeion Corporation dated Oct. 12, 2012 regarding US Patent No. 6701271 and 7789800.
Letter to Beijing Inforson dated Oct. 12, 2012 regarding US Patent No. 6701271 and 7789800.
Letter to BodyMedia, Inc. dated Oct. 15, 2012 regarding US Patent No. 6701271 and 7789800.
Letter to Finis, USA dated Oct. 12, 2012 regarding US Patent No. 6701271 and 7789800.
Letter to FitBit dated Oct. 12, 2012 regarding US Patent No. 6701271 and 7789800.
Letter to FitBug Limited dated Oct. 12, 2012 regarding US Patent No. 6701271 and 7789800.
Letter to GlobalSat Technology Corp. dated Oct. 12, 2012 regarding US Patent No. 6701271 and 7789800.
Letter to gobandit, GmbH dated Oct. 15, 2012 regarding US Patent No. 6701271 and 7789800.
Letter to Gruve Technologies, Inc. dated Oct. 15, 2012 regarding US Patent No. 6701271 and 7789800.
Letter to iTMP dated Oct. 12, 2012 regarding US Patent No. 6701271 and 7789800.
Letter to Mad Dogg dated Oct. 12, 2012 regarding US Patent No. 6701271 and 7789800.
Letter to MiTAC Digital Corp. dated Oct. 12, 2012 regarding US Patent No. 6701271 and 7789800.
Letter to MyTrak dated Oct. 15, 2012 regarding US Patent No. 6701271 and 7789800.
Letter to MyZone dated Oct. 17, 2012 regarding US Patent No. 6701271 and 7789800.
Letter to Philips Electronics North America Corporation dated Oct. 12, 2012 regarding US Patent No. 6701271 and 7789800.
Letter to Pyle Audio dated Oct. 12, 2012 regarding US Patent No. 6701271 and 7789800.
Letter to Recon Instruments, Inc. dated Oct. 12, 2012 regarding US Patent No. 6701271 and 7789800.
Letter to Runtastic GmbH dated Oct. 12, 2012 regarding US Patent No. 6701271 and 7789800.
Letter to SARL ExcelLance dated Oct. 12, 2012 regarding US Patent No. 6701271 and 7789800.
Letter to Scosche Industries dated Oct. 12, 2012 regarding US Patent No. 6701271 and 7789800.
Letter to Striiv dated Oct. 15, 2012 regarding US Patent No. 6701271 and 7789800.
Letter to Sutinto USA dated Oct. 12, 2012 regarding US Patent No. 6701271 and 7789800.
Letter to Timex Corporation dated Oct. 12, 2012 regarding US Patent No. 6701271 and 7789800.
Letter to Velocomp LLP dated Oct. 12, 2012 regarding US Patent No. 6701271 and 7789800.
Letter to Vidaone dated Oct. 12, 2012 regarding US Patent No. 6701271 and 7789800.
Letter to Virgin dated Oct. 12, 2012 regarding US Patent No. 6701271 and 7789800.
Letter to Wahoo Fitness dated Oct. 12, 2012 regarding US Patent No. 6701271 and 7789800.
Letter to Withings dated Oct. 12, 2012 regarding US Patent No. 6701271 and 7789800.
Letter to Zamzee dated Oct. 12, 2012 regarding US Patent No. 6701271 and 7789800.
Letter to Zeo, Inc. dated Oct. 12, 2012 regarding US Patent No. 6701271 and 7789800.
Letter to Zephyr dated Oct. 12, 2012 regarding US Patent No. 6701271 and 7789800.
Letter from ExcelLance to Larry R. Laycock dated Oct. 17, 2012 regarding US Patent No. 6701271 and 7789800.
Letter from Zeo to Larry R. Laycock dated Oct. 25, 2012 regarding US Patent No. 6701271 and 7789800.
Letter to Motorola Mobility, Inc. dated Oct. 29, 2012 regarding US Patent No. 6701271 and 7789800.
Letter to Nike, Inc. dated Oct. 29, 2012 regarding US Patent No. 670127 and 7789800.
*Icon Health & Fitness, Inc.* vs. *Fitnesskeeper, Inc.*, Complaint filed Dec. 9, 2011.
*Icon Health & Fitness, Inc.* vs. *Fitnesskeeper, Inc.*, Fitness Keeper's Motion to Dismiss Plaintiff's Complaint filed Jun. 11, 2012.
*Icon Health & Fitness, Inc.* vs. *Fitnesskeeper, Inc.*, Memorandum of Points and Authorities in Support of Fitnesskeeper, Inc.'s Motion to Dismiss Plaintiff's Complaint filed Jun. 11, 2012.

(56) References Cited

OTHER PUBLICATIONS

*Icon Health & Fitness, Inc.* vs. *Fitnesskeeper, Inc.*, Icon Health & Fitness, Inc.'s Opposition to Fitness Keeper's Motion to Dismiss Plaintiff's Complaint filed Jul. 12, 2012.
*Icon Health & Fitness, Inc.* vs. *Fitnesskeeper, Inc.*, Reply Memorandum of Points and Authorities in Support of Fitnesskeeper, Inc.'s Motion to Dismiss Plaintiff's Complaint filed Jul. 30, 2012.
*Icon Health & Fitness, Inc.* vs. *Garmin, Ltd.*; Garmin International, Inc.; and Garmin USA, Inc., Complaint filed Nov. 18, 2011.
*Icon Health & Fitness, Inc.* vs. *Garmin, Ltd.*; Garmin International, Inc.; and Garmin USA, Inc., First Amended Complaint filed Jun. 8, 2012.
*Icon Health & Fitness, Inc.* vs. *Garmin, Ltd.*; Garmin International, Inc.; and Gamin USA, Inc., Garmin's Answer to Plaintiff's First Amended Complaint filed Jun. 25, 2012.
*Icon Health & Fitness, Inc.* vs. *Garmin, Ltd.*; Garmin International, Inc.; and Garmin USA, Inc., Garmin's Partial Motion to Dismiss filed Jun. 25, 2012.
*Icon Health & Fitness, Inc.* vs. *Garmin, Ltd.*; Garmin International, Inc.; and Garmin USA, Inc., Memorandum of Supporting Authorities for Garmin's Partial Motion to Dismiss filed Jun. 25, 2012.
*Icon Health & Fitness, Inc.* vs. *Garmin, Ltd.*; Garmin International, Inc.; and Garmin USA, Inc., Icon Health & Fitness, Inc.'s Opposition to Garmin's Partial Motion to Dismiss filed Jul. 26, 2012.
*Icon Health & Fitness, Inc.* vs. *Garmin, Ltd.*; Garmin International, Inc.; and Garmin USA, Inc., Reply in Support of Garmin's Partial Motion to Dismiss filed Aug. 13, 2012.
*Icon Health & Fitness, Inc.* vs. *Gamin, Ltd.*; Garmin International, Inc.; and Garmin USA, Inc., Garmin's Proposed Terms and Claim Elements for Construction filed Feb. 25, 2013.
*Icon Health & Fitness, Inc.* vs. *Garmin, Ltd.*; Garmin International, Inc.; and Garmin USA, Inc., Icon Proposed Terms and Claim Elements for Construction filed Feb. 25, 2013.
*Icon Health & Fitness, Inc.* vs. *Garmin, Ltd.*; Garmin International, Inc.; and Garmin USA, Inc., Deposition of Edith Stern dated Dec. 12, 2012 (5 Pages).
*Icon Health & Fitness, Inc.* vs. *Garmin, Ltd.*; Garmin International, Inc.; and Garmin USA, Inc., Deposition of Barry Willner dated Dec. 12, 2012.
*Icon Health & Fitness, Inc.* vs. *Garmin, Ltd.*; Garmin International, Inc.; and Garmin USA, Inc., Deposition of Edith Stern dated Dec. 12, 2012 (12 Pages).
*Icon Health & Fitness, Inc.* vs. *Garmin, Ltd.*; Garmin International, Inc.; and Garmin USA, Inc., Icon's Preliminary Infringement Contentions dated Nov. 15, 2012.
*Icon Health & Fitness, Inc.* vs. *Garmin, Ltd.*; Garmin International, Inc.; and Garmin USA, Inc., Preliminary List of Accused Instrumentalities.
*Icon Health & Fitness, Inc.* vs. *Garmin, Ltd.*; Garmin International, Inc.; and Garmin USA, Inc., Garmin's Rule 26 Initial Disclosures dated Sep. 26, 2012.
*Icon Health & Fitness, Inc.* vs. *Garmin, Ltd.*; Garmin International, Inc.; and Garmin USA, Inc., Icon's Initial Disclosures dated Sep. 26, 2012.
*Icon Health & Fitness, Inc.* vs. *Garmin, Ltd.*; Garmin International, Inc.; and Garmin USA, Inc., Garmin's Responses to Plaintiff Icon's First Set of Interrogatories to Defendants (Nos. 1-9) dated Oct. 15, 2012.
*Icon Health & Fitness, Inc.* vs. *Garmin, Ltd.*; Garmin International, Inc.; and Garmin USA, Inc., Icon's Objections and First Supplemental Responses to Garmen's First Set of Interrogatories (Nos. 1-8) dated Oct. 22, 2012.
*Icon Health & Fitness, Inc.* vs. *Garmin, Ltd.*; Garmin International, Inc.; and Garmin USA, Inc., Icon's Objections and First Supplemental Responses to Garmin's First Set of Interrogatiories (Nos. 1-8) dated Oct. 22, 2012.
*Icon Health & Fitness, Inc.* vs. *Garmin, Ltd.*; Garmin International, Inc.; and Garmin USA, Inc., Defendants' Preliminary Invalidity Contentions dated Jan. 25, 2013.

*Icon Health & Fitness, Inc.* vs. *MapMy Fitness, Inc.*, Complaint filed Dec. 9, 2011.
*Icon Health & Fitness, Inc.* vs. *MapMyFitness, Inc.*, First Amended Complaint filed Dec. 6, 2012.
*Icon Health & Fitness, Inc.* vs. *MapMyFitness, Inc.*, Answer to First Amended Complaint and Counterclaims filed Dec. 21, 2012.
*Icon Health & Fitness, Inc.* vs. *MapMyFitness, Inc.*, Icon Health & Fitness Inc.'s Answer to Defendant's Counterclaims filed Jan. 21, 2013.
*Icon Health & Fitness, Inc.* vs. *MapMyFitness, Inc.*, MapMyFitness, Inc.'s Motion to Dismiss Plaintiff's Complaint filed Jun. 14, 2012.
*Icon Health & Fitness, Inc.* vs. *MapMyFitness, Inc.*, Memorandum of Points and Authorities in Support of MapMyFitness, Inc.'s Motion to Dismiss Plaintiff's Complaint filed Jun. 14, 2012.
*Icon Health & Fitness, Inc.* vs. *MapMyFitness, Inc.*, Icon Health & Fitness, Inc.'s Opposition to MapMyFitness, Inc.'s Motion to Dismiss Plaintiff's Complaint filed Jul. 16, 2012.
*Icon Health & Fitness, Inc.* vs. *MapMyFitness, Inc.*, Reply Memorandum in Support of MapMyFitness, Inc.'s Motion to Dismiss Plaintiff's Complaint filed Aug. 2, 2012.
*Icon Health & Fitness, Inc.* vs. *Polar Electro Oy*, Complaint filed Nov. 18, 2011.
*Icon Health & Fitness, Inc.* vs. *Polar Electro Oy*, First Amended Complaint filed Jun. 8, 2012.
*Icon Health & Fitness, Inc.* vs. *Polar Electro Oy*, Polar Electro Oy's and Polar Electro Inc.'s Answer and Counterclaim to Plaintiff's First amended Complaint filed Dec. 12, 2012.
*Icon Health & Fitness, Inc.* vs. *Polar Electro Oy*, Icon Health & Fitness Inc.'s Answer to Defendants' Counterclaims and Icon Health & Fitness, Inc.'s Counterclaims filed Jan. 21, 2013.
*Icon Health & Fitness, Inc.* vs. *Polar Electro Oy*, Polar Electro Oy's and Polar Electro Inc.'s Answer and Counterclaim to Plaintiff's Counterclaims filed Feb. 11, 2013.
*Icon Health & Fitness, Inc.* vs. *Polar Electro Oy*, Polar Electro Oy's and Polar Electro Inc.'s Opposition to Icon's Motion to Partially Dismiss Defendants' Counterclaims filed Feb. 21, 2013.
*Icon Health & Fitness, Inc.* vs. *Polar Electro Oy*, Icon Health & Fitness Inc.'s Reply in Support of Icon's Motion to Partially Dismiss Defendant's Counterclaims filed Mar. 11, 2013.
*Icon Health & Fitness, Inc.* vs. *Polar Electro Oy*, Icon's Initial Disclosures dated Mar. 1, 2013.
*Icon Health & Fitness, Inc.* vs. *Polar Electro Oy*, Reply in Support of Its Motion for a Partial Stay Pending Reexamination of Two Patents-In-Suit dated Mar. 1, 2013.
*Icon Health & Fitness, Inc.* vs. *Polar Electro Oy*, Polar Electro Oy's and Polar Electro Inc.'s Rule 26(a)(1) Initial Disclosures dated Mar. 1, 2013.
*Icon Health & Fitness, Inc.* vs. *Polar Electro Oy*, Icon Health & Fitness Inc.'s Motion to Partially Dismiss Defendants' Counterclaims filed Jan. 21, 2013.
*Icon Health & Fitness, Inc.* vs. *Strava, Inc.*, Complaint filed Dec. 9, 2011.
*Icon Health & Fitness, Inc.* vs. *Strava, Inc.*, Strava, Inc.'s Motion to Dismiss Plaintiff's Complaint filed Dec. 9, 2011.
*Icon Health & Fitness, Inc.* vs. *Strava, Inc.*, Memorandum of Points and Authorities in Support of Strava, Inc.'s Motion to Dismiss Plaintiff's Complaint filed Jun. 11, 2012.
*Icon Health & Fitness, Inc.* vs. *Strava, Inc.*, Icon Health & Fitness, Inc.'s Opposition to Strava, Inc.'s Motion to Dismiss Plaintiff's Complaint filed Jul. 12, 2012.
*Icon Health & Fitness, Inc.* vs. *Strava, Inc.*, Strava, Inc.'s Reply in Support of Its Motion to Dismiss Plaintiff's Complaint filed Jul. 30, 2012.
Icon Health and Fitness Inc., Photographs of various fitness equipment systems, 1989-1996.
American Express Workout Warehouse, Winter 1999, available on information and belief at least as early as Jan. 1999, 20 pages.
"Best Values in Treadmills," Consumer Reports, Jun. 2003,4 pages.
"Stay Fit," Consumer Reports, available on information and belief at least as early as Feb. 2002, 8 pages.
"Treadmills & Ellipticals: Indoor exercise." Consumer Reports, Jan. 2005, 6 pages.

(56) References Cited

OTHER PUBLICATIONS

Treadmills for Jogs and 'Walkouts.' Consumer Reports, Jan. 1996, 5 pages.
"Treadmills." Consumer Reports, available on information and belief at least as early as Oct. 1990, 8 pages.
"Treadmills." Consumer Reports, available on information and belief at least as early as Dec. 1997, 5 pages.
"Treadmills: More for the Money." Consumer Reports, Feb. 2004, 4 pages.
Consumer Reports.org—Treadmill ratings, Feb. 2004, 3 pages.
Brochure for Quinton Instruments, 1974, 34 pages.
Brochure for Genesis 3000, Technology for Total Fitness entitled "The Dynamic Answer to Home Fitness and Health" © Genesis, Inc., Sep. 1985, 1 page without page number).
"Brochure for Genesis 4000""Technology for Total Fitness entitled""The Modern Approach to Home Fitness and Health""© Genesis, Inc.,Sep. 1985, 2 pages without page numbers.".
Brochure entitled "Technology for Total Fitness Genesis 3000", © 1985 Genesis, Inc.) 7 pages.
Brochure entitled "Technology for Total fitness Genesis 4000", © 1985 Genesis, Inc.) 5 pages.
Damark International, Inc. Mail Order Catalog, dated Nov. 17, 1994, cover page and p. 6.
Diaz, Francisco Jose, et al. "Evolncion de las caracteristicas fisicas y funcionales en jugadores de futbol soccer," Rivista de hivestigacion Clinica, vol. 55, Num. 5, Sep.-Oct. 2003, 528-534.
Healthrider: Softstrider—A Series (A60) User's Manual, Copyright 1999 ICON Health & Fitness, Inc., 26 pages.
Healthrider Softstrider—A Series (A90) User's Manual, Copyright 1999 ICON Health & Fitness, Inc., 26 pages.
Heil, Daniel P. "Scaling of Submaximal Oxygen Uptake with Body Mass and Combined Mass During Uphill Treadmill Bicycling." Journal of Applied Physiology (Oct. 1998): 1376-1383.
Images from DVD movie, Rocky IV, scene 25, (including views of treadmill with inclining treadbase), and credit page (1), and copyright page (1), copyright 1985, 17 total pages.
Jakicic, S.M., et al. "The Accuracy of the TriTrac-R3D Accelerometer to Estimate Energy Expenditure." Medicine & Science in Sports & Exercise (May 1999): 747-754.
LifeFitness Website pages, available on information and belief at least as early as Oct. 2000, 12 pages.
McMorris, Megan, "Gear—Running in Place", Runner's World, Feb. 2006, 4 pages.
MedGraphics Cardiorespiratory Diagnostic Products http://www.medgraphics.com/products_main.html, printed Sep. 9, 2004, 2 pages.
"Robertson, Robert J., et al. ""Gender Comparison of RPE at Absolute and Relative Physiological Criteria."" Medicine and Science in Sports & Exercise, Dec. 2000, pp. 2120-2129."
Sears, Roebuck and Co., Pro-Form 585TL Low Profile Treadmill, User's Manual, Copyright 1996 (20 pages).
Shu-Lin Li. "The Effects of Beverage Containing Antioxidants and Carbohydrate Supplementation on Physiology and Blood Biochemistry in Endurance Exercise and Recovery Period." National College of Physical Education and Sports Taiwan Republic of China, 85 pages, 2001, (includes title page and English Abstract), and 3 pages of English translation.
Su-Jen Wang. "The Gait Analysis of Females with Flat foot and Normal foot in Walking and Running." National College of Physical Education and Sports Taiwan Republic of China, 134 pages, 2004 (includes title page and English Abstract).
Treadmill Owner's Manual by Formula 22100 Manual Treadmill, upon information and belief, available at least as early as 1998, 20 pages.
Treadmills Rating @ Treadmill Warehouse.net, http://www.treadmillwarehouse.net/affordable-treadmills-running-walking-fitness-equipment-exercisers-rating.htm, printed Feb. 24, 2006, 2 pages.
U.S. Appl. No. 60/159,268, filed Oct. 13, 1999 to Thomas F. Smith Jr. et al. entitled Exercise Treadmill (6 pages).
Wen-Chi Chen. "The Biomechanical Study of Normal Foot and Flat Foot in Walking and Running.", 113 pages, 2002, (includes title page and English Abstract).
Weslo Cadence 1020 User's Manual, copyright 1998 ICON Health & Fitness, Inc., 18 pages).
"Trackmaster Introduces the All-New TMX Series Treadmills; Longer, Wider, Quieter, and Packed with User Preferred Features," National Fitness Trade Journal, Fall 2001, 4 pages.
"Absolutely Motivating. Exceptional Performance. Trademark Feel." ExerTools. Training & Conditioning, Nov. 1999, vol. IX, No. 8, 1 page.
Kettler World Tours—Trainin, http://www.kettlerworldtours.de/en/main/, Feb. 23, 2011 (17 pp).
Photographs of Trackmaster Treadmill TM500, SER. 12165 AC, which was available on information and belief, at least as early as 1995 (11 photographs). (Originals filed in U.S. Appl. No. 11/113,921 on Jan. 24, 2007).
DVD containing video images of Trackmaster Treadmill TM500, SER. 12165 AC, which was available, on information and belief, at least as early as 1995 (approximately eleven minutes) (Original filed in U.S. Appl. No. 11/113,921 on Jan. 24, 2007).
Photographs of Trackmaster Treadmill TM500/S, SER. 9756, which was available, on information and belief, at least as early as 1994 (9 photogaphs). (Originals filed in U.S. Appl. No. 11/113,921 on Jan. 24, 2007).
Amendment "C" dated Jan. 24, 2007, Examiner Interview, p. 17 (1 page).
Athletic Business, Tectirix Fitness Equipment, Jul. 1997, 1 page.
RunnersWorld.com forum post dated Mar. 28, 2008, 5 Pages.
Virtual Active by Matrix Advertisement, available, on information and belief, at least as early as Oct. 2009, 1 page.
"Virtual Active by Matrix website http://www.matrixfitness.com/products/treadmills/va/aspprinted on Jan. 28, 2010, 2 pages."
"*Cybergym Research LLC* v. *ICON Health & Fitness, Inc.*, (Case No. 2:05-CV-527):Plaintiff Cybergym Research LLC's Disclosure of Asserted Claims and Preliminary Infringement Contentions, signed by William C. Milks, III on Apr. 7, 2006."
"*Cybergym Research LLC* v. *ICON Health & Fitness, Inc.*, (Case No. 2:05-CV-527):Plaintiff Cybergym Research LLC's Amended Infringement Contentions Pursuant to P.R. 3-6(a), signed by William C. Milks , III on Feb. 26, 2007."
"*Cybergym Research LLC* v. *ICON Health & Fitness, Inc.*, (Case No. 2:05-CV-527):Icon's First Amended Answer to First Amended Complaint and First Amended Couterclaim, signed by Kirk Harris on Mar. 16, 2007."
"*Cybergym Research LLC* v. *ICON Health & Fitness, Inc.*, (Case No. 2:05-CV-527): Icon Health & Fitness, Inc.'s Mediation Brief, signed by Brett Hansen on Aug. 16, 2006."
"*Cybergym Research LLC* v. *ICON Health & Fitness, Inc.*, (Case No. 2:05-CV-527): Plaintiff Cybergym Research, LLC's Notice of Motion and Motion for Partial Summary judgment Regarding Infringement of Claim 6 of the '631 Patent and Claim1 of the '537 Patent by Defendant Icon Health & Fitness, Inc.; Memorandum of Points and Authorities in Support Thereof, signed by William C. Milks, III on Jun. 1, 2007."
"*Cybergym Research LLC* v. *ICON Health & Fitness, Inc.*, (Case No. 2:05-CV-527):Defendant's Opposition to Cybergym's Motion for Partial Summary Judgment Regarding Infringement of Claim 6 of the 631 Patent and Claim 1 of the 537 Patent by Defendant Icon Health & Fitness, Inc., signed by David Folsom on Jan. 25, 2007."
"*Cybergym Research LLC* v. *ICON Health & Fitness, Inc.*, (Case No. 2:05-CV-527): Defendant's Sur-Reply in Further Opposition to Cybergym's Motion for Partial Summary Judgment Regarding Infringement of Claim 6 of the '631 Patent and Claim1 of the '537 Patent by Defendant Icon Health & Fitness, Inc., signed by Charles L. Roberts on Jul. 9, 2007."
"*Cybergym Research LLC* v. *ICON Health & Fitness, Inc.*, (Case No. 2:05-CV-527): Order regarding Plaintiff's Motion for Partial Summary Judgment Regarding Infringement of Claim 6 of the '631 Patent and Claim 1 of the '537 Patent, signed by David Folsom on Sep. 4, 2007."
"*Cybergym Research LLC* v. *ICON Health & Fitness, Inc.*, (Case No. 2:05-CV-527): Defendant's Motion and Memorandum for Partial

(56) References Cited

OTHER PUBLICATIONS

Summary Judgment of Non-Infringement of Claims 6, 1, and 10, signed by Charles L. Robert on Jun. 1, 2007."
"*Cybergym Research LLC v. ICON Health & Fitness, Inc.*, (Case No. 2:05-CV-527):Defendant's Reply Brief in Further Support of its Motion for Summary Judgment of Non-Infringement of Claims 6,1, and 10, signed by Charles L. Roberts on Jun. 28, 2007."
"*Cybergym Research LLC v. ICON Health & Fitness, Inc.*, (Case No. 2:05-CV-527): Order regarding Defendant's Motion for Partial Summary Judgment of Non-Infringement of Claims 6, 1, and 10, signed by David Folsom on Sep. 4, 2007."
"*Cybergym Research LLC v. ICON Health & Fitness, Inc.*, (Case No. 2:05-CV-527): Cybergym Research, LLC's supplemental initial disclosures, available on information and belief at least as early as Jun. 1, 2006."
"*Cybergym Research LLC v. ICON Health & Fitness, Inc.*, (Case No. 2:05-CV-527): Defendant Icon Health & Fitness, Inc.'s Answers and Objections to Plaintiff's First Set of Interrogatories, signed by Brett Hansen on Aug. 14, 2006."
"*Cybergym Research LLC v. ICON Health & Fitness, Inc.*, (Case No. 2:05-CV-527): Plaintiff's Objections and Response to Defendant's First Set of Interrogatories, signed by William Milks on Jul. 24, 2006."
"*Cybergym Research LLC v. ICON Health & Fitness, Inc.*, (Case No. 2:05-CV-527): Plaintiff Cybergym Research LLC's Initial Disclosures, signed by William C. Milks, III on Apr. 7, 2006."
"*Cybergym Research LLC v. ICON Health & Fitness, Inc.*, (Case No. 2:05-CV-527): Defendant's Rule 26 Initial Disclosures, signed by H. Craig Hall on Apr. 7, 2006."
"*Cybergym Research LLC v. ICON Health & Fitness, Inc.*, (Case No. 2:05-CV-527): Defendant Icon Health & Fitness, Inc.'s Second Supplemental Answers and Objections to Plaintiff's First Set of Interrogatories, signed by Tige Keller on Mar. 23, 2007."
"*Cybergym Research LLC v. ICON Health & Fitness, Inc.*, (Case No. 2:05-CV-527): Defendant Icon Health & Fitness, Inc.'s Supplemental Rule 26(a) Disclosures, signed on Tige Keller on Mar. 23, 2007."
"*Cybergym Research LLC v. ICON Health & Fitness, Inc.*, (Case No. 2:05-CV-527): Defendant Icon Health & Fitness, Inc.'s First Supplemental Answers and Objections to Plaintiff's First Set of Interrogatories, signed by Kirk Harris on Feb. 26, 2007."
"*Cybergym Research LLC v. ICON Health & Fitness, Inc.*, (Case No. 2:05-CV-527): Defendant Icon Health & Fitness, Inc.'s Answers and Objections to Plaintiff's Third Set of Interrogatories, signed by Kirk Harris on Jan. 29, 2007."
"*Cybergym Research LLC v. ICON Health & Fitness, Inc.*, (Case No. 2:05-CV-527): Defendant Icon Health & Fitness, Inc.'s Responses to Plaintiff's Second Set of Requests for Admission [Amended], signed by Charles L. Roberts on Jan. 26, 2007."
"*Cybergym Research LLC v. ICON Health & Fitness, Inc.*, (Case No. 2:05-CV-527): Plaintiff's Supplemental Objections and Responses to Defendants' First Set of Requests for Admission, signed by William C. Milks, III on Jan. 23, 2007."
"*Cybergym Research LLC v. ICON Health & Fitness, Inc.*, (Case No. 2:05-CV-527): Plaintiff Cybergym Research LLC's Objections and Responses to Defendants' Third Set of Interrogatories and Second Set of Requests to Admit, signed by William C. Milks, III on Jan. 23, 2007."
"*Cybergym Research LLC v. ICON Health & Fitness, Inc.*, (Case No. 2:05-CV-527): Plaintiff's Supplemental Objections and Responses to Defendants' Second Set of Interrogatories, signed by William C. Milks, III on Jan. 23, 2007."
"*Cybergym Research LLC v. ICON Health & Fitness, Inc.*, (Case No. 2:05-CV-527):Defendant Icon Health & Fitness, Inc.'s Response to Interrogatory No. 12, signed by Kirk R. Harris on Jan. 16, 2007."
"*Cybergym Research LLC v. ICON Health & Fitness, Inc.*, (Case No. 2:05-CV-527): Defendant Dick's Sports Goods, Inc. Responses and Objections to Plaintiff's First Set of Interrogatories, signed by Charles L. Roberts on Dec. 18, 2006."
"*Cybergym Research LLC v. ICON Health & Fitness, Inc.*, (Case No. 2:05-CV-527):Defendant Sports Authority, Inc. Responses and Objections to Plaintiff's First Set of Interrogatories, signed by Charles L. Roberts on Dec. 18, 2006."
"*Cybergym Research LLC v. ICON Health & Fitness, Inc.*, (Case No, 2:05-CV-527):Plaintiff's Objections and Responses to Defendants' First Set of Requests for Admission, signed by Tim C. Hale on Dec. 18, 2006."
"*Cybergym Research LLC v. ICON Health & Fitness, Inc.*, (Case No. 2:05-CV-527): Plaintiffs Objections and response to Defendants' Second Set of Interrogatoties, signed by Tim C. Hale on Dec. 18, 2006."
"*Cybergym Research LLC v. ICON Health & Fitness, Inc.*, (Case No. 2:05-CV-527): Defendant Costco Wholesale Corp. Responses and Objections to Plaintiff's First Set of Interrogatories, signed by Charles L. Roberts on Dec. 21, 2006."
"*Cybergym Research LLC v. ICON Health & Fitness, Inc.*, (Case No. 2:05-CV-527):Defendant Sears, Roebuck and Co.'s Responses and Objections to Plaintiff's First Setof Interrogatories, signed by Charles L. Roberts on Dec. 18, 2006."
"*Cybergym Research LLC v. ICON Health & Fitness, Inc.*, (Case No. 2:05-CV-527): Defendant Icon Health and Fitness, Inc.'s Response to Interrogatory No. 13, signed by Kirk Harris on Dec. 15, 2006."
"*Cybergym Research LLC v. ICON Health & Fitness, Inc.*, (Case No. 2:05-CV-527): Defendant Icon Health & Fitness, Inc.'s Supplemental Responses to Plaintiff's First Set of Requests for Admissions, signed by Kirk Harris on Nov. 7, 2006."
"*Cybergym Research LLC v. ICON Health & Fitness, Inc.*, (Case No. 2:05-CV-527): Defendant Icon Health & Fitness, Inc.'s [Corrected] Answers and Objections to Plaintiff's First Set of Interrogatories, signed by Brett A. Hansen on Oct. 20, 2006."
"*Cybergym Research LLC v. ICON Health & Fitness, Inc.*, (Case No. 2:05-CV-527): Defendant Icon Health & Fitness, Inc.'s Responses to Plaintiff's First Set of Requests for Admissions, signed by Brett Hansen on Aug. 28, 2006."
"*Cybergym Research LLC v. ICON Health & Fitness, Inc.*, (Case No. 2:05-CV-527): Plaintiff's Supplemental Objections and Response to Defendant's First Set of Interrogatories, signed by William C. Milks on Aug. 18, 2006."
"*Cybergym Research LLC v. ICON Health & Fitness, Inc.*, (Case No. 2:05-CV-527): Defendant Icon Health & Fitness, Inc.'s Answers and Objections to Plaintiff's Fourth Set of Interrogatories, signed by Charles L. Roberts on Jun. 12, 2007."
"*Cybergym Research LLC v. ICON Health & Fitness, Inc.*, (Case No. 2:05-CV-527): Rebuttal Expert Report of Glenn von Tersch under Rule 26(a)(2) of the Federal Rules of Civil Procedure and Rule 702 of the Federal Rules of Evidence, signed by Glenn E.von Tersch on Apr. 6, 2007."
"*Cybergym Research LLC v. ICON Health & Fitness, Inc.*, (Case No. 2:05-CV-527): Rebuttal Expert Report of Dr. Brent Nelson Pursuant to Federal Rule of Civil Procedure 26(a)(2)(B), signed by Brent E. Nelson on Apr. 5, 2007."
"*Cybergym Research LLC v. ICON Health & Fitness, Inc.*, (Case No. 2:05-CV-527): Rebuttal Expert Report on John L. Berman Under Rule 26(a)(2) of the Federal Rules of Civil Procedure and Rule 702 of the Federal Rules of Evidence, signed by John L. Berman on Apr. 6, 2007."
"*Cybergym Research LLC v. ICON Health & Fitness, Inc.*, (Case No. 2:05-CV-527): Expert Report on John L. Berman under Rule 26(a)(2) of the Federal Rules of Civil Procedure and Rule 702 of the Federal Rules of Evidence, signed by John L. Berman on Mar. 13, 2007."
"*Cybergym Research LLC v. ICON Health & Fitness, Inc.*, (Case No. 2:05-CV-527): Rebuttal Expert Witness Report of Paul W. Vapnek (document not enclosed due to protections provided by Stipulated Protective Order issued by Judge David Folsom on May 15, 2006; however, a waiver of the Stipulated Protective Order protections has been requested from Paul Hickman of Cybergym Research, LLC)."
"*Cybergym Research LLC v. ICON Health & Fitness, Inc.*, (Case No. 2:05-CV-527): Expert Witness Report of Thomas F. Smegal, Jr. (document not enclosed due to protections provided by Stipulated Protective Order issued by Judge David Folsom on May 15, 2006; however, a waiver of the Stipulated Protective Order protections has been requested from Paul Hickman of Cybergym Research, LLC)."

(56) References Cited

OTHER PUBLICATIONS

"*Cybergym Research LLC* v. *ICON Health & Fitness, Inc.*, (Case No. 2:05-CV-527): Videotaped Deposition of John Berman Conducted on Thursday, Apr. 26, 2007."
"*Cybergym Research LLC* v. *ICON Health & Fitness, Inc.*, (Case No. 2:05-CV-527): Videotaped Deposition of Paul Hickman Conducted on Thursday, Feb. 8, 2007."
"*Cybergym Research LLC* v. *ICON Health & Fitness, Inc.*, (Case No. 2:05-CV-527): Videotaped Deposition of Glenn von Tersch Conducted on Tuesday, May 15, 2007."
"*Cybergym Research LLC* v. *ICON Health & Fitness, Inc.*, (Case No. 2:05-CV-527):Videotaped Deposition of Glenn von Tersch, vol. 2, conducted on Tuesday, May 29, 2007."
"*Cybergym Research LLC* v. *ICON Health & Fitness, Inc.*, (Case No. 2:05-CV-527):Videotaped Deposition of Paul Vapnek Conducted on Monday, May 14, 2007."
"*Cybergym Research LLC* v. *ICON Health & Fitness, Inc.*, (Case No. 2:05-CV-527):Deposition of Thomas Smegal, Jr. on May 15, 2007."
"*Cybergym Research LLC* v. *ICON Health & Fitness, Inc.*, (Case No. 2:05-CV-527):Deposition of Brent E. Nelson, Ph.D. on Apr. 27, 2007."
"*Cybergym Research LLC* v. *ICON Health & Fitness, Inc.*, (Case No. 2:05-CV-527):Deposition of Paul Hickman on Feb. 6, 2007 (document not enclosed due to protections provided by Stipulated Protective Order issued by Judge David Folsom on May 15, 2006; however, a waiver of the Stipulated Protective Order protections has been requested from Paul Hickman of Cybergym Research, LLC)."
"*Cybergym Research LLC* v. *ICON Health & Fitness, Inc.*, (Case No. 2:05-CV-527): Deposition of Michael Gough on Feb. 7, 2007 (document not enclosed due to protections provided by Stipulated Protective Order issued by Judge David Folsom on May 15, 2006; however, a waiver of the Stipulated Protective Order protections has been requested from Paul Hickman of Cybergym Research, LLC)."
"*Cybergym Research LLC* v. *ICON Health & Fitness, Inc.*, (Case No. 2:05-CV-527): Transcript of Tutorial and Claim Construction Before Judge David Folsom, Dec. 11, 2006."
"*Cybergym Research LLC* v. *ICON Health & Fitness, Inc.*, (Case No. 2:05-CV-527): Transcript of Summary Judgment Motions Hearing Before Judge David Folsom, Jul. 12, 2007."
"*Cybergym Research LLC* v. *ICON Health & Fitness, Inc.*, (Case No. 2:05-CV-527):Transcript of Trial, Oct. 9, 2007."
"*Cybergym Research LLC* v. *ICON Health & Fitness, Inc.*, (Case No. 2:05-CV-527):Transcript of Trial, Oct. 10, 2007."
"*Cybergym Research LLC* v. *ICON Health & Fitness, Inc.*, (Case No. 2:05-CV-527):Transcript of Trial, Oct. 11, 2007."
"*Cybergym Research LLC* v. *ICON Health & Fitness, Inc.*, (Case No. 2:05-CV-527):Transcript of Trial, Oct. 12, 2007."
"*Icon Health & Fitness, Inc.* v. *Johnson Health Tech North America, Inc.*, (Case No. 1:10-CV-00209-DB): Complaint for Patent Infringement, signed by David R. Wright on Dec. 14, 2010."
"*Icon Health & Fitness, Inc.* v. *Johnson Health Tech North America, Inc.*, (Case No. 1:10-CV-00209-DB): Answer and Counterclaims, signed by Brent L. Hatch on Jan. 18, 2011."
"*Icon Health & Fitness, Inc.* v. *Johnson Health Tech North America, Inc.*, (Case No. 1:10-CV-00209-DB): Icon Health & Fitness, Inc.'s Answer to Johnson Health Tech North America, Inc.'s Counterclaims, signed by Charles L. Roberts on Feb. 11, 2011."
"*Icon Health & Fitness, Inc.* v. *Johnson Health Tech North America, Inc.*, (Case No. 1:10-CV-00209-DB): Icon's Responses to Johnson Health Tech North America, Inc.'s First Set of Interrogatories, signed by Charles L. Roberts on Apr. 25, 2011."
"*Icon Health & Fitness, Inc.* v. *Johnson Health Tech North America, Inc.*, (Case No. 10-CV-00209-DB): Johnson Health Tech North America, Inc.'s Responses to Icon Health & Fitness, Inc.'s First Set of Requests for Admission, signed by Gary A. Ahrens on Apr. 18, 2011."
"*Icon Health & Fitness, Inc.* v. *Johnson Health Tech North America, Inc.*, (Case No. 1:10-CV-00209-DB): Johnson Health Tech North America, Inc.'s Responses to IconHealth & Fitness, Inc.'s First Set of Interrogatories, signed by Gary A. Ahrens on Apr. 21, 2011."
"*Icon Health & Fitness, Inc.* v. *Johnson Health Tech North America, Inc.*, (Case No. 1:10-CV-00209-DB): Icon Health & Fitness, Inc.'s Rule 26(a)(1) Initial Disclosures,signed by Charles L. Roberts on May 13, 2011."
"*Icon Health & Fitness, Inc.* v. *Johnson Health Tech North America, Inc.*, (Case No. 1:10-CV-00209-DB): Johnson Health Tech North America, Inc.'s Initial DisclosuresPursuant to Fed. R. Civ. P. 26(a)(1), signed by Kenneth M. Abridge, III on May 13, 2011."
"*Icon Health & Fitness, Inc.* v. *Johnson Health Tech North America, Inc.*, (Case No. 1:10-CV-00209-DB): Plaintiff's Initial Infringement Contentions, signed by Charles L. Roberts on May 27, 2011."
"*Icon Health & Fitness, Inc.* v. *Johnson Health Tech North America, Inc.*, (Case No. 1:10-CV-00209-DB): Johnson Health Tech North America, Inc.'s Initial InvalidityContentions, signed by John C. Scheller on Jun. 24, 2011."
"*Icon Health & Fitness, Inc.* v. *Johnson Health Tech North America, Inc.*, (Case No. 1:10-CV-00209-DB): Icon Health & Fitness, Inc.'s Amended Answer to JohnsonHealth Tech North America, Inc.'s Counterclaims, signed by Charles L. Roberts on Sep. 6, 2011."
"*ICON Health & Fitness, Inc.* v. *Johnson Health Tech North America, Inc.* (Case No. 1:10-cv-00209-DB): Plaintiff's Initial Infringement Contentions ('213 patent), sent to counsel for Defendant by Charles Roberts on Jun. 1, 2011."
"*ICON Health & Fitness, Inc.* v. *Johnson Health Tech North America, Inc.* (Case No. 1:10-cv-00209-DB): Plaintiff's Initial Infringement Contentions ('692 patent), sent to counsel for Defendant by Charles Roberts on Jun. 1, 2011."
"*ICON Health & Fitness, Inc.* v. *Johnson Health Tech North America, Inc.* (Case No. 1:10-cv-00209-DB): Plaintiff's initial Infringement Contentions ('847 patent), sent to counsel for Defendant by Charles Roberts on Jun. 1, 2011."
"*ICON Health & Fitness, Inc.* v. *Johnson Health Tech North America, Inc.* (Case No. 1:10-cv-00209-DB): ICON Health & Fitness, Inc.'s Memorandum and Points of Authority in Support of its Motion for Preliminary Injunction, signed by Charles Roberts on Dec. 23, 2010."
"*ICON Health & Fitness, Inc.* v. *Johnson Health Tech North America, Inc.* (Case No. 1:10-cv-00209-DB): Johnson Health Tech North America, Inc.'s Memorandum and Points of Authority in Opposition to Plaintiffs Motion for Preliminary Injunction, received from Morgan Everett on Jan. 10, 2011. (document not enclosed due to protections provided by Stipulated Protective Order issued by Judge Dee Benson on Apr. 1, 2011.)".
"*ICON Health & Fitness, Inc.* v. *Johnson Health Tech North America, Inc.* (Case No. 1:10-cv-00209-DB): ICON Health & Fitness, Inc.'s Reply Memorandum in Support of its Motion for Preliminary Injunction, signed by Charles Roberts on Apr. 22, 2011.(document not enclosed due to protections provided by Stipulated Protective Order issued by Judge Dee Benson on Apr. 1, 2011.)".
"*ICON Health & Fitness, Inc.* v. *Heinz Kettler Gmbh & Co., KG et al.* (Case No. SACV12-00531 JVS): Complaint for Patent Infringement, signed by Tyson K. Hottinger on Apr. 6, 2012."
"*Cybergym Research LLC* v. *ICON Health & Fitness, Inc.*, (Case No. 2:05-CV-527):Defendant Icon Health and Fitness, Inc.'s Response to Interrogatory No. 13, signed by Kirk Harris on Dec. 15, 2006."
"*Cybergym Research LLC* v. *ICON Health & Fitness, Inc.*, (Case No. 2:05-CV-527):Defendant Icon Health & Fitness, Inc.'s Supplemental Responses to Plaintiff's First Set of Requests for Admissions, signed by Kirk Harris on Nov. 7, 2006."
"*Cybergym Research LLC* v. *ICON Health & Fitness, Inc.*, (Case No. 2:05-CV-527):Defendant Icon Health & Fitness, Inc.'s [Corrected] Answers and Objections to Plaintiff's First Set of Interrogatories, signed by Brett A. Hansen on Oct. 20, 2006."
"*Cybergym Research LLC* v. *ICON Health & Fitness, Inc.*, (Case No. 2:05-CV-527):Defendant Icon Health & Fitness, Inc.'s Responses to Plaintiff's First Set of Requests for Admissions, signed by Brett Hansen on Aug. 28, 2006."
"*Cybergym Research LLC* v. *ICON Health & Fitness, Inc.*, (Case No. 2:05-CV-527):Plaintiff's Supplemental Objections and Response to Defendant's First Set of Interrogatories, signed by William C. Milks on Aug. 18, 2006."
"*Cybergym Research LLC* v. *ICON Health & Fitness, Inc.*, (Case No. 2:05-CV-527):Defendant Icon Health & Fitness, Inc.'s Answers and

(56) References Cited

OTHER PUBLICATIONS

Objections to Plaintiff's Fourth Set of Interrogatories, signed by Charles L. Roberts on Jun. 12, 2007."
"*Cybergym Research LLC* v. *ICON Health & Fitness, Inc.*, (Case No. 2:05-CV-527):Rebuttal Expert Report of Glenn von Tersch under Rule 26(a)(2) of the Federal Rules of Civil Procedure and Rule 702 of the Federal Rules of Evidence, signed by Glenn E.von Tersch on Apr. 6, 2007."
"*Cybergym Research LLC* v. *ICON Health & Fitness, Inc.*, (Case No. 2:05-CV-527):Rebuttal Expert Report of Dr. Brent Nelson Pursuant to Federal Rule of Civil Procedure 26(a)(2)(B), signed by Brent E. Nelson on Apr. 5, 2007."
"*Cybergym Research LLC* v. *ICON Health & Fitness, Inc.*, (Case No. 2:05-CV-527):Rebuttal Expert Report on John L. Berman Under Rule 26(a)(2) of the Federal Rules of Civil Procedure and Rule 702 of the Federal Rules of Evidence, signed by John L. Berman on Apr. 6, 2007."
"*Cybergym Research LLC* v. *ICON Health & Fitness, Inc.*, (Case No. 2:05-CV-527):Expert Report on John L. Berman under Rule 26(a)(2) of the Federal Rules of Civil Procedure and Rule 702 of the Federal Rules of Evidence, signed by John L. Berman on Mar. 13, 2007."
"*Cybergym Research LLC* v. *ICON Health & Fitness, Inc.*, (Case No. 2:05-CV-527):Rebuttal Expert Witness Report of Paul W. Vapriek (document not enclosed due to protections provided by Stipulated Protective Order issued by Judge David Folsom on May 15, 2006; however, a waiver of the Stipulated Protective Order protections has been requested from Paul Hickman of Cybergym Research, LLC)."
"*Cybergym Research LLC* v. *ICON Health & Fitness, Inc.*, (Case No. 2:05-CV-527):Expert Witness Report of Thomas F. Smegal, Jr. (document not enclosed dueto protections provided by Stipulated Protective Order issued by Judge David Folsom on May 15, 2006; however, a waiver of the Stipulated Protective Order protections has been requested from Paul Hickman of Cybergym Research, LLC)."
"*Cybergym Research LLC* v. *ICON Health & Fitness, Inc.*, (Case No. 2:05-CV-527):Videotaped Deposition of John Berman Conducted on Thursday, Apr. 26, 2007."
"*Cybergym Research LLC* v. *ICON Health & Fitness, Inc.*, (Case No. 2:05-CV-527):Videotaped Deposition of Paul Hickman Conducted on Thursday, Feb. 8, 2007."
"*Cybergym Research LLC* v. *ICON Health & Fitness, Inc.*, (Case No. 2:05-CV-527); Videotaped Deposition of Glenn von Tersch Conducted on Tuesday, May 15, 2007".
"*Cybergym Research LLC* v. *ICON Health & Fitness, Inc.*, (Case No. 2:05-CV-527):Deposition of Michael Gough on Feb. 7, 2007 (document not enclosed due to protections provided by Stipulated Protective Order issued by Judge David Folsom on May 15, 2006; however, a waiver of the Stipulated Protective Order protections has been requested from Paul Hickman of Cybergym Research, LLC)."
"*Cybergym Research LLC* v. *ICON Health & Fitness, Inc.*, (Case No. 2:05-CV-527):Icon's Motion and Memorandum for Summary Judgment of Non infringement of Claim 18 of the '537 Patent, signed by Charles L. Roberts on Jun. 1, 2007 (Document has been redacted to exclude ICON confidential information that is not material to patentability and which is protected by the Stipulated Protective Order issued by Judge David Folsom on May 15, 2006)."
"*Cybergym Research LLC* v. *ICON Health & Fitness, Inc.*, (Case No. 2:05-CV-527):Icon's Reply Brief in Further Support of its Motion for Summary Judgment of Noninfringement of Claim 18 of the '537 Patent, signed by Charles L. Roberts on Jun. 28, 2007."
"*Cybergym Research LLC* v. *ICON Health & Fitness, Inc.*, (Case No. 2:05-CV-527):Order regarding defendant's motion for summary judgment of claim 18 of the '537patent, signed by David Folsom on Sep. 4, 2007."
"*Cybergym Research LLC* v. *ICON Health & Fitness, Inc.*, (Case No. 2:05-CV-527):Plaintiff Cybergym Research LLC's Motion in Limine to Bar Testimony or Exhibits Relating to Prior Art That is Merely Cumulative to That Reviewed by the Examiner or Irrelevant, signed by William C. Milks, III on Sep. 7, 2007."
"*Cybergym Research LLC* v. *ICON Health & Fitness, Inc.*, (Case No. 2:05-CV-527):Defendant's Motion and Memorandum for Partial Summary Judgment of Invalidity under 35 U.S.C. §§ 102 (e) and 112, if 2 (Ulrich), signed by Charles L. Roberts on Jun. 1, 2007."
"*Cybergym Research LLC* v. *ICON Health & Fitness, Inc.*, (Case No. 2:05-CV-527):Order regarding the Defendant's Motion for Partial Summary Judgment of invalidity Under 35 U.S.C. §§ 102 (e) and 112, II 2 (Ulrich), signed by David Folsom on Sep. 4, 2007."
"*Cybergym Research LLC* v. *ICON Health & Fitness, Inc.*, (Case No. 2:05-CV-527):Defendant's Reply Brief in Further Support for its Motion for Summary Judgment of Invalidity (Ulrich), signed by Charles L. Roberts on Jun. 28, 2007."
"*Cybergym Research LLC* v. *ICON Health & Fitness, Inc.*, (Case No. 2:05-CV-527):Icon's Motion for Summary Judgment of No Direct Infringement, No Contributory Infringement, and to Limit the Damage Base for Induced Infringement, signed by Charles L. Roberts on Jun. 1, 2007 (Document has been redacted to exclude ICON confidential information that is not material to patentability and which is protected by the Stipulated Protective Order issued by Judge David Folsom on May 15, 2006)".
"*Cybergym Research LLC* v. *ICON Health & Fitness, Inc.*, (Case No. 2:05-CV-527):Defendant's Reply to Cybergym's Opposition to Icon's Motion for Summary Judgment of No Direct Infringement, No Contributory Infringement, and to Limit the Damage Base for Induced Infringement (Document has been redacted to exclude Icon confidential information that is not material to patentability and Which is protected by the Stipulated Protective Order issued by Judge David Folsom on May 15, 2006)".
"*Cybergym Research LLC* v. *ICON Health & Fitness, Inc.*, (Case No. 2:05-CV-527):Order regarding Defendant's Motion for Summary Judgment of No Direct Infringement, and to Limit the Damage Base for Induced Infringement, signed by David Folsom on Sep. 4, 2007."
"*Cybergym Research LLC* v. *ICON Health & Fitness, Inc.*, (Case No. 2:05-CV-527):Plaintiff Cybergym Research LLC's Notice of Motion and Motion for Partial Summary Judgment as to Icon Health & Fitness, Inc.'s Unenforceability Defense; Memorandum of Points and Authorities in Support Thereof, signed by Tim C. Hale on Jun. 1, 2007."
"*Cybergym Research LLC* v. *ICON Health & Fitness, Inc.*, (Case No. 2:05-CV-527):Icon's Opposition to Motion for Partial Summary Judgment as to Icon Health &Fitness, Inc.'s Unenforceability Defense; Memorandum of Points and Authorities in Support Thereof, signed by Charles L. Roberts on Jun. 18, 2007 (document not enclosed due to protections provided by Stipulated Protective Order issued by Judge David Folsom on May 15, 2006; however, a waiver of the Stipulated Protective Order protections has been requested from Paul Hickman of Cybergym Research, LLC)."
"*Cybergym Research LLC* v. *ICON Health & Fitness, Inc.*, (Case No. 2:05-CV-527):Defendant's Surreply in Further Opposition to Cybergym's Motion for Summary Judgment as to Icon's Unenforceability Defense, signed by Charles L. Roberts on Jul. 9, 2007."
"*Cybergym Research LLC* v. *ICON Health & Fitness, Inc.*, (Case No. 2:05-CV-527):Order regarding Plaintiff's Motion for Partial Summary Judgment as to Defendant's Unenforceability Defense, signed by David Folsom on Sep. 4, 2007."
"*Cybergym Research LLC* v. *ICON Health & Fitness, Inc.*, (Case No. 2:05-CV-527):Plaintiff Cybergym Research LLC's Notice of Motion and Motion for Partial Summary Judgment as to Defendant Icon Health & Fitness, Inc.'s Affirmative Defenses; Memorandum of Points and Authorities in Support Thereof signed by Tim C. Hale on Jun. 1, 2007."
"*Cybergym Research LLC* v. *ICON Health & Fitness, Inc.*, (Case No. 2:05-CV-527):Defendant's opposition to Cybergym's Motion for Partial Summary Judgment as to Defendant's Affirmative Defenses, signed by Charles L. Roberts on Jun. 18, 2007."
"*Cybergym Research LLC* v. *ICON Health & Fitness, Inc.*, (Case No. 2:05-CV-527): Defendant's Surreply in Further Opposition to Cybergym's Motion for Summary Judgment as to Icon's Affirmative Defenses, signed by Charles L, Roberts on Jul. 9, 2007."
"*Cybergym Research LLC* v. *ICON Health & Fitness, Inc.*, (Case No. 2:05-CV-527): Order regarding Plaintiff's Motion for Partial Summary Judgment as to Defendant's Affirmative Defenses, signed by David Folsom on Sep. 4, 2007."
"*Cybergym Research LLC* v. *ICON Health & Fitness, Inc.*, (Case No. 2:05-CV-527): Sealed Plaintiff Cybergym Research LLC's Response

(56) References Cited

OTHER PUBLICATIONS to Defendant Icon Health &Fitness, Inc.'s Motions for Summary Judgment, signed by William C. Milks, III onJun. 18, 2007 (document not enclosed due to protections provided by Stipulated Protective Order issued by Judge David Folsom on May 15, 2006;however, a waiver of the Stipulated Protective Order protections has been requested from Paul Hickman of Cybergym Research, LLC)."
"*Cybergym Research LLC* v. *ICON Health & Fitness, Inc.*, (Case No. 2:05-CV-527): Plaintiff Cybergym Research LLC's Consolidated Surreplies to Defendant Icon Health & Fitness, Inc.'s Replies to Oppositions by Plaintiff to Defendant's Motions for Partial Summary Judgment, signed by William C. Milks, III on Jul. 9, 2007."
"*Cybergym Research LLC* v. *ICON Health & Fitness, Inc.*, (Case No. 2:05-CV-527): Plaintiff Cybergym Research LLC's Consolidated Reply to Defendant Icon Health &Fitness, Inc.'s Responses to Cybergym's Motion for Summary Judgment, signed by William C, Milks, III, Jun. 28, 2007."
"*Cybergym Research LLC* v. *ICON Health & Fitness, Inc.*, (Case No. 2:05-CV-527): Joint Claim Construction and Prehearing Statement, signed by William C. Milks, III and Brett A. Hansen on Aug. 15, 2006."
"*Cybergym Research LLC* v. *ICON Health & Fitness, Inc.*, (Case No. 2:05-CV-527): Plaintiff Cybergym Research LLC's Preliminary Claim Constructions and Extrinsic Evidence, signed by William C. Milks, III on Jul. 20, 2006."
"*Cybergym Research LLC* v. *ICON Health & Fitness, Inc.*, (Case No. 2:05-CV-527): Icon Health & Fitness, Inc.'s Preliminary Constructions and Extrinsic Evidence signed by Brett A. Hansen on Jul. 20, 2006."
"*Cybergym Research LLC* v. *ICON Health & Fitness, Inc.*, (Case No. 2:05-CV-527): Plaintiff Cybergym Research LLC's Proposed Terms and Claim Elements for Construction, signed by William C. Milks, III on Jun. 30, 2006."
"*Cybergym Research LLC* v. *ICON Health & Fitness, Inc.*, (Case No. 2:05-CV-527): Icon Health & Fitness, Inc.'s Proposed Terms and Claim Elements for Construction, signed by Brett A. Hansen on Jun. 30, 2006."
"*Cybergym Research LLC* v. *ICON Health & Fitness, Inc.*, (Case No. 2:05-CV-527): Claim Construction Order regarding Plaintiff's Opening Claim Construction Brief, signed by David Folsom on Jan. 25, 2007."
"*Cybergym Research LLC* v. *ICON Health & Fitness, Inc.*, (Case No. 2:05-CV-527): Plaintiff Cybergym Research LLC's Reply Brief in Support of Claim Construction, signed by William C. Milks, III on Oct. 24, 2006."
"*Cybergym Research LLC* v. *ICON Health & Fitness, Inc.*, (Case No. 2:05-CV-527): Icon Health & Fitness, Inc.'s Claim Construction Brief, signed by Brett Hansen on Oct. 13, 2006."
"*Cybergym Research LLC* v. *ICON Health & Fitness, Inc.*, (Case No. 2:05-CV-527): Plaintiff Cybergym Research LLC's Opening Brief of Claim Construction, signed by William C. Milks, III on Oct. 2, 2006."
"*Cybergym Research LLC* v. *ICON Health & Fitness, Inc.*, (Case No. 2:05-CV-527): Reply to Defendant Icon Health & Fitness, Inc.'s Counterclaims, signed by Michael Smith and filed Mar. 9, 2006."
"*Cybergym Research LLC* v. *ICON Health & Fitness, Inc.*, (Case No. 2:05-CV-527): Answer and Counterclaims, signed by H. Craig Hall on Feb. 13, 2006."
"*Cybergym Research LLC* v. *ICON Health & Fitness, Inc.*, (Case No. 2:05-CV-527): Complaint for Patent Infringement and Willful Patent Infringement, signed by Carl R. Roth on Nov. 18, 2005."
"*Cybergym Research LLC* v. *ICON Health & Fitness, Inc.*, (Case No. 2:05-CV-527): Reply to Cybergym Research, LLC's Counterclaim, signed by Kirk Harris on Apr. 12, 2007."
"*Cybergym Research LLC* v. *ICON Health & Fitness, Inc.*, (Case No. 2:05-CV-527): Reply to Dick's Sporting Goods, Inc.'s First Amended Counterclaim, signed by Tim C. Hale on Apr. 6, 2007."
"*Cybergym Research LLC* v. *ICON Health & Fitness, Inc.*, (Case No. 2:05-CV-527): Reply to Sports Authority, Inc.'s First Amended Counterclaim, signed by Tim C. Hale on Apr. 6, 2007."
"*Cybergym Research LLC* v. *ICON Health & Fitness, Inc.*, (Case No. 2:05-CV-527): Reply to Sears, Roebuck and Co.'s First Amended Counterclaim, signed by Tim C. Hale on Apr. 6, 2007."
"*Cybergym Research LLC* v. *ICON Health & Fitness, Inc.*, (Case No. 2:05-CV-527): Reply to the Sports Authority, Inc.'s Counterclaim, signed by Tim C. Hale on Nov. 9, 2006."
"*Cybergym Research LLC* v. *ICON Health & Fitness, Inc.*, (Case No. 2:05-CV-527): Reply to Dick's Snorting Goods, Inc.'s Counterclaim, signed by Tim C. Hale on Nov. 9, 2006."
"*Cybergym Research LLC* v. *ICON Health & Fitness, Inc.*, (Case No. 2:05-CV-527): Reply to Cybergym Research, LLC's Counterclaim, signed by Kirk Harris on Nov. 22, 2006."
"*Cybergym Research LLC* v. *ICON Health & Fitness, Inc.*, (Case No. 2:05-CV-527): Reply to Sears, Roebuck and Co.'s Counterclaim, signed by Tim C. Hale on Nov. 9, 2006."
"*Cybergym Research LLC* v. *ICON Health & Fitness, Inc.*, (Case No. 2:05-CV-527): Reply and Counterclaim to Icon's Counterclaim, signed by Tim C. Hale on Nov. 2, 2006."
"*Cybergym Research LLC* v. *ICON Health & Fitness, Inc.*, (Case No. 2:05-CV-527): Answer to first Amended Complaint and Counterclaim, signed by Brett Hansen on Oct. 16, 2006."
"*Cybergym Research LLC* v. *ICON Health & Fitness, Inc.*, (Case No. 2:05-CV-527): First Amended Complaint for Patent Infringement and Willful Patent Infringement, signed by Michael Smith on Sep. 15, 2006."
"*Cybergym Research LLC* v. *ICON Health & Fitness, Inc.*, (Case No. 2:05-CV-527): Sports Authority's First Amended Answer to First Amended Complaint and First Amended Counterclaim, signed by Kirk Harris on Mar. 16, 2007."
"*Cybergym Research LLC* v. *ICON Health & Fitness, Inc.*, (Case No. 2:05-CV-527): Sears's First Amended Answer to First Amended Complaint and First Amended Counterclaim, signed by Kirk Harris on Mar. 16, 2007."
"*Cybergym Research LLC* v. *ICON Health & Fitness, Inc.*, (Case No. 2:05-CV-527): Dick's First Amended Answer to First Amended Complaint and First Amended Counterclaim, signed by Kirk Harris on Mar. 16, 2007."
"*Cybergym Research LLC* v. *ICON Health & Fitness, Inc.*, (Case No. 2:05-CV-527): Costco's First Amended Answer to First Amended Complaint, signed by Kirk Harrison Mar. 16, 2007."
Icon Health and Fitness, NordicTrack PT3 with FreeMotion Technology (Model No. NTSY9896.0), 2007. [in spec of U.S. Appl. No. 60/918,250].
eSpinner, http://www.startrac.com/US-en/cardio/detail.aspx?id=228, Feb. 23, 2011 (5.pp).
Office Action. U.S. Appl. No. 09/496,560. Feb. 22, 2001.
Notice of Allowance. U.S. Appl. No. 09/496,560, Oct. 22, 2001.
Notice of Allowance. U.S. Appl. No. 09/496,560. Apr. 8, 2002.
Office Action. U.S. Appl. No. 09/907,846. Jun. 25, 2004.
Notice of Allowance. U.S. Appl. No. 09/907,846. Feb. 4, 2005.
Petition Granted Notification. U.S. Appl. No. 09/907,846. Dec. 15, 2005.
Notice of Allowance. U.S. Appl. No. 09/907,846. Jan. 26, 2006.
Notice of Abandonment. U.S. Appl. No. 09/907,846. May 31, 2006.
Notice of Allowance. U.S. Appl. No. 10/674,911. Mar. 17, 2009.
Restriction Requirement. U.S. Appl. No. 10/916,687. Nov. 29, 2006.
Office Action. U.S. Appl. No. 10/916,687. Apr. 3, 2007.
Office Action. U.S. Appl. No. 10/916,687. Nov. 17, 2008.
Notice of Allowance. U.S. Appl. No. 10/916,687. Oct. 8, 2008.
Notice of Allowance. U.S. Appl. No. 10/916,687. Jun. 26, 2009.
Office Action. U.S. Appl. No. 11/113,921. Jul. 24, 2006.
Office Action. U.S. Appl. No. 11/113,921. Jun. 5, 2007.
Office Action. U.S. Appl. No. 11/113,921. Dec. 28, 2007.
Office Action. U.S. Appl. No. 11/113,921. Sep. 30, 2008.
Advisory Action. U.S. Appl. No. 11/113,921. Nov. 19, 2008.
Notice of Allowance. U.S. Appl. No. 11/113,921. Jan. 16, 2009.
Notice of Allowance. U.S. Appl. No. 11/113,921. Mar. 17, 2009.
Notice of Allowance. U.S. Appl. No. 11/113,921. Jun. 2, 2009.
Notice of Allowance. U.S. Appl. No. 11/113,921. Nov. 16, 2009.
Restriction Requirement. U.S. Appl. No. 11/314,133. Nov. 13, 2009.
Notice of Allowance. U.S. Appl. No. 11/314,133. Jun. 25, 2010.
Notice of Allowance. U.S. Appl. No. 11/315,682. Mar. 2, 2011.
Notice of Allowance. U.S. Appl. No. 11/315,682. Apr. 13, 2011.

(56) References Cited

OTHER PUBLICATIONS

Office Action. U.S. Appl. No. 12/413,330. Feb. 17, 2011.
Office Action. U.S. Appl. No. 12/413,330. Jul. 20, 2011.
Office Action. U.S. Appl. No. 12/413,330. Dec. 6, 2011.
Advisory Action. U.S. Appl. No. 12/413,330. Feb. 16, 2012.
Notice of Allowance. U.S. Appl. No. 12/413,330. May 10, 2012.
Office Action. U.S. Appl. No. 12/413,362. Feb. 3, 2011.
Notice of Allowance. U.S. Appl. No. 12/413,362. Apr. 15, 2011.
Notice of Allowance. U.S. Appl. No. 12/684,605. Jan. 18, 2011.
Notice of Allowance. U.S. Appl. No. 12/684,605. Feb. 23, 2011.
Notice of Allowance. U.S. Appl. No. 12/684,605. Mar. 21, 2011.
Office Action. U.S. Appl. No. 12/772,685. Dec. 21, 2010.
Notice of Allowance. U.S. Appl. No. 12/772,685. Apr. 4, 2011.
Restriction Requirement. U.S. Appl. No. 12/876,732. Feb. 13, 2013.
Notice of Allowance. U.S. Appl. No. 13/184,154. May 11, 2012.
Notice of Allowance. U.S. Appl. No. 13/184,154. Aug. 17, 2012.
Office Action. 90/011787. Sep. 1, 2011.
Determination ReExam Ordered. 90/011787. Sep. 1, 2011.
Office Action, 90/011787, Dec. 16, 2011.
Advisory Action. 90/011787. Mar. 1, 2012.
Intent to Issue. 90/011787, May 2, 2012.
Office Action. 90/011649. Aug. 22, 2011.
Granting Request for ReExam. 90/011649. Jun. 9, 2011.
Office Action. 90/011649. Dec. 16, 2011.
Advisory Action. 90/011649. Mar. 5, 2012.
Intent to Issue. 90/011649. May 4, 2012.
Action Closing Prosecution. 90/011649. Oct. 7, 2011.
Office Action Response. 90/011649. Aug. 8, 2011.
Office Action. 90/011649. Jun. 6, 2011.
Office Action. 95/001681. Sep. 28, 2011.
Determination ReExam Ordered. 95/001681. Sep. 28, 2011.
Action Closing Prosecution. 95/001681. Jun. 6, 2012.
The FitLinxx Interactive Fitness Network TM, Integrated Fitness Corp., brochure, 1998 (4 pages).
Fitlinxx Interactive Fitness Network TM, The Difference Between Surviving and Thriving May be as Simple as FitLinxx TM, Integrated Fitness Corp., brochure, 1998 (1 page).
Forbes Digital Tool: Startups, Sweat Equity, www.forbes.com, Feb. 1998 (2 pages).
Netpulse, Networkingout—Coming Distractions: Netpulse Helps Exercisers Surf the Net at the Gym, Accomplish Several Goals at Once, www.netpulse.com , Apr. 1998 (3 pages).
Netpulse, Instead of having an equipment repair technician traveling over hill and dale, you may soon have equipment repaired via the Internet, www.netpulse.com, Jul. 1998 (3 pages).
Netpulse, Infotech is supposed to make life easier—remember? Here's how to be sure it does, www.netpulse.com , Aug. 1998 (4 pages).
Netpulse, Exercise station connects to the Net, Now you can sweat to the Net, www.netpulse.com, Sep. 1998 (1 page).
Netpulse, New Fitness Equipment Combines Internet, Sweat, Now you can surf and sweat, www.netpulse.com, Jan. 1999 (2 pages).
Netpulse, Hop in, Log on and Sweat, Netpulse exercise machines are the latest Web feat, www.netpulse.com, Feb. 1999 (2 pages).
Netpulse Club Watch TM, Internet Powered Service, brochure, Apr. 1999 (1 page).
Netpulse, State of the Art, www.netpulse.com, Feb. 2000 (1 page).
Netpulse, Netpulse Files for Patents on its Pioneering Technology Inventions and Groundbreaking Business Methods in the Media and Fitness Markets, www.netpulse.com , May 2000 (2 pages).
Little Tony, One on One Video Trainer (for Model No. T1T123040), Jun. 1995 (25 pages).
Men's Journal, Squat.com. The Home Gym Goes Online, May 2000 (2 pages).
MSNBC.com, Smart Fitness Section, On a Quest for Fitness—The latest workout gear and Gadgets, Feb. 29, 2000 (6 pages).
OPTIONS Manual: Video Track/Track Five/Personal Trainer Plus (Part No. 109917) cited as "OPTIONS"), Sep. 1992 (4 pages).
PR Newswire, Turn Your Treadmill Into an Internet Appliance with www.ifit.com, Oct. 19, 1999 (3 pages).

PRO-FORM 8.0 TXP Manual (for Model No. PF080010) (cited as "8.0TXP"), Nov. 1991 (16 pages).
The Boston Globe, Living Section, p. F1, Wired Workout Local Gyms, Mar. 11, 2000 (2 pages).
The Herald Journal, People in Business, ICON wins Awards, vol. 91, No. 128, May 7, 2000 (1 page).
US Weekly, p. 71, Work Out Online, Mar. 27, 2000 (2 pages).
Communications of the ACM, vol. 35, No. 6, cited as "Comm of the ACM", Jun. 1992 (10 pages).
Ebsco Publishing, New home exercise equipment: your computer?, Jun. 2000 (3 pages).
Fortune Magazine. p. 84, Virtual Workouts—Treadmills Possessed, Apr. 17, 2000 (1 page).
Good House Keeping, p. 53, A Run for the Money, Feb. 2000 (2 pages).
IEEE Publication, A Telerobotics Construction Set with Integrated Performance Analysis, 0-8186-7108-4/95 (IEEE) (cited as "Telerobotic Con."), Apr. 1995 (7 pages).
IEEE Publication, Intelligent Monitoring System for Limited System for Limited Communication Path: Telerobotic Task Execution over Internet, 0-8186-7108-4/95 (IEEE) (cited as "Intelligent"), Apr. 1995 (6 pages).
Lifestyler 10.0 ESP Manual (for Model No. 297052) (cited as "10.0 ESP"), Nov. 1992 (16 pages).
1994 Pro-Form First in Fitness, (1994 Copyright ProForm Products, Inc.), (16 pages).
Consumer Reports, Out of the Rat Race, onto a Treadmill, Feb. 2000 (5 pages).
Consumer Reports, Out of the Rat Race, onto a Treadmill at http://www.accessmylibrary.com/coms2/summaryU0286-280045 14 ITM , Mar. 5, 2007, 8 pages.
Exergaming, en.wikipedia.org, printed Oct. 1, 2007 (4 pages).
WIRED, www.wired.com, issue 2.09, Sep. 1994 (4 pages).
"Defendant's Amended Invalidity Contentions," Case No. 2:05-cv-527, signed by Kirk Harris on Mar. 16, 2007 (15 pages).
"Icon Health & Fitness, Inc.'s Supplemental Preliminary Invalidity Contentions," Case No. 2:05-cv-527, signed by Brett A. Hansen on Jun. 23, 2006 (24 pages).
"Icon Health & Fitness, Inc.'s Preliminary Invalidity Contentions," Case No. 2:05-cv-527, signed by Brett A. Hansen on Jun. 26, 2006 (361 pages).
"Expert Report of Dr. Brent Nelson Pursuant to Federal Rule of Civil Procedure 26(a)(2)(B)," dated Mar. 13, 2007 (372 pages).
"Netpulse Brings Free Internet Access to Fitness Centers." Newsbytes.com, http://www.newsbytes.com, Jan. 17, 2000 (1 page).
"Precor and Netpulse Partner to Create the World's First Internet Powered Elliptical." Netpulse press release, Oct. 1, 1999 (2 pages).
"Surf While you Sweat." ABCNEWS.com , Oct. 27, 1998 (3 pages).
"The Best Products of 1999—Business Week's Top Picks of the Most Innovative Products on the Market." Business Week, Dec. 6, 1999 (2 pages).
Netpulse brochure. "Catch the wwwave," available on information and belief at least as early as Feb. 10, 2000 (6 pages).
Winkler, William J., "Pumping Iron With a Digital Friend," Business Week, Dec. 18, 1995, pp. 78a.
Internet Archive Wayback Machine archive for www. ifit.com , at http://web.archive.org/web/*/www.ifit.com , Sep. 1, 2003, 1 pg.
iFIT.com "Internet Workouts Control Your Treadmill, Bike, or Elliptical," at http://www.ifitcom , Sep. 1, 2003, 3 pages.
Icon Health and Fitness, Nordictrack C2420 (Model No. NLT 14950), 2004.
Icon Health and Fitness, Nordictrack C2420 (Model No. NTL 14951), 2004.
Icon Health and Fitness, Nordictrack C2420 (Model No. NLT 1495.2), 2004.
Icon Health and Fitness, Nordictrack CX 990 (Model No. NEL 09940), 2003.
Icon Health and Fitness, Nordictrack SL 760 (Model No. NTC 89021), 2004.
Icon Health and Fitness, Nordictrack SL 760 (Model No. NTC 89020), 2004.
Icon Health and Fitness, Nordictrack SL 710 (Model No. NTC 07942), 2004.

(56) References Cited

OTHER PUBLICATIONS

Icon Health and Fitness, Nordictrack SL 710 (Model No. NTC 07941), 2004.
Icon Health and Fitness, Nordictrack SL 710 (Model No. NTC 07940), 2003.
Icon Health and Fitness, Nordictrack SL 705 (Model No. NTC 05941) 2004.
Icon Health and Fitness, Nordictrack SL 705 (Model No. NTC 05940) 2004.
Icon Health and Fitness, Nordictrack C2420 Manual preceding Spec, 2004.
Icon Health and Fitness Pro-Form Personal Trainer Plus, available on information and belief at least as early as Jul. 2006.
Icon Health and Fitness, screenshots of iFit.com, available on information and belief at least as early as Jul. 2006.
Icon Health and Fitness, iFit.com "Log on. Work out," Brochure, 2000.
Icon Health and Fitness, Website printouts (archived docs), 2000.
Icon Health and Fitness, Pro-Form 600 (Model No. PETL60000), 2000.
Icon Health and Fitness Inc., Reebok ACD1 (Model No. RETL11900), 2000.
Icon Health and Fitness Inc., Reebok RT1000 (Model No. RETL16001), 2001. (26 pages).
Icon Health and Fitness Inc., One-on-One Video Trainer (Model No. TLTL21040), 1995.
IEEE Computer Graphics and Applications—EVAC: A Virtual Environment for Control of Remote Imaging Instrumentation, 1996.
IEEE: Performance Analysis of a Gateway Connecting the Cebus to the ISDN, 1993.
Fitness Equipment: Cardio, 1997.
ICON-CYB 034253-034286 and 034323-034328, containing photographs of various fitness equipment systems, 1989-1996, 40 pages.
Mademoiselle, www.IFIT.Com , Mademoiselle, Mar. 2000.
Wired, ICON Health & Fitness Image 10,4Qi, Wired, Apr. 2000.
Cooking Light, Cybertrainers are Watching Your Workout, Cooking Light, Aug. 2000.
Villarosa, A Fitness Industry, With Gadgets Galore, the New York Times, Apr. 25, 2000.
Little, Web Creates Workouts With Virtual Trainers, The Birmingham News, Apr. 10, 2000.
San Francisco Chronicle, Let the Web Help You Get Physical, Mar. 16, 2000.
"Workouts that Work," Consumer Reports, pp. 31-39, available on information and belief at east as early, as Jan. 1999, 9 pages.
New Balance Fitness Equipment advertisement, Runners World, Feb. 2006, 1 page.
New Balance Fitness Equipment advertisement (with sport block dumbbell advertisement), Runners World, Mar. 2006, 1 page.
T Series T3/75 Treadmill Operation Manual, copyright 2001, Life Fitness, 31 pages.
Advertisement, "We Just Made Buying a Trackmaster 100% Easier," Athletic Business, Oct. 1991, 2 pages.
Advertisement, "Trackmaster TM500E Treadmill Features Interactive Controller," Athletic Business, Oct. 1991, 1 page.
Advertisement, "Survival Equipment for the New Age," Athletic Business, Oct. 1991, p. 60.
Advertisement, "Introducing the LifeStep Model 9500—We've Made the Best Even Better," Athletic Business, Sep. 1991, 1 page.
Advertisement, "We Just Made Buying a Trackmaster 100% Easier," Athletic Business, Sep. 1991, 2 pages.
Trackmaster Online: Treadmill Controllers: http://web.archive.org/web/20010124093300/www.trackmastertreadmills.com/contrlr.html, available on information and belief at least as early as Jan. 2001, 1 page.
Transcript of Deposition of Michael Benjamin, taken Apr. 11, 2007, from *Cybergym Research, LLC* v. *Icon Health & Fitness, et al.*, in the Eastern District of Texas, Marshal Division, Case No. 2:05-cv-527 DF, 33 pages.
Michael Benjamin Computation Book, dated Nov. 2, 1991, 14 pages.

Tectrix Fitness Equipment, VR Bike Owner's Manual, Jan. 1995, 19 pages.
Tectrix Fitness Equipment, VR Bike Maintenance and Repair manual, Mar. 1997, 55 pages.
Tectrix Fitness Equipment, Photographs of VR Bike, available on information and belief at least as early as 1994, 15 pages.
Tectrix, Tectrix Fitness Equipment History, Jim Sweeney, Jun. 20, 1996, 4 pages.
Tectrix Fitness Equipment, Are We Having Fun Yet? brochure, 1995, 4 pages.
First for Women, No More Bicycle Boredom, Oct. 3, 1994, 2 pages.
Sports Illustrated, Software for Hardbodies, Sep. 19, 1994, 2 pages.
CyberGear, Inc., CyberGear 1000 brochure, which was available, on information and belief, at least as early as 1994, 2 pages.
National Fitness Trade Journal cover, Fall 1995, 1 page.
Tectrix Fitness Equipment, The Body the Brain the Passion the Will product brochure, circa 1998, 15 pages.
Leisure Management, Going Downhill, Virtually, vol. 14, No. 8, Aug. 1994, 2 pages.
Tectrix Fitness Equipment, Sweeney Town from CyberGear for the Tectrix VRBike brochure, which was available, on information and belief, at least as early as 1994, 2 pages.
"Virtual Treadmill Takes Users Anywhere They Want to Go," http://www.ksl.com/?nid=148&sid=6920538, Jun. 24, 2009, 2 pages.
Office Action. U.S. Appl. No. 08/766,513. Jun. 16, 1997.
Office Action. U.S. Appl. No. 08/766,513. Feb. 17, 1998.
Notice of Allowance. U.S. Appl. No. 08/766,513. Sep. 22, 1998.
Response to Rule 312. U.S. Appl. No. 08/766,513. Jun. 2, 1999.
Office Action. U.S. Appl. No. 09/273,591. Dec. 10, 1999.
Notice of Allowance. U.S. Appl. No. 09/27,3591. Jul. 14, 2000.
Office Action. U.S. Appl. No. 09/349,608. Sep. 11, 2000.
Notice of Allowance. U.S. Appl. No. 09/349,608. Jul. 25, 2001.
Office Action. U.S. Appl. No. 09/641,220. Dec. 18, 2001.
Notice of Allowance. U.S. Appl. No. 09/641,220. Jul. 1, 2002.
Restriction Requirement. U.S. Appl. No. 09/641,600. Sep. 23, 2003.
Office Action. U.S. Appl. No. 09/641,600. Feb. 11, 2004.
Notice of Allowance. U.S. Appl. No. 09/641,600. Jun. 2, 2004.
Office Action. U.S. Appl. No. 09/641,600. Feb. 15, 2005.
Notice of Allowance. U.S. Appl. No. 09/641,600. Sep. 14, 2005.
Notice of Allowance. U.S. Appl. No. 09/641,627. Sep. 20, 2004.
Restriction Requirement. U.S. Appl. No. 09/641,627. Apr. 29, 2005.
Office Adion. U.S. Appl. No. 09/641,627. Jul. 26, 2005.
Notice of Allowance. U.S. Appl. No. 09/641,627. Feb. 3, 2006.
Notice of Allowance. U.S. Appl. No. 09/641,627. Sep. 1, 2006.
Office Action. U.S. Appl. No. 09/690,178. Dec. 18, 2001.
Notice of Allowance. U.S. Appl. No. 09/690,178. Sep. 23, 2002.
Office Action. U.S. Appl. No. 09/690,178. Mar. 7, 2003.
Notice of Allowance. U.S. Appl. No. 09/690,178. Nov. 24, 2003.
Response to Rule 312. U.S. Appl. No. 09/690,178. Jan. 21, 2004.
Office Action . U.S. Appl. No. 09/690,701. Dec. 18, 2001.
Office Action. U.S. Appl. No. 09/69,0701. Sep. 25, 2002.
Office Action. U.S. Appl. No. 09/690,701. Mar. 26, 2003.
Advisory Action. U.S. Appl. No. 09/69,0701. Jun. 16, 2003.
Notice of Allowance. U.S. Appl. No. 09/690,701. Nov. 24, 2003.
Office Action. U.S. Appl. No. 09/776,410. Jun. 29, 2004.
Notice of Allowance. U.S. Appl. No. 09/776,410. Nov. 12, 2004.
Notice of Allowance. U.S. Appl. No. 09/776,410. Apr. 18, 2005.
Notice of Allowance. U.S. Appl. No. 09/933,701. Jun. 30, 2003.
Restriction Requirement. U.S. Appl. No. 09/947,193. Jul. 1, 2003.
Office Action. U.S. Appl. No. 09/947,193. Oct. 23, 2003.
Notice of Allowance. U.S. Appl. No. 09/947,193. May 14, 2004.
Office Action. U.S. Appl. No. 09/947,193. Sep. 15, 2005.
Notice of Allowance. U.S. Appl. No. 09/947,193. Jan. 26, 2006.
Notice of Allowance. U.S. Appl. No. 09/947,193. Aug. 16, 2006.
Office Action. U.S. Appl. No. 10/045,619. Jun. 15, 2004.
Notice of Allowance. U.S. Appl. No. 10/045,619. Mar. 14, 2005.
Restriction Requirement. U.S. Appl. No. 10/106,842. Sep. 21, 2004.
Office Action. U.S. Appl. No. 10/106,842. Nov. 12, 2004.
Notice of Allowance. U.S. Appl. No. 10/106,842. Mar. 14, 2005.
Restriction Requirement. U.S. Appl. No. 10/674,911. Aug. 22, 2006.
Office Action. U.S. Appl. No. 10/674,911. Dec. 12, 2006.
Restriction Requirement. U.S. Appl. No. 10/674,911. Jul. 2, 2007.
Office Action. U.S. Appl. No. 10/674,911. Nov. 28, 2007.

(56) References Cited

OTHER PUBLICATIONS

Office Action. U.S. Appl. No. 10/674,911. Apr. 22, 2008.
Office Action. U.S. Appl. No. 10/674,911. Aug. 18, 2008.
Notice of Allowance. U.S. Appl. No. 10/674,911. Jan. 28, 2009.
Restriction Requirement. U.S. Appl. No. 10/729,356. Dec. 29, 2004.
Office Action. U.S. Appl. No. 10/729,356. Feb. 16, 2005.
Restriction Requirement. U.S. Appl. No. 10/729,356. Feb. 21, 2006.
Notice of Allowance. U.S. Appl. No. 10/729,356. Jun. 13, 2006.
Response to Rule 312. U.S. Appl. No. 10/729,356. Jul. 30, 2007.
Office Action. U.S. Appl. No. 10/729,356. Jan. 14, 2008.
Office Action. U.S. Appl. No. 10/729,356. Jul. 1, 2008.
Notice of Allowance. U.S. Appl. No. 10/729,356. Mar. 19, 2009.
Office Action. U.S. Appl. No. 10/751,334. Jan. 27, 2005.
Office Action. U.S. Appl. No. 10/751,334. Aug. 25, 2005.
Notice of Allowance. U.S. Appl. No. 10/751,334. Jun. 12, 2006.
Restriction Requirement. U.S. Appl. No. 10/751,334. Apr. 17, 2007.
Restriction Requirement. U.S. Appl. No. 10/751,334. Aug. 9, 2007.
Office Action. U.S. Appl. No. 10/751,334. Jan. 25, 2008.
Office Action. U.S. Appl. No. 10/751,334. Jun. 2, 2008.
Office Action. U.S. Appl. No. 10/751,334. Nov. 25, 2008.
Notice of Allowance. U.S. Appl. No. 10/751,334. Jun. 1, 2009.
Office Action. U.S. Appl. No. 10/773,617. Jan. 24, 2005.
Notice of Allowance. U.S. Appl. No. 10/773,617. Apr. 17, 2006.
Notice of Allowance. U.S. Appl. No. 10/773,617. Jul. 6, 2006.
Office Action. U.S. Appl. No. 10/773,617. May 16, 2007.
Office Action. U.S. Appl. No. 10/773,617. Jan. 24, 2008.
Office Action. U.S. Appl. No. 10/773,617. Apr. 24, 2008.
Office Action. U.S. Appl. No. 10/773,617. Oct. 16, 2008.
Notice of Allowance. U.S. Appl. No. 10/773,617. May 29, 2009.
Restriction Requirement. U.S. Appl. No. 10/856,676. Oct. 9, 2007.
Office Action. U.S. Appl. No. 10/856,676. Jan. 24, 2008.
Office Action. U.S. Appl. No. 10/856,676. May 6, 2008.
Notice of Allowance. U.S. Appl. No. 10/856,676. Oct. 2, 2008.
Notice of Allowance. U.S. Appl. No. 10/856,676. Dec. 30, 2008.
Notice of Allowance. U.S. Appl. No. 10/856,676. Feb. 12, 2009.
Notice of Allowance. U.S. Appl. No. 10/856,676. Jul. 10, 2009.
Notice of Allowance. U.S. Appl. No. 10/856,676. Oct. 30, 2009.
Notice of Allowance. U.S. Appl. No. 11/132,740. Mar. 29, 2006.
Restriction Requirement. U.S. Appl. No. 11/150,914. Jul. 27, 2006.
Restriction Requirement. U.S. Appl. No. 11/150,914. Oct. 18, 2006.
Office Action. U.S. Appl. No. 11/150,914. Feb. 22, 2007.
Office Action. U.S. Appl. No. 11/150,914. Dec. 12, 2007.
Advisory Action. U.S. Appl. No. 11/150,914. Feb. 7, 2008.
Office Action. U.S. Appl. No. 11/150,914. Dec. 31, 2008.
Restriction Requirement. U.S. Appl. No. 11/150,914. Apr. 28, 2008.
Notice of Allowance. U.S. Appl. No. 11/150,914. Apr. 15, 2009.
Office Action. U.S. Appl. No. 11/150,914. Aug. 18, 2008.
Restriction Requirement. U.S. Appl. No. 11/143,133. Aug. 14, 2009.
Notice of Allowance. U.S. Appl. No. 11/314,133. Feb. 19, 2010.
Notice of Allowance. U.S. Appl. No. 11/314,133. May 10, 2010.
Notice of Allowance. U.S. Appl. No. 11/314,133. Jul. 29, 2010.
Office Action. U.S. Appl. No. 11/315,682. Jul. 16, 2009.
Office Action. U.S. Appl. No. 11/315,682. Sep. 29, 2009.
Notice of Allowance. U.S. Appl. No. 11/315,682. Feb. 19, 2010.
Notice of Allowance. U.S. Appl. No. 11/315,682. Apr. 21, 2010.
Notice of Allowance. U.S. Appl. No. 11/315,682. May 14, 2010.
Notice of Allowance. U.S. Appl. No. 11/315,681. Jun. 25, 2010.
Notice of Allowance. U.S. Appl. No. 11/315,682. Jul. 16, 2010.
Restriction Requirement. U.S. Appl. No. 11/429,725. Mar. 26, 2007.
Restriction Requirement. U.S. Appl. No. 11/429,725. Nov. 14, 2007.
Office Action. U.S. Appl. No. 11/429,725. Feb. 28, 2008
Notice of Allowance. U.S. Appl. No. 11/429,725. Jun. 4, 2008.
Notice of Allowance. U.S. Appl. No. 11/429,725. Sep. 8, 2008.
Notice of Allowance. U.S. Appl. No. 11/429,725. Jan. 30, 2009.
Notice of Allowance. U.S. Appl. No. 11/429,725. May 5, 2009.
Restriction Requirement. U.S. Appl. No. 11/429,858. Apr. 17, 2007.
Office Action. U.S. Appl. No. 11/429,858. Aug. 22, 2007.
Restriction Requirement. U.S. Appl. No. 11/429,858. Feb. 5, 2008.
Notice of Allowance. U.S. Appl. No. 11/429,858. Jun. 4, 2008.
Notice of Allowance. U.S. Appl. No. 11/429,858. Aug. 8, 2008.
Office Action. U.S. Appl. No. 11/440,703. Jun. 26, 2008.
Notice of Allowance. U.S. Appl. No. 11/440,703. Dec. 17, 2008.
Office Action. U.S. Appl. No. 11/657,701. Jun. 13, 2008.
Office Action. U.S. Appl. No. 11/657,701. Jan. 6, 2009.
Office Action. U.S. Appl. No. 11/657,701. Apr. 16, 2009.
Office Action. U.S. Appl. No. 11/657,701. Sep. 24, 2009.
Notice of Allowance. U.S. Appl. No. 11/657,701. Feb. 12, 2010.
Office Action. U.S. Appl. No. 11/833,070. Jun. 27, 2008.
Office Action. U.S. Appl. No. 11/833,070. Oct. 31, 2008.
Office Action. U.S. Appl. No. 11/849,068. May 1, 2008.
Office Action. U.S. Appl. No. 11/849,068. Aug. 21, 2008.
Office Action. U.S. Appl. No. 11/849,068. Dec. 10, 2008.
Office Action. U.S. Appl. No. 11/849,068. Apr. 16, 2009.
Office Action. U.S. Appl. No. 11/849,068. Mar. 12, 2010.
Notice of Allowance. U.S. Appl. No. 12/276,900. Jun. 18, 2009.
Notice of Allowance. U.S. Appl. No. 12/276,900. Nov. 2, 2009.
Office Action. U.S. Appl. No. 12/413,330. Sep. 2, 2010.
Restriction Requirement. U.S. Appl. No. 12/413,362. May 13, 2010.
Office Action. U.S. Appl. No. 12/413,362. Aug. 26, 2010.
Office Action. U.S. Appl. No. 12/467,776. Feb. 22, 2010.
Notice of Allowance. U.S. Appl. No. 12/467,776. Jun. 7, 2010.
Notice of Allowance. U.S. Appl. No. 12/467,776. Jul. 12, 2010 .
Notice of Allowance. U.S. Appl. No. 12/467,776. Sep. 21, 2010.
Office Action. U.S. Appl. No. 12/489,031. Apr. 20, 2010.
Notice of Allowance. U.S. Appl. No. 12/489,031. Sep. 30, 2010.
Restriction Requirement. U.S. Appl. No. 12/684,605. Jun. 29, 2010.
Office Action. U.S. Appl. No. 12/684,605. Sep. 1, 2010.
Restriction Requirement. U.S. Appl. No. 13/184,154. Feb. 21, 2012.
English Abstract and Machine Translation of EP 1683550. Jul. 26, 2006.
English Abstract and Machine Translation of CN 1162495 A. Oct. 22, 1997.
English Abstract and Machine Translation of CN 2449755 Y. Sep. 26, 2001.
English Abstract and Machine Translation of DE 41 00 559 A1, 2991/07/18.
English Abstract and Machine Translation of JP H10-243979. Sep. 14, 1998.
Information about Related Patents and Patent Applications, see the section below having the same title.

* cited by examiner

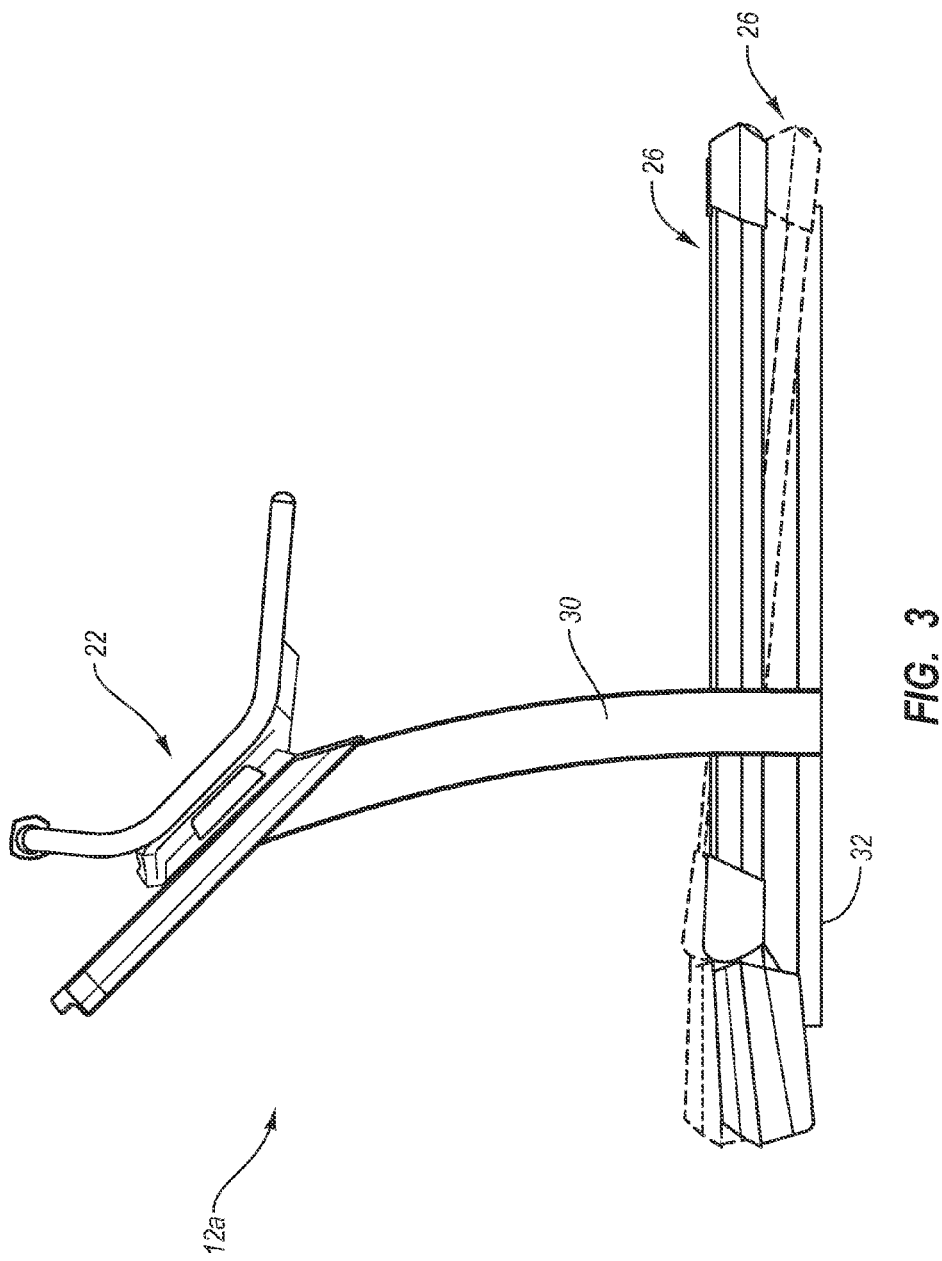

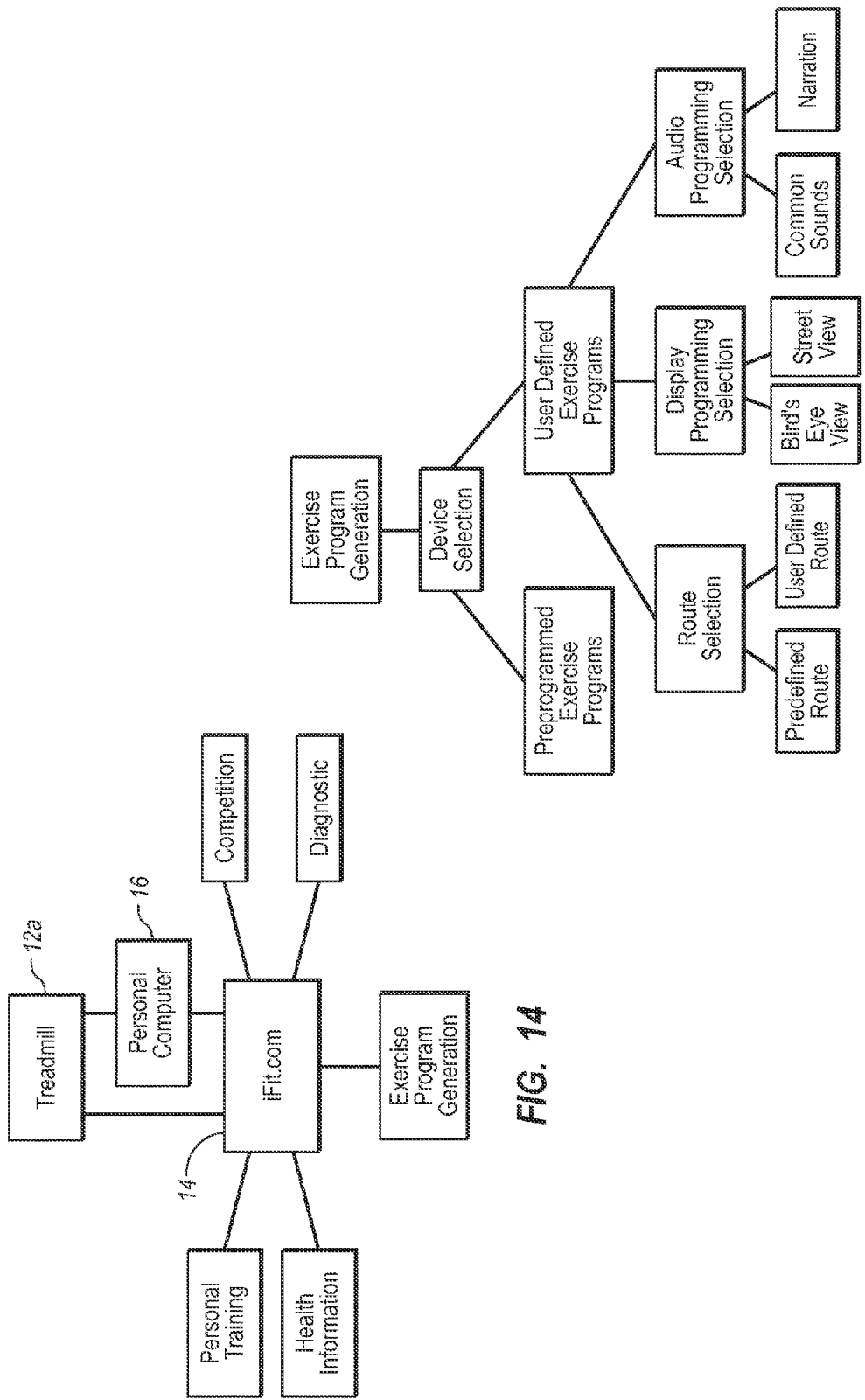

SYSTEMS, METHODS, AND DEVICES FOR SIMULATING REAL WORLD TERRAIN ON AN EXERCISE DEVICE

CROSS-REFERENCE TO RELATED APPLICATIONS

This application is a continuation of U.S. patent application Ser. No. 12/413,362, entitled "Systems, Methods, and Devices For Simulating Real World Terrain on an Exercise Device," filed Mar. 27, 2009, now U.S. Pat. No. 8,029,415, which is a continuation-in-part of U.S. patent application Ser. No. 11/849,068, entitled "Exercise Device with On Board Personal Trainer," filed Aug. 31, 2007, which claims priority to and the benefit of U.S. Provisional Application No. 60/918,250, entitled "Exercise Device with On Board Personal Trainer," filed Mar. 14, 2007. U.S. patent application Ser. No. 11/849,068 is also a continuation-in-part of each of: (1) U.S. patent application Ser. No. 10/916,687, entitled "Repetition Sensor in Exercise Equipment," filed Aug. 11, 2004, now U.S. Pat. No. 7,628,737 and (2) U.S. patent application Ser. No. 11/315,682, entitled "Methods and Systems for Controlling an Exercise Apparatus Using a Portable Data Storage Device," filed Dec. 21, 2005, now U.S. Pat. No. 7,985,164. U.S. patent application Ser. No. 11/315,682 is a continuation-in-part of U.S. patent application Ser. No. 10/856,676, entitled "Methods and Systems for Controlling an Exercise Apparatus Using a USB Compatible Portable Remote Device," filed May 28, 2004, now U.S. Pat. No. 7,628,830, which is a continuation-in-part of U.S. patent application Ser. No. 09/776,410, entitled "Methods and Systems for Controlling an Exercise Apparatus using a Portable Remote Device," filed on Feb. 2, 2001, now U.S. Pat. No. 6,997,852. U.S. patent application Ser. No. 09/776,410 is a continuation-in-part of each of: (a) U.S. patent application Ser. No. 09/641,220, entitled "Systems and Methods for Interaction with Exercise Device," filed on Aug. 18, 2000, now U.S. Pat. No. 6,458,060; (b) U.S. patent application Ser. No. 09/641,600, entitled "Computer Systems and Methods for Interaction with Exercise Device," filed Aug. 18, 2000, now U.S. Pat. No. 7,060,006; and (c) U.S. patent application Ser. No. 09/641,627, entitled "System for interaction with Exercise Device," filed Aug. 18, 2000, now U.S. Pat. No. 7,116,062. Each of U.S. patent application Ser. No. 09/641,220, filed on Aug. 18, 2000, U.S. patent application Ser. No. 09/641,600, filed Aug. 18, 2000, and U.S. patent application Ser. No. 09/641,627, filed Aug. 18, 2000, is a continuation-in-part of each of: (1) U.S. patent application Ser. No. 09/496,560, entitled "System and Method for Selective Adjustment of Exercise Apparatus," filed on Feb. 2, 2000, now U.S. Pat. No. 6,447,424, and (2) U.S. patent application Ser. No. 09/349,608, entitled "Systems and Methods for Providing an Improved Exercise Device with Motivational Programming," filed on Jul. 8, 1999, now U.S. Pat. No. 6,312,363. U.S. patent application Ser. No. 12/413,362 is also a continuation-in-part of U.S. patent application Ser. No. 11/429,725, entitled "Systems and Methods for Enabling Two-Way Communication Between One or More Exercise Devices and Computer Devices and for Enabling Users of the One or More Exercise Devices to Competitively Exercise," filed May 8, 2006, now U.S. Pat. No. 7,556,590, which is a divisional of U.S. patent application Ser. No. 09/947,193, entitled "Systems and Methods for Enabling Two-Way Communication Between One or More Exercise Devices and Computer Devices and for Enabling Users of the One or More Exercise Devices to Competitively Exercise," filed Sep. 5, 2001, now U.S. Pat. No. 7,166,064. U.S. patent application Ser. No. 09/947,193 is a continuation-in-part of each of: (a) U.S. patent application Ser. No. 09/641,600, entitled "Computer Systems and Methods for Interaction with Exercise Device," filed Aug. 18, 2000, now U.S. Pat. No. 7,060,006; (b) U.S. patent application Ser. No. 09/641,220, filed Aug. 18, 2000, entitled "Systems and Methods for Interaction with Exercise Device;" and (c) U.S. patent application Ser. No. 09/641,627, filed Aug. 18, 2000, entitled "System for Interaction with Exercise Device." Each of U.S. patent application Ser. No. 09/641,600, filed on Aug. 18, 2000, U.S. patent application Ser. No. 09/641,220, filed Aug. 18, 2000, and U.S. patent application Ser. No. 09/641,627, filed Aug. 18, 2000, is a continuation-in-part of each of: (i) U.S. patent application Ser. No. 09/496,560, entitled "System and Method for Selective Adjustment of Exercise Apparatus," filed on Feb. 2, 2000, now U.S. Pat. No. 6,447,424; and (ii) U.S. patent application Ser. No. 09/349,608, entitled "Systems and Methods for Providing an Improved Exercise Device with Motivational Programming," filed on Jul. 8, 1999, now U.S. Pat. No. 6,312,363. U.S. patent application Ser. No. 12/413,362 is also a continuation-in-part of U.S. patent application Ser. No. 10/674,911, entitled "Systems and Methods for Controlling the Operation of One or More Exercise Devices and Providing Motivational Programming," filed Sep. 29, 2003, now U.S. Pat. No. 7,537,546. U.S. patent application Ser. No. 10/674,911 is a continuation-in-part of U.S. patent application Ser. No. 09/933,701, entitled "System And Methods For Providing An Improved Exercise Device With Motivational Programming," filed Aug. 20, 2001, now U.S. Pat. No. 6,626,799, which is a continuation of U.S. patent application Ser. No. 09/349,608, filed Jul. 8, 1999, entitled Systems and Methods for Providing an Improved Exercise Device with Motivational Programming," now U.S. Pat. No. 6,312,363. U.S. patent application Ser. No. 10/674,911 is also a continuation-in-part of U.S. patent application Ser. No. 09/641,627, filed Aug. 18, 2000, entitled "System for Interaction with Exercise Device," now U.S. Pat. No. 7,116,062. U.S. patent application Ser. No. 09/641,627, filed Aug. 18, 2000, is a continuation-in-part of each of: (i) U.S. patent application Ser. No. 09/349,608, filed Jul. 8, 1999, entitled "Systems and Methods for Providing an Improved Exercise Device with Motivational Programming," now U.S. Pat. No. 6,312,363, and (ii) U.S. patent application Ser. No. 09/496,560, filed Feb. 2, 2000, entitled "System and Method for Selective Adjustment of Exercise Apparatus," now U.S. Pat. No. 6,447,424. Each of the aforementioned applications and patents is hereby incorporated herein in its entirety by reference.

BACKGROUND OF THE INVENTION

1. The Field of the Invention

The present invention relates to exercise equipment. More specifically, the invention relates to methods, systems, and devices for selective adjustment of an exercise device to simulate movement along real world terrain.

2. The Relevant Technology

In an attempt to improve their health and physical conditioning, consumers are purchasing exercise devices in record quantities. One common challenge with exercise equipment is motivating the purchaser to use the device on a consistent and ongoing basis. This lack of motivation can be a result of the repetitive nature of the exercises and exercise routines that a user can perform on a specific exercise device as well as the versatility of the exercise devices.

With a typical stationary exercise cycle, for example, a user sits on a seat, holds onto one or more handles, and pedals with his or her feet. In order to provide variety during the exercise routine, the user can increase or decrease his or her pedaling rate at various times during the exercise routine. This can be done by increasing or decreasing the amount of effort the user uses to pedal or by increasing or decreasing the pedaling resistance provided by the exercise cycle. Additionally, many stationary exercise cycles are pre-programmed with one or more exercise routines that automatically adjust the pedaling resistance at various time intervals during the exercise routine. Adjusting the pedaling rate and/or the pedaling resistance can allow a user to achieve a workout suitable for the user's fitness level and goals. Adjusting the pedaling rate and/or the pedaling resistance, however, is often insufficient to maintain a user's motivation to consistently use the stationary exercise cycle.

Typical treadmills also allow a user to adjust various operating parameters to provide for improved workouts and variety during the workouts. As with the stationary exercise cycles, however, users are typically limited as to which treadmill operating parameters can be adjusted. For instance, treadmills usually provide for the adjustment of the speed and incline of the endless belt upon which the user ambulates. This allows a user to walk, jog, and/or run on the treadmill. It also allows the user to ambulate on a level surface or on an inclined surface that generally replicates a hill. These adjustable operating parameters are, like those of the stationary exercise cycles, often insufficient to motivate a user to consistently use the treadmill on an ongoing basis.

Another factor that contributes to the lack of motivation to use exercise devices is the lack of visual or other type of stimulation provided to the user while using the exercise device. In other words, users of exercise devices often become bored because their surroundings do not change during an exercise routine. Rather, their surroundings (i.e., the room in which the exercise device is located) are generally the same each time the user exercises and throughout each exercise session. This boredom can discourage the user from regularly using the exercise device. Even when the user does use the exercise device, the boredom resulting from the lack of stimulation can cause the user to not work as hard during the exercise session, which can hamper the user's ability to achieve his or her fitness goals.

In order to combat this lack of stimulation, many exercise devices are equipped with a display for providing visual stimulation and motivation to the user of the device. For example, some displays depict a tract for indicating to a user how far the user has run or pedaled. Similarly, some displays depict hills that provide a visual representation of the resistance or inclination of the device. For instance, the display of a stationary exercise cycle may depict a series of hills that are related to the pedaling resistance of the exercise cycle. As the user "rides up the hill," the pedaling resistance will increase; the steeper the hill, the greater the pedaling resistance will be. Correspondingly, as the user "rides down the hill," the pedaling resistance will decrease. While these types of displays may provide some visual stimulation to the user, most users will quickly become bored with such displays, and the desired stimulatory benefits will not be realized. In contrast, when a person goes outside for a walk, run, or bicycle ride, the person's surroundings are constantly changing, which can provide sufficient stimulation to the person's mind to keep them motivated throughout the exercise routine.

BRIEF SUMMARY OF THE INVENTION

The present invention relates to exercise equipment and systems, and particularly to methods, systems, and devices for selective adjustment of an exercise device to simulate movement along real world remote locations while displaying images/videos of the remote locations. Simulation of a remote, real world locations and display of the related images provides a user of the exercise device with the greater interest and motivation to use the exercise device on a regular and ongoing basis. The simulation also allows the user to experience is a very real sense what it is like to traverse the remote location.

Thus, according to exemplary embodiments of the invention, an exercise system includes one or more exercise devices that communicate via a network with a communication system, such as a website. The communication system stores and/or generates exercise programming for use on the exercise device. The exercise programming is able to control one or more operating parameters of the exercise device to simulate terrain found at a remote, real world location. The exercise programming can also include images/videos of the remote, real world location. The control signals and the images/videos can be synchronized so that a user of the exercise device is able to experience, via the changing operating parameters, the topographical characteristics of the remote, real world location as well as see images of the location.

In one embodiment of the present invention, the exercise system includes an exercise device that has a movable element for movement in performance of exercise by a user and at least one actuator for controlling one or more operating parameters of the exercise device. The exercise device is able to receive exercising programming that causes the exercise device to simulate one or more aspects of a remote, real world exercise route. The exercise programming can include one or more control signals representative of changes to be made to the one or more operating parameters to simulate the remote, real world exercise route. In some embodiments, the exercise programming includes display programming that display images of the remote, real world exercise route to the user. The control signals and the display programming can be synchronized with one another to enhance the simulated experience.

The exercise system also includes a remote communication system that uses data relating to the remote, real world exercise route to generate the exercise programming which will cause the exercise device to simulate the one or more aspects of the remote, real world exercise route. The data used to generate the exercise programming can include map data, topographical data, video or image data, or a combination thereof. The data used to generate the exercise programming can be obtained from one or more databases, such as one or more websites. One database, for example, may store topographical data while another database stores image data. The remote communication system can be configured to access the data from one or more of the databases and synchronize the data to generate the exercise programming. The system also includes a network adapted to facilitate communication between the remote communication system and the databases as well as facilitating communication of the exercise programming from the remote communication system to the exercise device.

According to another embodiment, the exercise system includes an exercise device that has a movable element for movement in performance of exercise by a user. The exercise device can also have one or more operating parameters that are controlled by exercise programming. A remote communication system can be adapted to communicate with a user of the exercise device and generate the exercise programming that is communicated to the exercise device. The remote communication system enables the user to create user defined exercise programming by allowing the user to select a starting point and an ending point for the remote, real world exercise route. As above, the exercise programming can include one or more control signals representative of changes to be made to the one or more operating parameters to simulate topographical characteristics of the remote, real world exercise route, and display programming including images of the remote, real world exercise route. The exercise system can also include a network that communicates with the exercise device and the remote communication system to communicate the exercise programming from the remote communication system to the exercise device.

In one embodiment, the exercise device is a treadmill that has a base frame, a treadbase mounted on the base frame, and an endless belt trained around the treadbase to enable the user to ambulate thereon. The treadbase can be pivotally mounted on the base frame so that the treadbase can be selectively inclined or declined to simulate for the user the experience of ambulating up and down hills of a remote, real world exercise route. Similarly, the treadbase can be pivotally mounted on the base frame so that the treadbase can be selectively tilted from one side to the other side to simulate for the user the experience of ambulating on an uneven surface of a remote, real world exercise route.

In another embodiment, the exercise device is an exercise cycle. The exercise cycle includes a support base adapted to rest upon a support surface and an upright support structure mounted to the support base. The upright support structure includes a seat, a handle bar assembly, and a control panel. The exercise cycle also includes a pedal assembly that can be engaged and rotated by a user's feet. A resistance assembly provides resistance to the rotation of the pedal assembly and can be controlled by one or more control signals of the exercise programming. According to some embodiments, the upright support structure is pivotally mounted to the support base so that the upright support structure can be selectively tilted forward or backward to simulate for the user the experience of riding a bicycle up or down a hill.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which:

FIG. 3 is a side illustration of a the treadmill of FIG. 2 with the treadbase shown in a neutral position, and an inclined position featured in phantom view;

FIG. 14 is a functional block diagram of the process of connecting to a remote communication system and selecting one or more options available from the remote communication system;

FIG. 15 is a flow diagram representing the actions performed by the user and communication module to create exercise programs in accordance with the teachings of the present invention;

DETAILED DESCRIPTION OF THE PREFERRED EMBODIMENTS

The present invention is directed to devices that include one or more motors or other electrically driven actuators used to control one or more operating parameters of the device. While the invention will be described in the context of either a motorized treadmill or a stationary exercise cycle, it should be understood that the invention is not limited to any particular type of exercise device. To the contrary, the present invention can be readily adapted to any motorized device or any other device that utilizes motors, solenoids, or any other electrically driven actuators to control any operating parameter of the device, such as speed, resistance, incline, time, temperature, or other similar operating parameters. The term "device" or "devices" shall refer broadly to any type of apparatus that includes one or more stepper motors, solenoids, or other electrically driven actuators or controllers. Additionally, the term "exercise devices" shall refer broadly to any type of device that takes the form of an exercise machine, including, but not limited to, treadmills, exercise cycles, Nordic style ski exercise devices, rowers, steppers, hikers, climbers, and elliptical or striding exercise devices.

Figure 1:
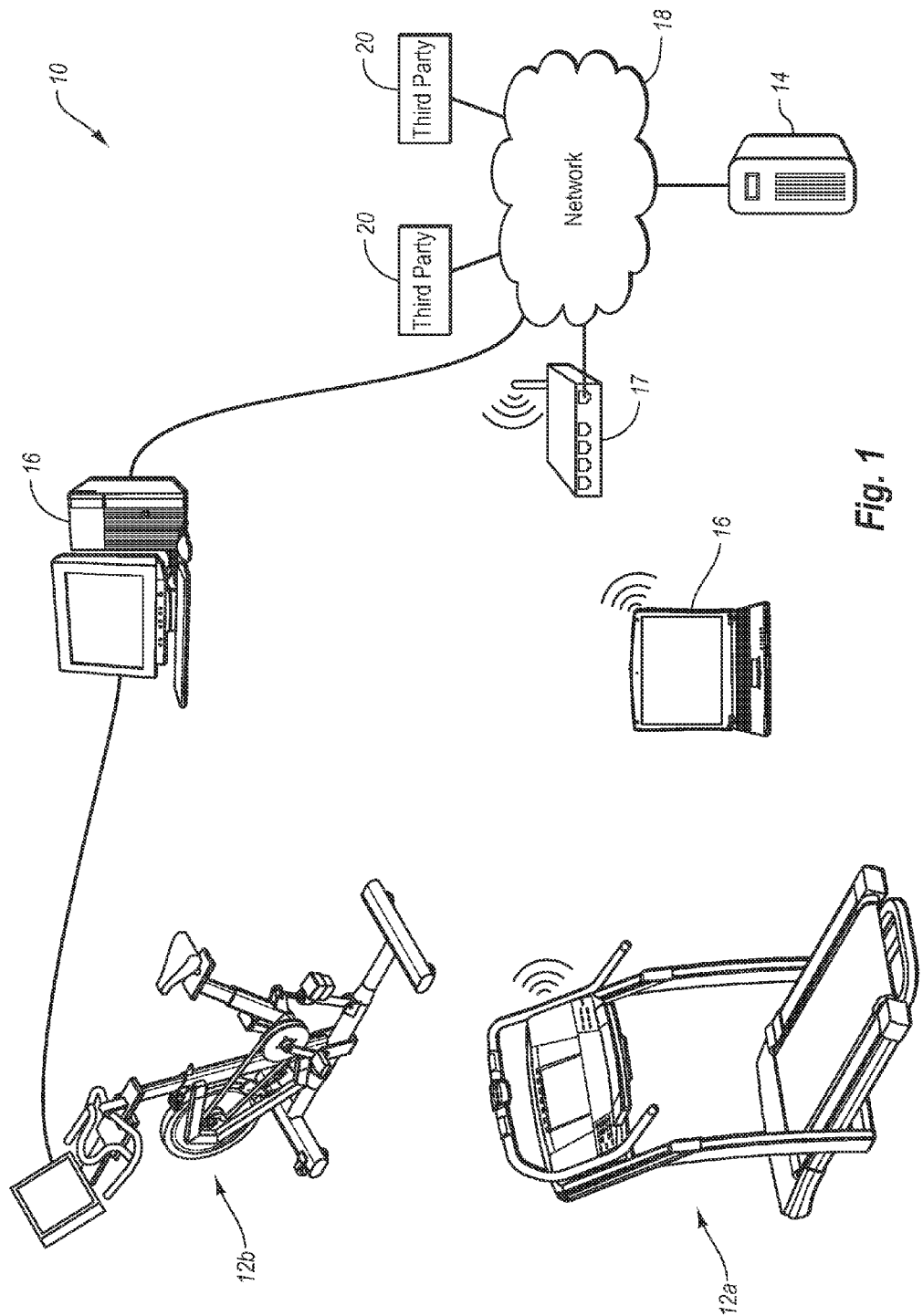
FIG. 1 illustrates an exemplary exercise system according to the present invention.

Depicted in FIG. 1 is a representation of one illustrative system, designated by reference numeral 10, which may incorporate the novel features of the present invention, including various novel devices, hardware and software modules, and the like. As shown, one or more exercise mechanisms 12, such as a treadmill 12a and an exercise cycle 12b are each in communication with a communication system 14

(e.g. a website) via a personal computer 16. The personal computers 16 communicate with a network 18 that is a communication network that enables various hardware and software modules and devices to communicate one with another. Network 18, therefore, may be a local area network (LAN), wide area network (WAN), wireless network, packetized network, real-time network, and the like. Network 18 facilitates communication of treadmill 12a and/or exercise cycle 12b with communication system 14. Communication system 14 assists with communication between a user on treadmill 12a and/or exercise cycle 12b and one or more third parties 20, as will be described in more detail hereinafter.

In the illustrated embodiment, connection between the exercise mechanisms 12 and network 18 can be made via a variety of communication line connections. For example, as depicted in FIG. 1, treadmill 12a is capable of wireless communication with network 18, either directly or via computer 16 and/or wireless router 17. Various other types of ports or interfaces may be included within exercise mechanisms 12 to enable communication via one or more communication line connections. For instance, an exercise mechanism 12 may include one or more ports and interfaces to enable communication line connection through existing broadcast technology, including television broadcast over the airwaves, cable or cable modems, satellite, telephone lines, whether analog or digitally based, the Internet, DSL, G-Lite, wireless technology, infra-red (IR) technology, other high-speed data connections, or any other suitable transmission technology or medium. In the illustrated embodiment, exercise cycle 12b is shown with a hardwire connection to personal computer 16, which has a hardwire connection with network 18. Thus, system 10 may allow for any type of connection between an exercise mechanism 12 and network 18, whether wired or wireless.

Although each exercise mechanism of system 10 is depicted as communicating via a personal computer 16 and network 18 with a single communication system 14 and two third parties 20, it may be appreciated by one skilled in the art that system 10 may be otherwise configured. For example, treadmill 12a and exercise cycle 12b may communicate via the same personal computer 16. Similarly, the exercise devices may communicate with multiple communications systems 14 and third parties 20 via multiple networks 18. Alternatively, one or more of the elements of system 10 may be eliminated or the functionality thereof incorporated within the structure and function of one or more of the other elements of system 10.

Similarly, although each of the elements of system 10 are shown separated one from another, it may be appreciated by one skilled in the art that the hardware and/or software elements of the present invention may be incorporated within two or more elements. For example, personal computers 16 may be incorporated within treadmill 12a and/or exercise cycle 12b. Similarly, the hardware and/or software elements of the communication system 14 may be incorporated within treadmill 12a and/or exercise cycle 12b.

As used herein, a database that is "external to" or "remote from" communication system 14 refers to a database that is administered or maintained by a third party 20 that is different than the entity that administers or maintains communication system 14. Generally, examples of a third party 20 may include: (i) a live human being; or (ii) a database, such as a website, computer, optical media (e.g., compact disk or digital video disk), visual media, or magnetic media (e.g., videotape, readable disk), an electronic monitoring system, dynamic computer readable instructions, interactive and/or dynamic software programs, computer readable instructions, one or more other databases, other media, hardware, and/or software modules and components that is/are located external to communication system 14. In some embodiments, a third party 20 may include MAPQUEST.COM, MAP.GOOGLE.COM, the GOOGLE EARTH database, the GTOPO 30 database, the GOOGLE STREET VIEW database, the MICROSOFT VIRTUAL EARTH database, and the like. These third parties are examples of databases that store data external to communication system 14.

Such databases store image data that can be displayed or can be formatted or manipulated to be displayed on a display device 152 of an exercise device 12. The term "image data" includes and/or is representative of: i) one or more static images; and/or ii) one or more moving (i.e., video) images. For example, image data as used herein may include a plurality of sequential static images, a video display, and/or a single image of terrain to be traversed by a user, such as a mountain, race course, or street.

Furthermore, the phrase "display programming," as used herein, includes image data and/or image data that has been formatted or manipulated so that it can be synchronized with control signals and/or displayed on a display device of an exercise device. Examples of such display programming that can display images on display 152 include video programming, sequential static image programming, and/or a single image of terrain to be traversed, for example.

The majority of the discussion of system 10 will focus on the use and interaction of treadmill 12a with system 10. However, exercise cycle 12b will also be described in connection with FIGS. 10 through 12. While system 10 will be described primarily in connection with treadmill 12a, it may be appreciated that a similar discussion may be had for exercise cycle 12b, other types of exercise mechanisms, or multiple exercise mechanisms of the same or different type. Thus, as illustrated in FIG. 1, exercise cycle 12b may be used in connection with system 10 along with most of the features described in connection with treadmill 12a.

Generally, system 10 enables exercise programming with control signals to be transmitted from communication system 14, to a user at treadmill 12a. As disclosed in U.S. patent Ser. No. 09/349,608 entitled "Systems and Methods for Providing an Improved Exercise Device with Motivational Programming," which is incorporated herein by reference, the programming may include motivational content and/or one or more control signals that may be used to control the operating parameters of treadmill 12a. The control signals may be synchronized with the motivational content and designed to control one or more operating parameters of the exercise device, such as the speed, incline, difficulty of exercise program, time, distance, and the like of an exercise program performed on treadmill 12a.

As used herein, the term "motivational content" is used to broadly refer to any video or visual material either alone or in combination with audio material, including dialog, narration, sound effects, and/or music. In one embodiment of the present invention, the motivational content is stored by a third party 20 and includes images, whether still or moving, of real world environments, routes, locations, and the like.

Various terms are used herein to describe actual outdoor exercise experiences that can be simulated on treadmill 12a, or another exercise device. These terms include real world environments, places, routes, trails, paths, courses, hikes, locations, and the like. It will be appreciated that these terms are used to broadly refer to characteristics of actual places in the world, including the topography, appearance, and sounds associated with the real world places. Additionally, exercise system 10 is described as being able to simulate these real world places. Simulating these real world places refers to providing a user of an exercise device an experience that is similar to actually being in the real world places. In other words, system 10 is adapted to replicate on an exercise device the topography, sights, and/or sounds that a person would experience were the person to actually to walk, run, ride, or the like, through the actual real world location.

Generally, communication between treadmill 12a and communication system 14 and/or a third party 20 may include both the motivational content and the control signals, whether or not such control signals are synchronized with the motivational content. Alternatively, the communication may include only the motivational content, other signals representative of measurable parameters of the exercise device (e.g. speed, inclination, resistance, etc) and/or a user of the exercise device (e.g. heart rate, blood pressure, etc), and the like. For example, treadmill 12a may transmit one or more signals to communication system 14. The signal may include parameters such as the status of the exercise device, e.g., active status (i.e., on), deactivated status (i.e., off), standby status (i.e., waiting), and the like, and/or parameters such as speed, inclination, resistance. Additionally, the signal may include parameters regarding the user, such as heart rate, blood pressure, and the like. Alternatively, treadmill 12a may receive programming "broadcast" by communication system 14, such that any treadmill with the capabilities to receive the programming may access such, without the need to transmit one or more signals.

As mentioned above, the control signals control the operating parameters of treadmill 12a, such as speed, inclination, resistance, and the like. Such control may be achieved by communication system 14, or a combination of communication system 14 and a third party 20 interacting with treadmill 12a and/or communication system 14. Generally, the present invention allows control of a device, such as an exercise device, without the need to interrupt the other portions of the programming, such as the real-time audio and/or video.

FIGS. 2 through 9 generally depict a typical motorized treadmill 12a that can be used in connection with system 10. Treadmill 12a, in one embodiment, includes a control panel 22 supported on a generally upright support structure 24 and a treadbase 26. Upright support structure 24, in this illustrative embodiment, includes two side members 28, 30 coupled to a base frame 32. Side members 28, 30 and base frame 32 may have various configurations and may be fabricated from various materials so long as they are capable of supporting control panel 22 and treadbase 26. For example, the elements of upright support structure 24 and base frame 32 may be fabricated from, but not limited to metals, plastics, composites, combinations thereof, and the like. Additionally, one skilled in the art may appreciate that various other exercise devices may have different upright support structures, side members, and base frames, or be devoid of one or more of such structures and members.

The treadbase 26 typically includes a pair of side rails 34, 36 each having a front portion proximal to and a rear portion distal from upright support structure 24. A front pulley 38 (FIG. 6) and a rear pulley 40 (FIG. 6) are disposed between and supported by side rails 34, 36, while a continuous belt 42 extends between and around front and rear pulleys 38 and 40, respectively. Pulleys 38, 40 and belt 42 may have various configurations and be fabricated from various materials, as known by one skilled in the art and commonly known within the exercise industry.

A deck 44, commonly fabricated from wood, typically supports the upper run of belt 42 and supports an exercising individual positioned upon belt 42. Although deck 44 is preferably of a cellulose material such as wood, various other types of material may be used so long as deck 44 is capable of supporting belt 42 and a user exercising thereupon.

As is common with electric treadmills, such as treadmill 12a, front pulley 38 is mechanically coupled to an electric tread drive motor 46 (not shown) by way of a drive belt 48 (not shown). Motor 46 can incorporate an inertial flywheel that controls fluctuations in the rotational motion of a shaft of motor 46 during operation of treadmill 12a. Motor 46 is optionally electrically coupled to a treadmill controller 50 (not shown) that controls the operation of motor 46, and thus the speed of belt 42, in response to various user inputs or other control signals. Treadmill controller 50 can be incorporated within treadbase 26, control panel 22, or within personal computer 16.

In addition to the ability to control and vary the speed of belt 42, treadmill 12a also permits the degree of incline of treadbase 26 relative to the floor, or other surface upon which treadbase 26 rests, to be varied. As depicted in FIG. 3 in solid lines, treadbase 26 can be oriented in a neutral position. In the neutral position, treadbase 26 is substantially parallel to a support surface. Additionally, as illustrated in phantom lines in FIG. 3, treadbase 26 can be oriented in an inclined position such that the front portion of treadbase 26 is above the neutral position. This enables an exerciser to simulate walking or running up a hill.

In one embodiment, treadbase 26 can also be configured to decline into a declined position in which the front portion of treadbase 26 drops below the neutral position. Typical walks or runs outside, for example, involve inclines and declines as well as flat surfaces, each of which can be accommodated and replicated by treadbase 26. Thus, treadmill 12a is able to more closely simulate typical outdoor terrain.

Figure 6:
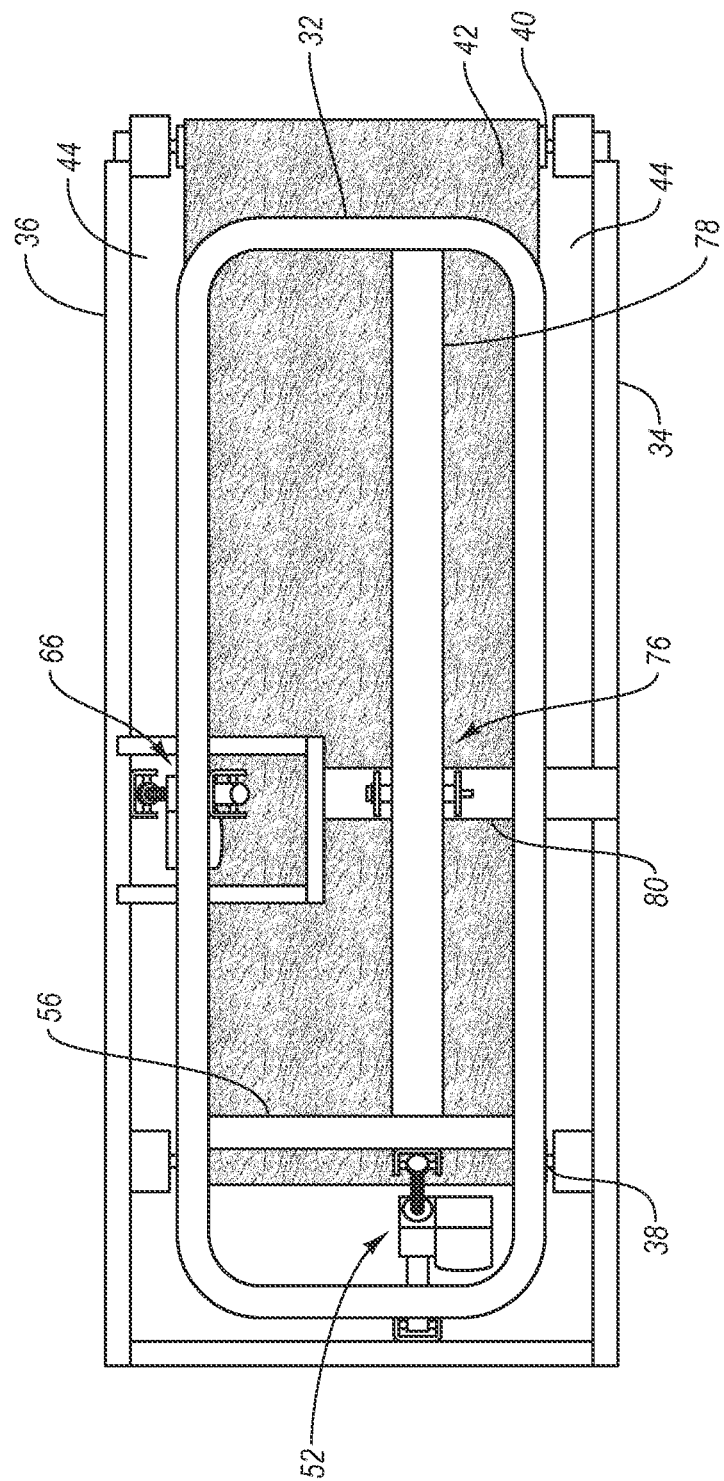
FIG. 6 is a bottom view of the treadmill illustrated in FIGS. 2 through 5 showing some of the incline/decline and tilting mechanisms of the treadmill.
Figure 7:
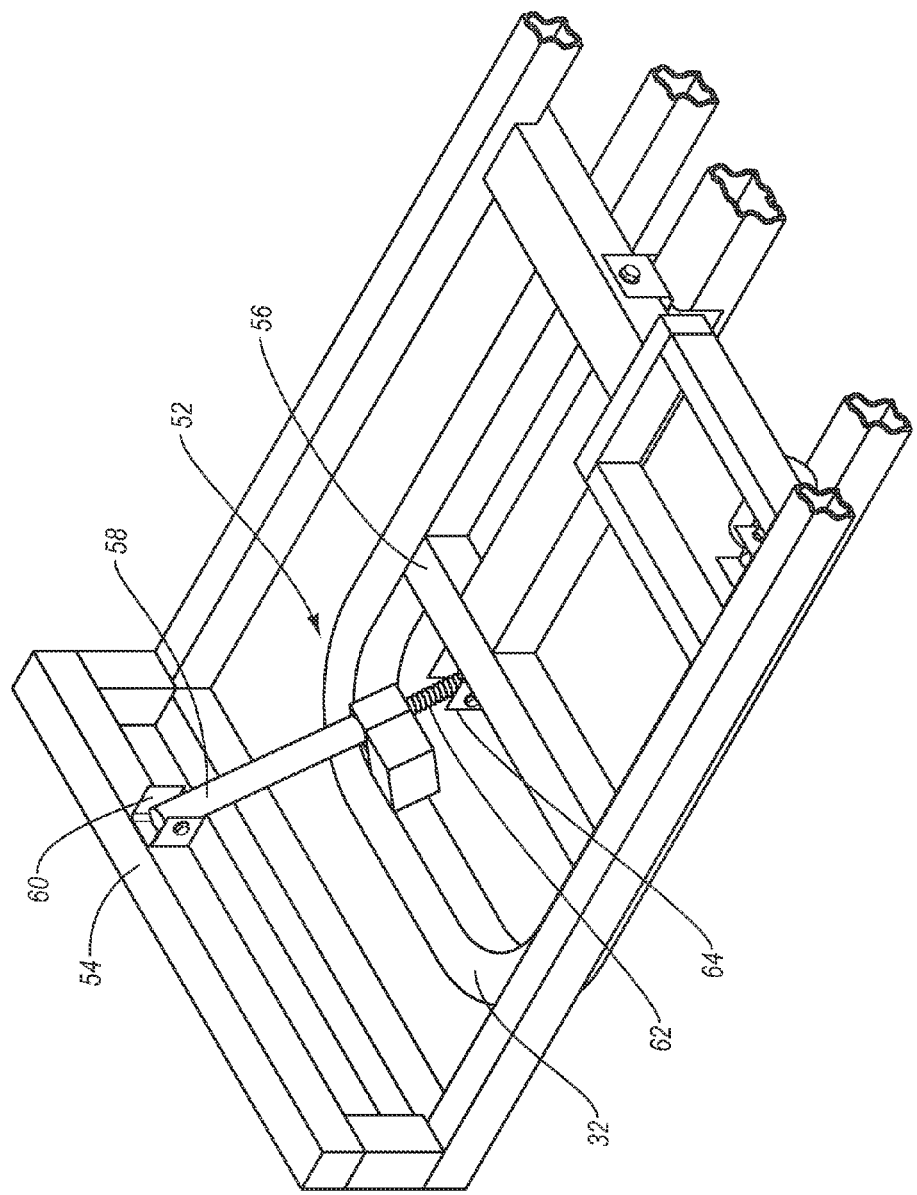
FIG. 7 is a cut away perspective view of the incline mechanism incorporated into the treadmill illustrated in FIGS. 2 through 6.

The inclination/declination of treadbase 26 can be accomplished through the use of an incline mechanism 52, as depicted in FIGS. 6 and 7, or another linearly extending assembly. Incline mechanism 52 raises or lowers one end of treadbase 26 relative to the other end. In the embodiment illustrated in FIGS. 6 and 7, incline mechanism 52 is pivotally coupled to a cross bar 54 of treadbase 26 and a cross bar 56 of base frame 32.

More particularly, a first end 58 of incline mechanism 52 is pivotally coupled to cross bar 54 by way of a bracket 60 while a second end 62 of incline mechanism 52 is coupled to cross bar 56 by way of a bracket 64. Each of brackets 60, 64 are generally U-shaped with a pin that can be secured between the two extending sides. The first and second ends 58, 62 of incline mechanism 52 are each mounted on the pin of their respective bracket 60, 64. As incline mechanism 52 raises or lowers the end of treadbase 26, first and second ends 58, 62 of incline mechanism 52 are able to pivot on the pins within brackets 60, 64. In this manner, first and second ends 58, 62 of incline mechanism 52 are able to pivot about axes that are generally transverse to a longitudinal axis of treadbase 26. As will be discussed in greater detail below, brackets 60, 64 can be pivotally coupled to cross bars 54, 56 to allow treadbase 26 to tilt from side to side without damaging incline mechanism 52.

In one embodiment, upon contraction of incline mechanism 52, treadbase 26 moves to a declined position such that the front end of treadbase 26 is positioned below the neutral position. When incline mechanism 52 is selectively extended to an extended position, treadbase 26 is inclined such that the front end of treadbase 26 is positioned above the neutral position. Through the inclination/declination of treadbase 26, as described above, treadmill 12a is able to simulate for a user the experience of walking or running on level ground, up hills, and down hills.

Figure 5:
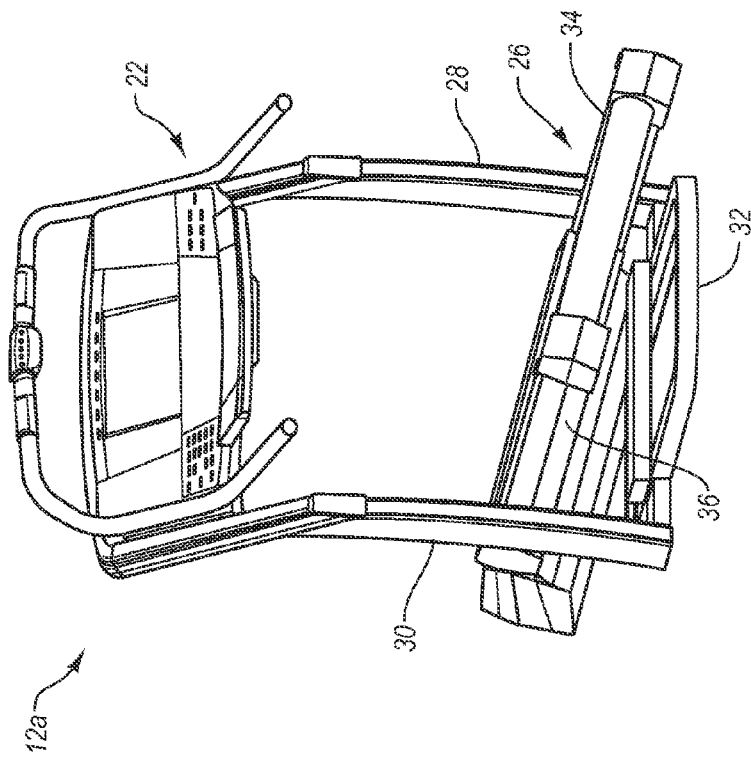
FIG. 5 is another rear perspective illustration of the treadmill of FIG. 2 with the treadbase in a second tilted position.
Figure 4:
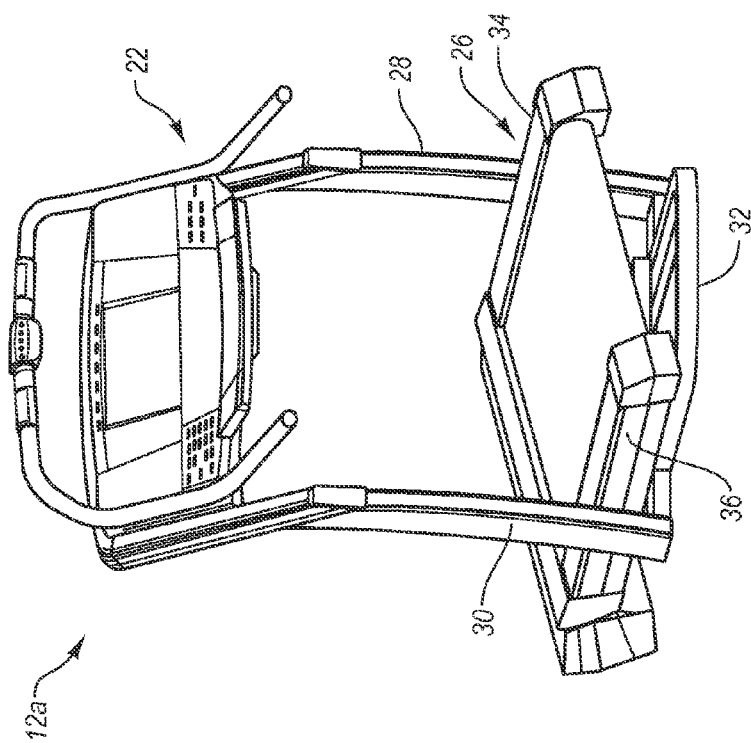
FIG. 4 is a rear perspective illustration of the treadmill of FIG. 2 with the treadbase in a first tilted position.

In the illustrated embodiment, treadmill 12a also permits treadbase 26 to be tilted from side to side in order to more closely replicate walking or running on outdoor terrain. As depicted in FIGS. 4 and 5, treadbase 26 can be tilted such that one side of treadbase 26 is higher than the other. For instance, FIG. 4 illustrates treadbase 26 tilted so that side rail 34 is higher than side rail 36. Similarly, FIG. 5 illustrates treadbase 26 tilted so that side rail 36 is higher than side rail 34. The ability to tilt treadbase 26 to one side or another allows treadmill 12a to more closely simulate outdoor terrain. In particular, when a person goes outside for a run or walk, the person often encounters both inclining and declining hills as well as surfaces that are not level from side to side, such as when walking or running across a hill. Thus, treadmill 12a more closely replicates an outdoor walking or running experience by providing a surface that inclines, declines, and tilts to each side.

Figure 8:
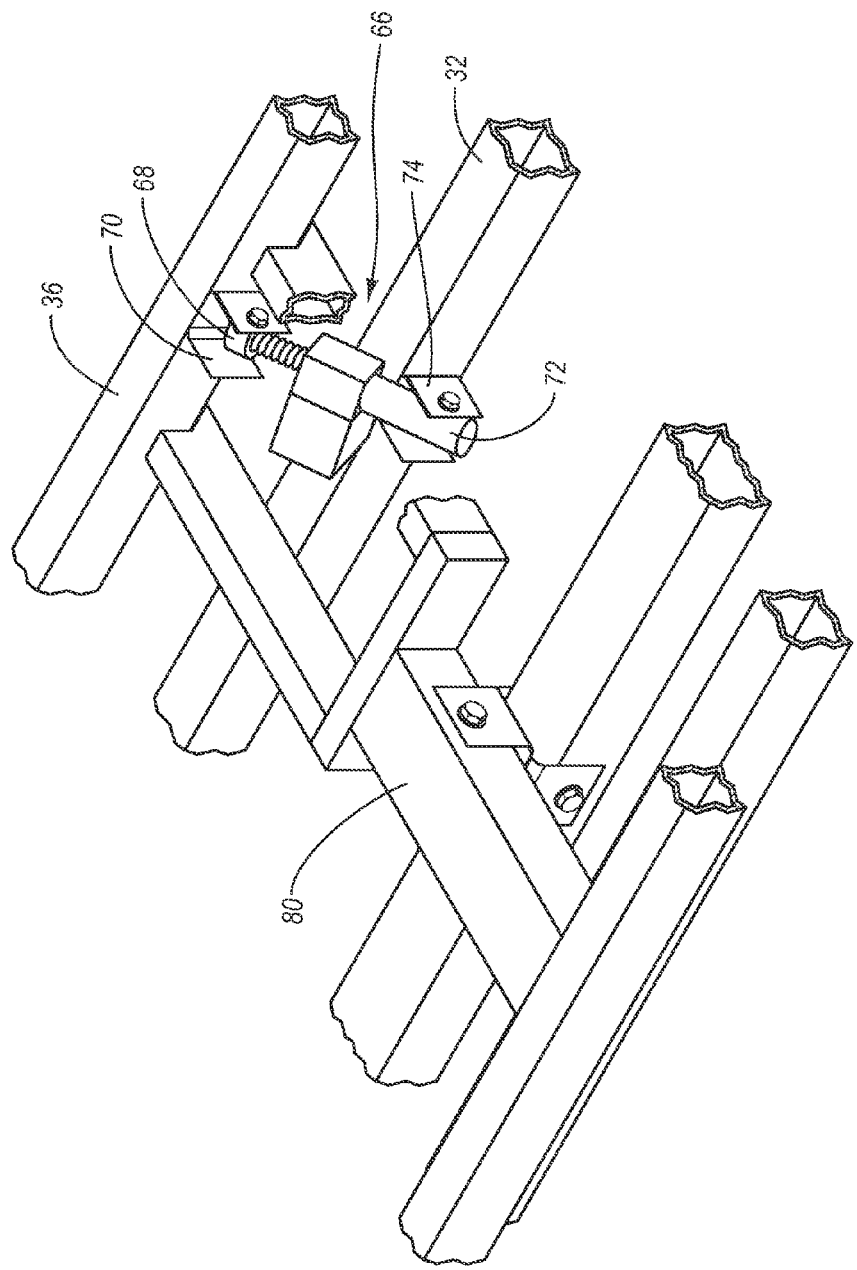
FIG. 8 is a cut away perspective view of the tilt mechanism incorporated into the treadmill illustrated in FIGS. 2 through 6.

The tilting of treadbase 26 can be accomplished through the use of a tilt mechanism 66, as depicted in FIGS. 6 and 8, or another linearly extending assembly. Tilt mechanism 66 is substantially similar to incline mechanism 52. Tilt mechanism 66 raises or lowers one side of treadbase 26 relative to the other side. In the embodiment illustrated in FIGS. 6 and 8, tilt mechanism 66 is pivotally coupled to side rail 36 of treadbase 26 and base frame 32.

More particularly, a first end 68 of tilt mechanism 66 is pivotally coupled to side rail 36 by way of a bracket 70 while a second end 72 of tilt mechanism 66 is coupled to base frame 32 by way of a bracket 74. Each of brackets 70 and 74 are generally U-shaped with a pin that can be secured between the two extending sides. The first and second ends 68, 72 of tilt mechanism 66 are each mounted on the pin of their respective bracket 70, 74. As tilt mechanism 66 raises or lowers the side of treadbase 26, first and second ends 68, 72 of tilt mechanism 66 are able to pivot on the pins within brackets 70, 74. In this manner, first and second ends 68, 72 of tilt mechanism 66 are able to pivot about axes that are generally parallel to a longitudinal axis of treadbase 26. As will be discussed below, brackets 70, 74 can be pivotally coupled to side rail 36 and base frame 32 to allow one end of treadbase 26 to incline relative to the other without damaging tilt mechanism 66.

In one embodiment, upon contraction of tilt mechanism 66, side rail 36 is moved to a lower position than side rail 34. When tilt mechanism 66 is selectively extended to an extended position, side rail 36 is moved to a higher position than side rail 34. Through the tilting of treadbase 26, as described above, treadmill 12a is able to more closely simulate for a user the experience of walking or running outdoors.

As noted above, brackets 60, 64, 70, 74 can be pivotally coupled to their respective cross bars or frames. Pivotally coupling brackets 60, 64, 70, 74 to their respective cross bars or frames prevents incline mechanism 52 and tilt mechanism 66 from being bent or otherwise damaged when treadbase 26 is inclined, declined, or tilted. For instance, the pivoting connection between brackets 70, 74, side rail 36, and base frame 32 allows treadbase 26 to incline or decline without bending, overextending, or otherwise damaging tilt mechanism 66. Similarly, the pivoting connection between brackets 60, 64 and cross bars 54, 56 allows treadbase 26 to tilt without bending, overextending, or otherwise damaging incline mechanism 52.

Brackets 60, 64, 70, 74 can be pivotally coupled to their respective cross bars or frames with the use of a mechanical fastener, such as a bolt. The bottom cross portion of the generally U-shaped bracket can have a bolt extending therethrough and which is secured within the respective cross bar or frame of each bracket. The bolt connection can allow the bracket to rotate thereon. It will be appreciated, however, that one or more of brackets 60, 64, 70, 74 can be connected to their respective cross bars or frames is a non-pivoting or non-rotating manner. For example, one or more of brackets 60, 64, 70, 74 can be welded to their respective cross bars or frames.

Figure 9:
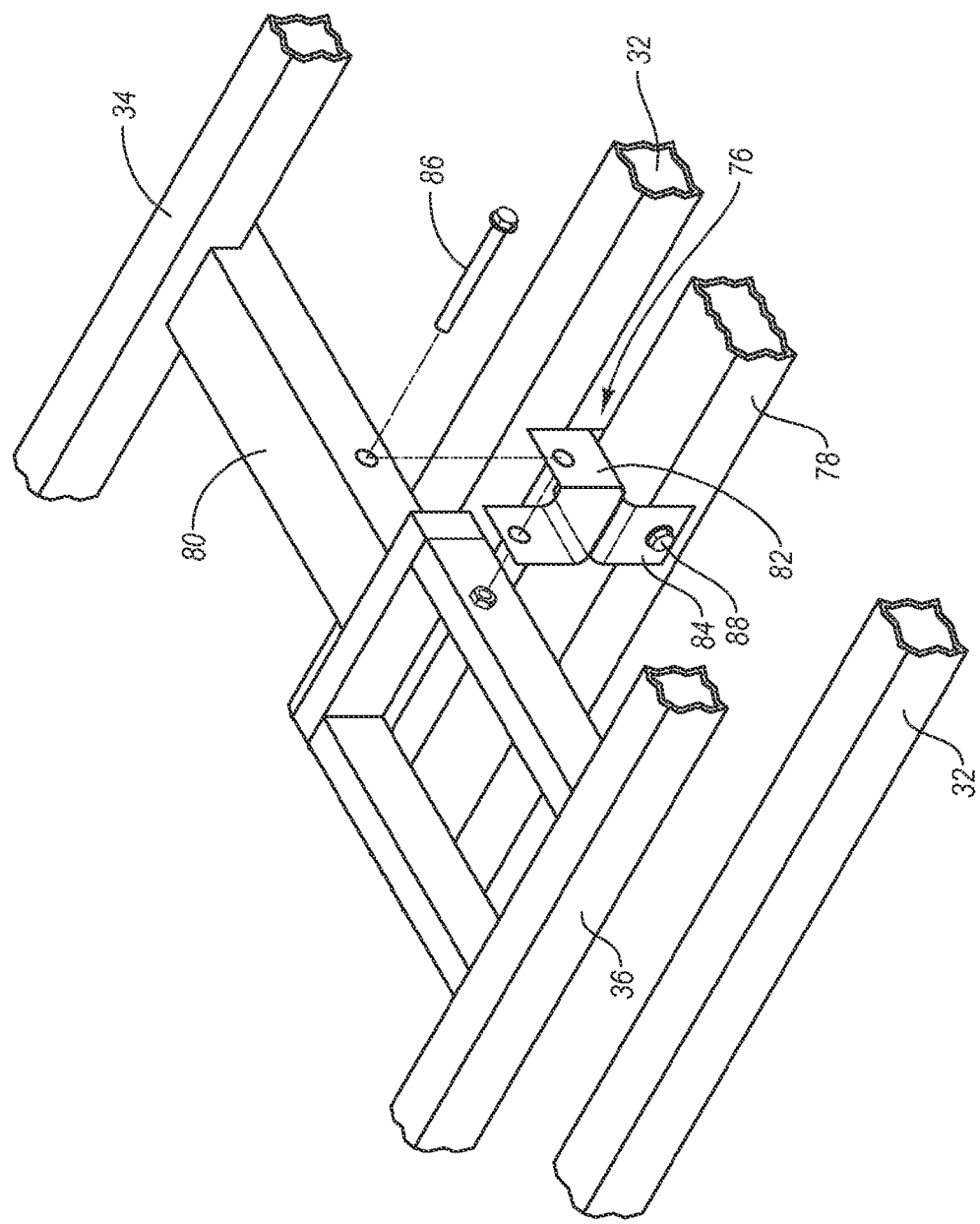
FIG. 9 is a cut away perspective view of a bracket assembly incorporated into the treadmill illustrated in FIGS. 2 through 6 which facilitates inclination/declination and tilting of the treadbase relative to the base frame.

With continuing attention to FIG. 6, attention is now also directed to FIG. 9, which illustrates a bracket assembly 76. Bracket assembly 76 facilitates the inclination, declination, and tilting of treadbase 26 relative to base frame 32. As best seen in FIG. 6, base frame 32 includes a cross member 78 that extends between the rear end of base from 32 and cross member 56. Cross member 78 is generally in line with incline mechanism 52. Treadbase 26 also includes a cross member 80 that extends between side rails 34 and 36. Cross member 80 is generally in line with tilt mechanism 66. As can be seen in the Figures, cross member 80 extends across and over cross member 78 such that cross members 78 and 80 are generally perpendicular to one another.

Bracket assembly 76 pivotally couples together treadbase 26 and base frame 32. In the illustrated embodiment, bracket assembly 76 comprises two generally U-shaped brackets 82, 84. Each of brackets 82, 84 have two substantially parallel walls and a cross member that connects the walls, thereby forming a channel within each bracket 82, 84. The cross members of bracket 82, 84 are coupled together such that the walls of bracket 82 extend in an opposite direction of the walls of bracket 84. As best seen in FIG. 9, brackets 82, 84 are coupled together such that the channels formed by brackets 82, 84 extend in generally perpendicular directions. In other words, brackets 82, 84 are offset by about 90°. Brackets 82, 84 can be coupled together by any suitable means, including welding, bolts, and the like.

Cross member 80 is pivotally coupled within the channel of bracket 82 with a pin 86. Pin 86 extends through the walls of bracket 82 and through a hole in cross member 80. Coupling cross member 80 to bracket 82 in this manner enables treadbase 26 to tilt relative to bracket assembly 76 about an axis that is substantially parallel to a longitudinal axis of treadbase 26.

Bracket assembly 76 is coupled to base frame 32 is a similar manner as treadbase 26. Specifically, cross member 78 is pivotally coupled within the channel of bracket 84 with a pin 88. Pin 88 extends through the walls of bracket 84 and through a hole in cross member 78. Coupling cross member 78 to bracket 84 in this manner enables bracket assembly 76 and treadbase 26 to pivot relative to base frame 32 about an axis that is substantially perpendicular to a longitudinal axis of treadbase 26. Pivoting of bracket assembly 76 and treadbase 26 in this manner allows treadbase 26 to be inclined or declined as described herein.

Figure 10:
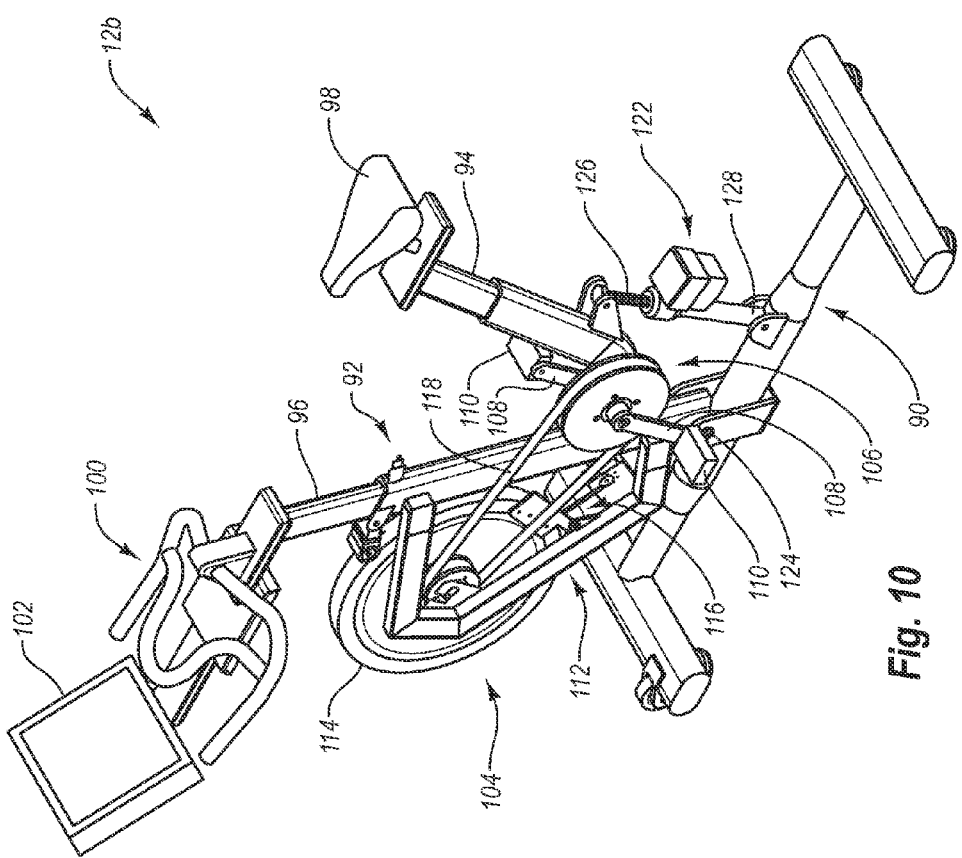
FIG. 10 is a perspective illustration of a stationary exercise cycle to be used in the exercise system of FIG. 1.
Figure 11:
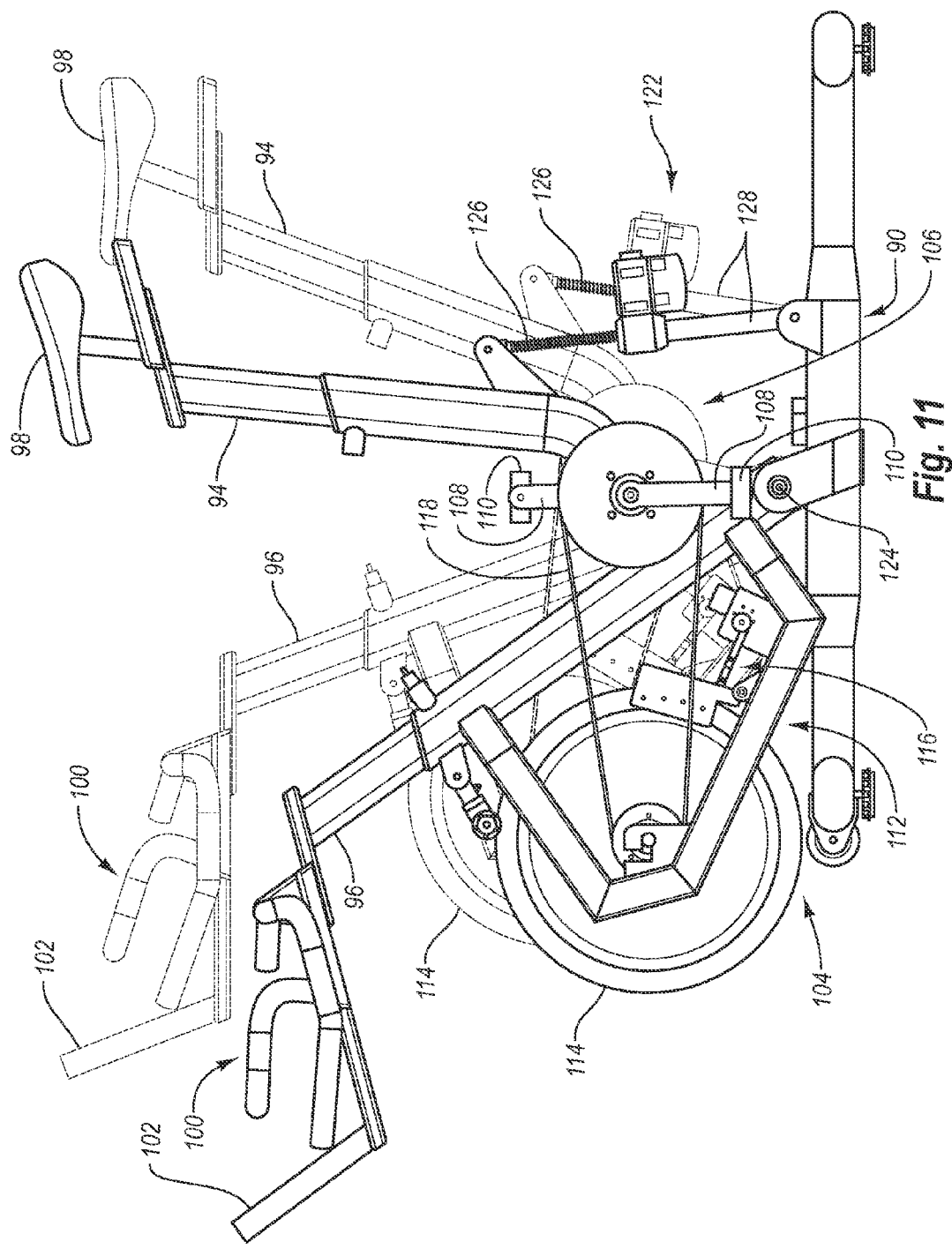
FIG. 11 is a side illustration of the stationary exercise cycle of FIG. 10 with the upright frame shown in a forward tilted position, and a neutral position featured in phantom view.
Figure 12:
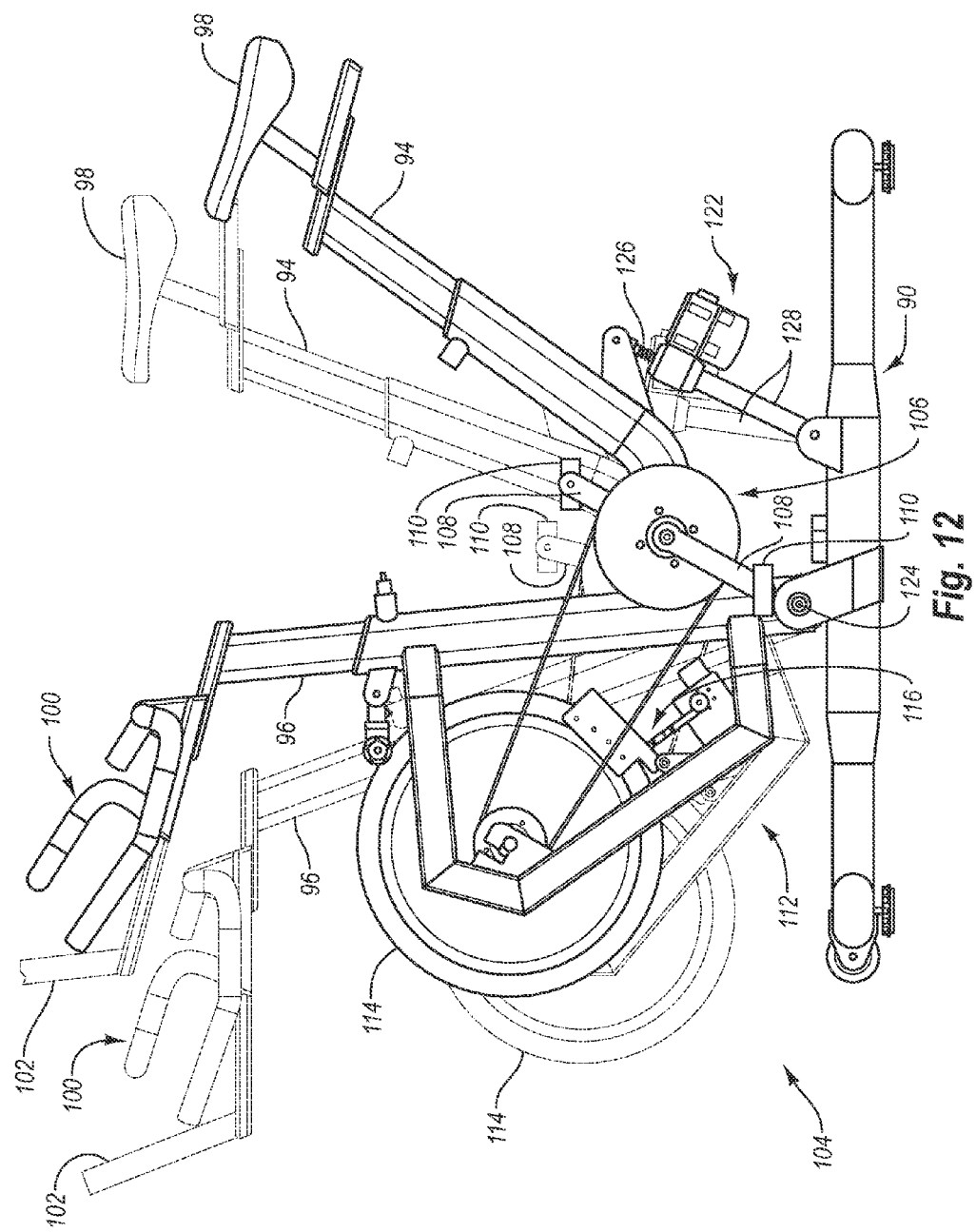
FIG. 12 is another side illustration of the stationary exercise cycle of FIG. 10 with the upright frame shown in a backward tilted position, and a neutral position featured in phantom view.

Attention is now directed to FIGS. 10 through 12, which generally illustrate an exercise cycle 12b that can be used with system 10. Exercise cycle 12b, in one embodiment, includes a support base 90 and a generally upright support structure 92 pivotally coupled thereto. Upright support structure 92, in this illustrative embodiment, includes two support members 94, 96. Support member 94 includes a seat 98 upon which a user may sit when exercising on exercise cycle 12b. Support member 96 includes a handlebar assembly 100 and a control panel 102.

In the illustrative embodiment, a drive assembly 104 is mounted on upright support structure 92. Drive assembly 104 includes a rotatable pedal assembly 106. Pedal assembly 106 includes a pair of cranks 108 that are rotatably mounted on support member 94. Attached to each crank 108 is a pedal 110, which a user can engage with their feet to rotate pedal assembly 106. As will be appreciated by one skilled in the art, pedal assembly 106 can also be mounted on support member 96 or support base 90.

Drive assembly 104 also includes a resistance assembly 112 for providing resistance to the rotation of pedal assembly 106. Resistance assembly 112 includes a flywheel 114 and a braking mechanism 116 mounted on support member 96. Braking mechanism 116 is adapted to selectively adjust the rotational speed of flywheel 114. Resistance assembly 112 is coupled to pedal assembly 106 by an endless belt or chain 118 such that the rotational speed of pedal assembly 106 and flywheel 114 are related to one another.

Braking mechanism 116 can comprise a frictional brake, a magnetic brake, or any other suitable brake for controlling the rotational speed of flywheel 114. Braking mechanism 116 is optionally coupled to an exercise cycle controller 120 (not shown), which is similar to treadmill controller 50. Exercise cycle controller 120 controls the operation of braking mechanism 116, and thus the rotational speed of flywheel 114 in response to various user inputs or other control signals. Exercise cycle controller 120 can be incorporated within resistance assembly 112, control panel 102, or within personal computer 16.

Because resistance assembly 112 is coupled to pedal assembly 106, the braking provided to flywheel 114 by braking mechanism 116 affects the resistance to the rotation of pedal assembly 106. In other words, when a large braking force is applied to flywheel 114, it is harder for a user to rotate pedal assembly 106. Conversely, when little or no braking force is applied to flywheel 114, it is relatively easy for a user to rotate pedal assembly 106. By adjusting the amount of braking applied to flywheel 114, exercise cycle 12b can thus vary speed at which a user can pedal and/or the resistance experienced by the user as he or she pedals on exercise cycle 12b. In this manner exercise cycle 12b is able to simulate the types of resistances and pedaling speeds that a user may experience if riding a bicycle outdoors.

In addition to the ability to control and vary the speed and resistance of pedal assembly 106, exercise cycle 12b also permits the tilting of upright support structure 92 relative to the floor, or other surface upon which exercise cycle 12b rests, to be varied. As depicted in FIG. 11 in phantom lines, upright support structure 92 can be oriented in a neutral position. In the neutral position, handle bar assembly 100 and seat 98 are at generally the same vertical height. When upright support structure 92 is in the neutral position, a user sitting on seat 98 will feel that he or she is sitting on a bicycle that is on a level surface. Additionally, as illustrated in solid lines in FIG. 11, upright support structure 92 can be oriented in a forwardly tilted position such that the handle bar assembly 100 is vertically below the neutral position and seat 98. Tilting upright support structure 92 forward as illustrated in FIG. 11 enables a user to simulate riding down a hill.

In one embodiment, upright support structure 92 can also be oriented in a backwardly tilted position in which the handle bar assembly 100 is vertically above the neutral position and seat 98. Typical bicycle rides outside, for example, involve inclines and declines as well as flat surfaces, each of which can be accommodated and replicated by the tilting ability of upright support structure 92. Thus, exercise cycle 12b is able to more closely simulate a typical outdoor bicycle ride.

The forward and backward tilting of upright support structure 92 can be accomplished through pivotally coupling upright support structure 92 to support base 90 as depicted in FIGS. 10 through 12. As seen in the Figures, upright support structure 92 is connected to support base 90 by pivot 124. Pivot 124 allows upright support structure 92 to tilt forward and backward as described above. Pivot 124 can include a pin that extends through a portion of support base 90 and through upright support structure 92. Pivot 124 can also include one or more stops to limit the tilting of upright support structure 92 within a desired range.

While pivot 124 allows upright support structure 92 to tilt forward and backward, extension mechanism 122, or another linearly extending assembly, controls the tilting of upright support structure 92. In the illustrative embodiment, extension mechanism 122 is coupled between support base 90 and support member 94. More particularly, a first end 126 of extension mechanism 122 pivotally couples to support member 94 while a second end 128 of extension mechanism 122 pivotally couples to support base 90. Extension mechanism 122 raises or lowers support member 94 relative to support base 90, thereby determining the tilt of upright support structure 92. Extension mechanism 122 can also be coupled between support base 90 and support member 96 or drive assembly 104.

As with braking mechanism 116, extension mechanism 122 is optionally coupled to exercise cycle controller 120. Exercise cycle controller 120 controls the operation of extension mechanism 122, and thus the tilt of upright support structure 92 in response to various user inputs or other control signals.

In one embodiment, upon contraction of extension mechanism 122, support member 94 is lowered, causing upright support structure 92 to tilt backward so that seat 98 is below the neutral position. When extension mechanism 122 is selectively extended to an extended position, support member 94 is raised, causing upright support structure 92 to tilt forward so that seat 98 is above the neutral position. Through the forward and backward tilting of upright support structure 92, as described above, exercise cycle 12b is able to more closely simulate for a user the experience of riding a bicycle on level ground as well as up and down hills.

Attention is now directed back to system 10 and how system 10 simulates an outdoor exercise experience. More specifically, the following discussion will be directed toward how system 10 enables a user to i) select a real world route, trail, path, or course, ii) exercise on an exercise device 12 that simulates the terrain of the selected real world route, trail, path, or course, and iii) view images of the real world route, trail, path, or course while exercising on the exercise device 12. While the following discussion will be directed toward using treadmill 12a with system 10, it will be appreciated from the disclosure herein that other types of exercise devices, such as exercise cycle 12b, can be used with system 10.

Figure 2:
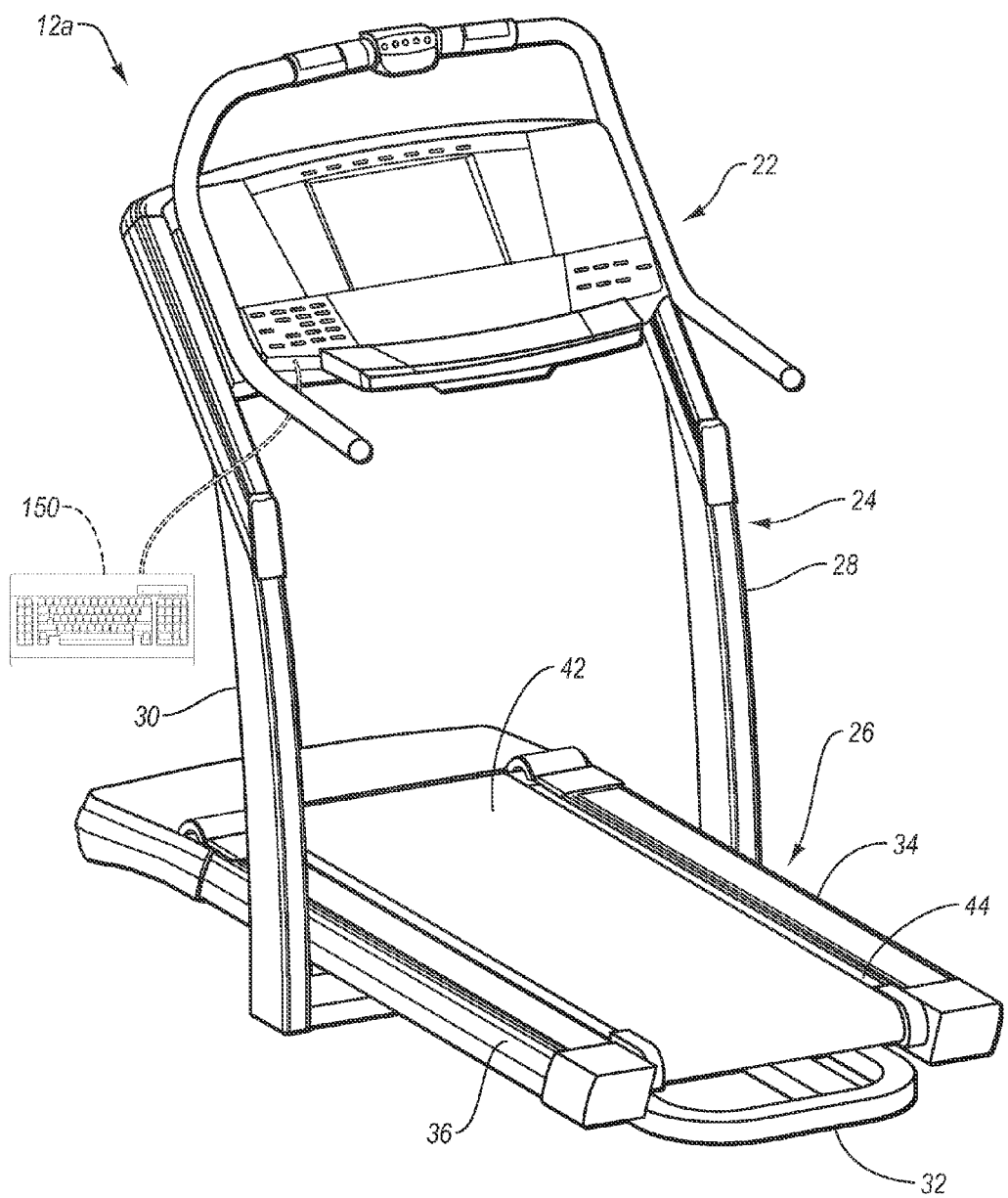
FIG. 2 is a perspective illustration of a treadmill to be used in the exercise system of FIG. 1.

As shown in FIG. 2, treadmill 12a includes control panel 22 attached to side members 28, 30 of upright support structure 24. Control panel 22, in one embodiment, as shown in FIG. 6, includes one or more interface devices. Such interface devices may be either input devices or output devices. Input devices enable a user to input and vary the operating parameters of treadmill 12a. As examples of such input devices, control panel 22 includes many typical controllers for use on an exercise device, such as a treadmill. A number of illustrative input devices include but are not limited to time controls 126, distance controls 128, speed controls 130, incline controls 132, a start button 134, a stop or pause button 136, and heart rate controls 138. In addition to these input devices, such as one or more controllers, control panel 22 further optionally includes an iFit.com button 140, a manual override button 142, and a scaling control 144, each of which are also examples of input devices. It may be appreciated that each of the above-recited controllers or buttons may be embodied in a variety of different manners to perform their commonly utilized function. In addition, each controller, button, and the like may take the form of one or more switches, rheostats, potentiometers, touch sensitive controls, voice activated controllers, and the like. The input devices described herein are examples of structures capable of performing the function of interface means for gathering a first signal (such as a real time signal) from the user. One skilled in the art may identify various other configurations of interface means that are capable of performing the desired function.

In addition to the above-described input devices control panel 22 may include a variety of other input devices. For example, control panel 22 may include an integrally formed mouse 146. Additionally, control panel 22 may include a keyboard jack 148 for an external keyboard 150 (FIG. 2), a touch-sensitive video display 152, and various other ports, jacks, or the like to receive various other external components. It will be appreciated that the external components, such as keyboard 150, may be integrally formed within control panel 22. Additionally, one or more of the input devices may be incorporated into personal computer 16 (FIG. 1).

Each input device is adapted to allow a user operating treadmill 12a to more fully operate one or more operating parameters of treadmill 12a. Furthermore, the input devices enable the user to access communication system 14 and/or obtain maps, topographical information, pictures or videos of real world places, or other information via network 18, whether such information is from communication system 14, one or more third parties 20, or from one of a variety of other hardware and/or software modules that are accessible via network 18. For example, the input devices may allow the user to access the Internet to find maps, topographical data, pictures, and/or videos of real world locations, routes, paths, courses, and the like. These additional input devices are further examples of structures capable of performing the function of interface means, communicating with the exercise mechanism, for gathering a first signal from the user.

Figure 13:
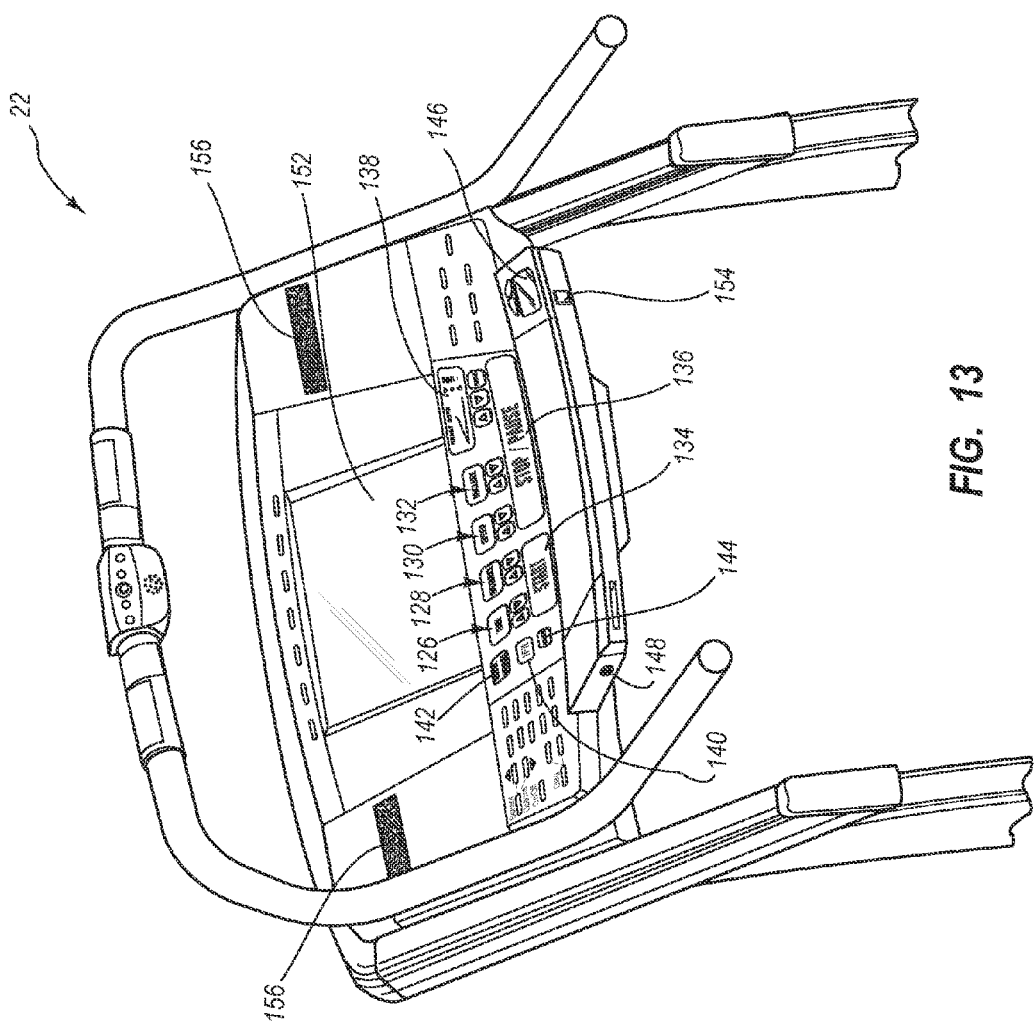
FIG. 13 is a perspective illustration of the control panel of the treadmill of FIG. 2.

As shown in FIG. 13, the iFit.com button 140, in one embodiment, acts as both a selector and an indicator of connectivity of treadmill 12a to communication system 14, and optionally one or more third parties 20, whether such connectivity is via computer 16, wireless router 17, or directly from treadmill 12a. The iFit.com button 140 optionally includes an indicator light (not shown) that demonstrates when a connection has been established between treadmill 12a and communication system 14, such as when the iFit.com button 140 is depressed. Alternatively, a light emitting diode (LED) positioned in close proximity to the iFit.com button 140 may be activated when the iFit.com button 140 is activated.

As discussed above, the connection achieved by activating iFit.com button 140 may be via a variety of communication line connections. For example, as shown, control panel 22 includes a wireless port 154 that enables treadmill 12a to wirelessly communicate with network 18 (FIG. 1), either directly or via computer 16 and/or wireless router 17. Alternatively, control panel 22 may have a hard wire connection to network 18, either directly or via computer 16.

In one embodiment, by activating iFit.com button 140, a user of treadmill 12a, or other exercise device, connects to communication system 14, such as a website. Such connection may be via an independently located computer, such as computer 16, through a modem (not shown), wireless router 17, or directly through a local area network (LAN) or wide area network (WAN) by way of the described communication line connections for example, or other connections known to one skilled in the art. More specifically, by activating the iFit.com button 140 a signal is transmitted via network 18 to communication system 14 to create a connection therebetween.

As illustrated in FIG. 14, once a connection is made between treadmill 12a and communication system 14, a user may access various programs, features, and the like of communication system 14. For example, once a connection is made, a user can access, select, create, and/or download exercise programming for use with treadmill 12a. As discussed below, the exercise programming can include one or more signals that are able to adjust one or more operating parameters of treadmill 12a as well as video and/or audio programming. With an established connection to communication system 14, the user can also select other options, such as personal training, health information, competition, diagnostics, and the like, as shown in FIG. 14.

In another embodiment, a user may access communication system 14 using personal computer 16. With a connection established between personal computer 16 and communication system 14, a user may access the programs, features, and options mentioned above. After the user selects the desired option, such as selecting an exercise program, communication system 14 can communicate the exercise program to treadmill 12a directly or via personal computer 16 or a portable memory device, such as a Secure Digital (SD) memory card.

Figure 16:
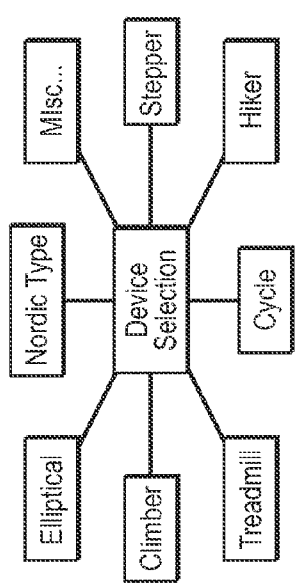
FIG. 16 is a functional block diagram of the process of selecting an exercise device to be used in connection with the exercise programs.

In either embodiment, and as illustrated in FIG. 15, when a user indicates that he or she would like to select and download an exercise program, communication system 14 may prompt the user to select the type of exercise device upon which the exercise program will be used. FIG. 16 illustrates a functional block diagram of the process of selecting an exercise device to be used in connection with the exercise program. As seen in FIG. 16, the user may be given the option to select from among many different types of exercise devices, including treadmills, cycles, Nordic type skiers, climbers, hikers, steppers, ellipticals, and the like. After selecting the type of exercise device to be used, the user can then select the desired exercise program that is compatible with the selected exercise device.

The exercise programming can take any one of a number of forms. The exercise programming can include signals generated by communication system 14 and sent to treadmill 12a. The signals may include exercise control signals, audio programming, and/or display programming. The exercise controls signals can be configured to control/adjust one or more operating parameters of treadmill 12a, such as the exercise time, the incline and/or tilt of treadbase 26, and/or the speed of belt 42. The video and/or audio programming can provide various types of information, including instruction, education, and entertainment.

As illustrated in the embodiment of FIG. 15, the user may select between preprogrammed exercise programming and user defined exercise programming. When a user selects the preprogrammed exercise programming option, the user can view and select from among one or more available preprogrammed exercise programs. The signals of the selected exercise programming can then be sent over network 18 to treadmill 12a to control the operating parameters of treadmill 12a and/or provide video/audio programming to the user. The exercise programming may include common exercise routines that vary the speed and incline of treadmill 12a at various time intervals during the routine.

The exercise programming may also be adapted to simulate a real world environment, such as a trail, route, course, path, or the like. By way of non-limiting example, the exercise programming may be adapted to simulate the New York City Marathon. More specifically, the control signals can be adapted to adjust the incline and tilt of treadbase 26 to replicate the hills, level surfaces, and the like, encountered on the route of the race.

In addition to adjusting the physical operating parameters of treadmill 12*a*, the exercise programming can include video and/or audio programming that is related to the control signals. The display programming can be presented on video display 152, while the audio programming can be presented by audio output 156, such as a speaker. In the example of the exercise programming simulating the New York City Marathon course, the display programming can include still or moving images of the course, including buildings, bridges, and roads that are seen along the course.

The display programming can be synchronized with the control signals that adjust the operating parameters of treadmill 12*a*. Synchronizing the control signals and the display programming allows a user to view the real world environment at the same time the user encounters operating parameters that simulate the viewed real world environment. For example, as a user runs on treadmill 12*a*, the control signals may cause treadmill 12*a* to simulate the terrain (i.e., hills, etc.) that a runner would encounter as he or she runs through Central Park. As the user of treadmill 12*a* experiences the terrain of Central Park, the user can also view images, whether still or moving, of the area of Central Park which the control signals are simulating.

Similar to the display programming, the audio programming can include typical sounds heard by a runner in the race, including the cheers of the crowd, cars, sirens, horns, and the like. The audio programming may also provide information about the images presented in the display programming. For example, the audio programming may include information typically provided on tour of New York City. The audio programming can be synchronized with the control signals and the display programming so that the sounds and/or information provided by the audio programming is related to what the user is seeing on video display 152 and experiencing on treadmill 12*a*. For instance, as the user views images and experiences the terrain of Central Park, the user may also hear sounds typical of Central Park, such as children playing, dogs parking, and people talking. Additionally, or alternatively, the user may be provided with information in narrative form about Central Park, such as its size, history, or other interesting facts.

While the exercise programming has been described above in connection with the New Your City Marathon, it will be appreciated that the exercise programming may simulate other real world environments, such as other races, mountain hikes, city tours, or any other course, route, path, and the like.

Alternatively, as illustrated in FIG. 15, the user may select the user defined exercise programming option. Communication system 14 may be configured to allow a user at treadmill 12*a* or personal computer 16 to create exercise programming suitable to the desires of the user. When creating a user defined or unique exercise program, the user may have the option to select, among other things, a desired route, display programming, and/or audio programming. The user may also have the option to select other exercise programming parameters, such as the exercise time, changes in the speed of belt 42, changes in the incline and/or tilt of treadbase 26, and the like.

By way of example, a user accessing communication system 14 may be able to select a real world environment which he or she would like treadmill 12*a* to simulate. In selecting the real world environment, the user may select a starting point, and ending point, and a specific route between the two. Alternatively, the user may select a starting point and an ending point, and allow communication system 14 and/or one or more of third parties 20 to select the route therebetween. In still other embodiments, the user may select a starting point and allow communication system 14 and/or one or more of third parties 20 to select a route that proceeds from the starting point for a selected time, distance, or the like. As noted above, the real world environment may be a famous or well known race course, tour route, hike, or the like. Alternatively, a user may create an exercise program that simulates any other real world environment.

For instance, during good weather, a user of treadmill 12*a* may also like to run outdoors along a route the user has developed, such as along the roads in his or her neighborhood. During bad weather, however, the use may prefer to run on treadmill 12*a*. In such a case, the user may access communication system 14 and create an exercise program that simulates his or her neighborhood route. More specifically, the exercise program can include controls signals that adjust the operating parameters of treadmill 12*a* to simulate the actual terrain (i.e., hills and level surfaces) of the neighborhood route. Additionally, exercise programming can also provide display programming showing images of the neighborhood route. As with the preprogrammed exercise programs, the display programming can be synchronized with the control signals so that a user is able to view images of the real world environment associated with the actual terrain that is simulated on treadmill 12*a*.

In order to generate exercise programming as described above, communication system 14 may require access to one or more types of data. Some types of data that may be needed to generate the above described exercise programming include maps, topographical data, video or image data, audio data, and the like. The map data allows the user to create a route through a real world environment which will be simulated on treadmill 12*a*. The topographical data can be used to generate control signals that adjust one or more operating parameters of treadmill 12*a* to simulate the actual topography along the real world route. The video/image data and the audio data can be used to provide the user with a visual representation of and/or audio information relating to the real world route that is simulated on treadmill 12*a*.

The data used to generate the exercise programming may be stored at communication system 14 or at one or more other locations. For example, communication system 14 may communicate with one or more third parties 20 which store data. Third parties 20 may be websites and/or databases that are accessible via network 18. The following are a few examples of third parties 20 that can be accessed to retrieve information and data that can be used to generate the above described exercise programming.

There are multiple route planning and mapping software applications and programs which can be used by communication system 14 and/or a user at treadmill 12*a* to develop a route for exercise programming as described herein. Examples of such are MAPQUEST.COM, MAPS.GOOGLE.COM, and GOOGLE EARTH (available at earth.google.com). With these applications, a user is able to select a starting point and an ending point. The applications provide multiple different routes between the two points. Alternatively, the applications allow for the creation of customized routes between the beginning and end points by selecting intermediate points between the beginning and ending points.

Similarly, there are multiple databases that store topographical data for specific regions of the world. In addition, the U.S. Geological Survey maintains a database, the GTOPO 30 or Global Topography at 30 arc/second database (available at edc.usgs.gov), which includes topographical data for the entire world. Communication system 14 can access one or more of these databases to retrieve information and data regarding the real world route that is to be simulated on treadmill 12. With this data, communication system 14 can generate the control signals that control one or more of the operating parameters of treadmill 12a, such as the incline and/or tilt of treadbase 26, to simulate the terrain of the real world route.

Databases that store still or moving images of real world locations can also be accessed by communication system 14 in order to provide to the user of treadmill 12a a visual representation of the real world route that is simulated on treadmill 12a. Examples of such databases include the GOOGLE EARTH, GOOGLE STREET VIEW (available at MAPS.GOOGLE.COM), and MICROSOFT VIRTUAL EARTH (available at www.microsoft.com/virtualearth) databases. These databases provide a bird's eye view or a street level view of a selected route or location.

With access to at least some of the data described above, communication system 14 is able to generate exercise programming that allows treadmill 12a to simulate real world environments. In one embodiment, a user of treadmill 12a accesses communication system 14 via control panel 22. Communication system 14 provides a user interface that allows the user to select a preprogrammed exercise route or create a user defined exercise route. In the case of creating a user defined exercise route, communication system 14 allows the user to enter a starting point, an ending point, and/or one or more intermediate points that will defined the exercise route.

With the supplied starting point, ending point, and/or one or more intermediate points, communication system 14 communicates with one or more third parties 20 that provide map and topographical data relating to the selected route. The map and topographical data provided by the third parties 20 may include a map highlighting the selected route, total route distance, route directions, travel times for specific speeds, as well as forward, backward, and side-to-side elevation changes along the selected route.

Communication system 14 can also communicate with one or more other third parties 20 to retrieve other data relating to the selected route. Communication system 14 can, for example, communicate with the GOOGLE STREET VIEW database to retrieve images of the selected route. Furthermore, communication system 14 can access other types of databases, such as audio databases, that provide audible information relating to the selected route.

Once communication system 14 has retrieved the desired information for the selected route, communication system 14 compiles the gathered data and generates the exercise program. Communication system 14 uses the map and topographical data to generate a series of control signals that control one or more operating parameters of treadmill 12a. In other words, using a correlation algorithm, communication system 14 can synchronize the topographical data with the map data to correlate the distance and the grade or elevation change between two points on the selected route and generate a control signal that will cause treadmill 12a to simulate that terrain. For instance, communication system 14 can use the map data to determine that the distance between point A and point B is ½ mile, and can use the topographical data to determine that the area between points A and B has a grade of 12%. Using this information, communication system generates one or more control signals that will cause treadmill 12a to incline treadbase 26 to a 12% grade until the user has walked for ½ mile. In a similar manner, communication system 14 can use the map data, the topographical data, and other reference points along the selected route to generate control signals that control the tilt of treadbase 26.

In addition to generating the control signals, communication system 14 can also generate display programming to accompany the control signals. As mentioned above, the display programming can include still or moving images of the selected real world route, which communication system 14 retrieves from one or more third parties 20. For example, communication system 14 communicates with a third party 20, such as the Google Street View database via the Google Maps API (application programming interface), to retrieve a series of images from of the selected real world route. When a series of images are used to provide a visual depiction of the selected rout, the images can be cached or buffered so that upon delivery to the user of treadmill 12a, the images provide an almost seamless, video-like depiction of the selected real world route.

As mentioned above, communication system 14 can synchronize the display programming with the control signals. In this manner, the control signals will adjust the operating parameters of treadmill 12a at the same time the display programming depicts a change in the terrain of the real world route. For instance, at the same time the control signals begin to cause treadbase 26 to incline to simulate a hill on the real world route, the display programming shows one or more images of the hill on the real world route as if the user were actually beginning to ascend the hill.

Once remote communication system 14 has generated the control signals from the topographical/map data and the display programming from the retrieved images of the real world route, remote communication system 14 can employ a correlation algorithm to synchronize the control signals with the display programming. In one embodiment, the correlation algorithm uses data about the series of retrieved images, such as the number of images along the real world route, the real world distances between the images, and the like. Similarly, the correlation algorithm also uses information from the retrieved topographical/map data, such as distances between locations on the real world route, changes in elevation between locations on the real world route, directional changes along the real world route, and the like. Using this data, the correlation algorithm synchronizes the control signals and the display programming. For example, the correlation algorithm may coordinate the first control signal with the display of the first image of the remote real world route. The correlation algorithm may correlate a subsequent image with a change in the map data, such as when the map data indicates a change in a certain distance from the previous real world location. The correlation algorithm may also correlate subsequent images with a change in the topographical data, such as an elevation change from the previous real world location.

In some embodiments, communication system 14 also provides audio programming that is synchronized with the control signals and the display programming. The audio programming can include sounds that may typically be heard along the real world route, such as cars, sirens, animals, people, and the like. The audio programming can also include in narrative form information about sites along the real world route. For example, if a user chose to have treadmill 12a simulate a route through Washington D.C. which passed by sites such as the White House, the U.S. Capital building, the Lincoln Memorial, and the Washington Monument, the audio programming could provide information about each of these sites, such as might be heard during a tour of Washington D.C.

A correlation algorithm, such as the one described above, may be used to coordinate the presentation of the audio programming with the display programming and the control signals.

Figure 17:
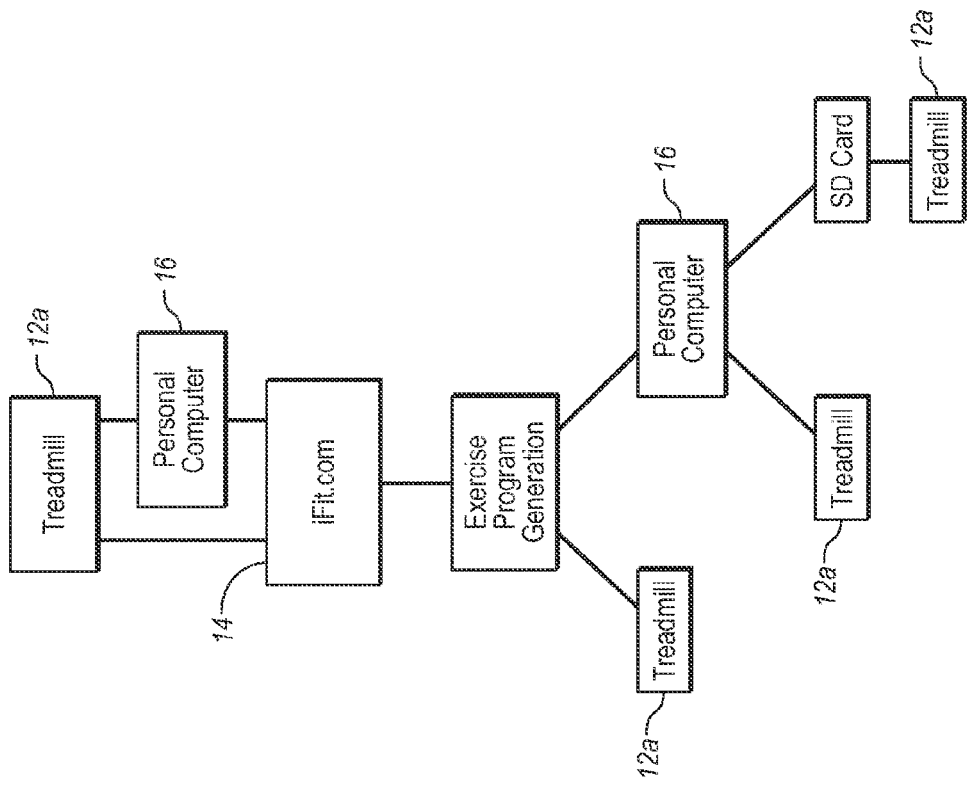
FIG. 17 is a flow diagram of the process of accessing a remote communication system, creating exercise programming, and downloading the exercise programming for use an on exercise device.

As shown in the flow diagram of FIG. 17, in one exemplary embodiment, a user may access remote communication system 14 directly from treadmill 12a (using control panel 22), from personal computer 16, or from treadmill 12a via personal computer 16. Connection between remote communication system 14 and treadmill 12a and/or personal computer 16 can be achieve via network 18, as described herein. Network 18 and remote communication system 14 in this embodiment are the Internet and a website, respectively. Once a connection has been established with remote communication system 14 and the user has indicated that he/she would like to create exercise programming, the user may define a remote, real world exercise route by entering a starting point, an ending point, and/or one or more intermediate points. With the remote, real world exercise route defined by the starting point, ending point, and/or one or more intermediate points, remote communication system 14 accesses one or more third parties 20 to retrieve data relating to one or more characteristics of the defined remote, real world exercise route. Remote communication system 14 then uses the retrieved data to generate exercise programming for treadmill 12a.

In one embodiment, remote communication system 14 may access MAPQUEST.COM to obtain map data, including distances, directions, and the like, relating to the defined remote, real world exercise route. Remote communication system 14 may also access a database, such as the GTOPO 30 database, that stores topographical data relating to the defined remote, real world exercise route. Remote communication system 14 can use the map data and topographical data retrieved from these third parties 20 to generate control signals that will cause treadmill 12a to simulate the terrain of the remote, real world exercise route. In addition, remote communication system 14 may access a database, such as the GOOGLE STREET VIEW database, to retrieve a plurality of sequential static images of the remote, real world exercise route.

With the control signals generated from the topographical data and the images of the remote, real world exercise route, remote communication system 14 generates exercise programming for treadmill 12a as described above. Remote communication system 14 then communicates the exercise programming to treadmill 12a as shown in FIG. 17. In some embodiments, remote communication system 14 can communicate the exercise programming directly to treadmill 12a, as shown in FIG. 17. For example, when treadmill 12 is adapted to communicate directly with network 18, remote communication system 14 can send the exercise programming directly to treadmill 12a via network 18.

In other embodiments, remote communication system 14 communicates the exercise programming to treadmill 12a via personal computer 16. For instance, when personal computer 16 is adapted to communicate with network 18 and treadmill 12a, via a hardwire or wireless connection, remote communication system 14 can send the exercise programming to personal computer 16, which can in turn send the exercise programming to treadmill 12a. Personal computer 16 can send the exercise programming to treadmill 12a through a variety of means. For example, personal computer 16 can communicate with treadmill 12a via a hardwire or wireless connection as described herein. Alternatively, personal computer 16 may be adapted to store the exercise programming on a portable memory device, which can be selectively associated with treadmill 12a. By way of non-limiting example, personal computer 16 can be adapted to receive and store the exercise programming on a portable memory device, such as an SD card, a DataFlash card, a MultiMedia Card (MMC), CompactFlash card, a removable NAND-type flash memory (e.g. SmartMedia, Sony Memory Stick), a one-time-programmable memory cards (OTP), XD cards, and the like. The portable memory device can then be removed from personal computer 16 and inserted or otherwise associated with treadmill 12a.

Once the exercise programming has been delivered to treadmill 12a via any suitable means, such as those described herein, treadmill 12a can run/execute the exercise programming by processing the control signals, the display programming, and/or the audio programming. As treadmill 12a runs the exercise programming, treadmill 12a simulates the remote, real world exercise route. In particular, the control signals of the exercise programming cause treadmill 12a to adjust one or more operating parameters, such as the incline or tilt of treadbase 26, to replicate the terrain of the remote, real world exercise route. In addition, treadmill 12 a displays, via display 152, the plurality of sequential static images of the remote, real world exercise route. As noted herein, the generation of the exercise programming includes the synchronization of the control signals and the plurality of sequential static images. This synchronization allows the user to view the images of the remote, real world exercise route while treadmill 12a simulates the terrain of the remote, real world exercise route that is associated with those images. In other words, synchronizing the control signals and the plurality of sequential static images allows a user of treadmill 12a to experience the terrain of the remote, real world exercise route while simultaneously viewing images of the portion of the remote, real world exercise route that is being simulated at that time.

Thus, in one embodiment, i) topographical data retrieved from a third party 20, such as the GTOPO 30 databases, is used to generate control signals that adjust operational parameters of treadmill 12a to simulate real world terrain; and ii) image data retrieved from another third party 20, such as the GOOGLE STREET VIEW database, is synchronized with the control signals and displayed on video output device 152. In this embodiment, the user can experience the topographical changes of the real world terrain as represented by the topographical data retrieved from the GTOPO 30 database, for example, while simultaneously viewing the corresponding images for the same terrain that have been retrieved from the GOOGLE STREET VIEW database, for example.

As noted above, treadmill 12a can monitor the actual operating parameters of treadmill 12a, such as the incline and tilt of treadbase 26 and the speed of belt 42. The actual operating parameters of treadmill 12a and the exercise programming can be correlated so that the control signals, display programming, and audio programming are updated or changed at the appropriate times. For instance, the exercise programming may include control signals that incline treadbase 26 to a 5% grade for ¼ mile and then decline treadbase to a 2% grade for 1 mile. The speed of belt 42 will affect the amount of time that each of the controls signals is active. If belt 42 were moving at 5 miles per hour (mph), for example, the user would traverse the ¼ mile segment in 3 minute and the 1 mile segment in 12 minutes. If belt 42 were moving at 2.5 mph, however, it would take the user 6 minutes to traverse the ¼ mile segment and 24 minutes to traverse the 1 mile segment. Thus, correlating or synchronizing the actual operating parameters of treadmill 12a with the exercise programming allows treadmill 12a to be controlled in such a way as to realistically simulate the real world environment. The correlation or synchronization of the exercise programming and the actual operating parameters can be performed by treadmill controller 50, control panel 22, personal computer 16, communication system 14, or a combination thereof.

As mentioned above, control panel 22 may include manual override button 142. Manual override button 142 enables a user to override a control signal generated by communication system 18, personal computer 16, or treadmill 12a. For example, if the exercise program accessed through communication system 14 is too difficult for the user, the user may activate manual override button 142, thereby interrupting or decreasing the difficulty level of the program delivered to treadmill 12a by communication system 14. Furthermore, in the event that the exercise program is too easy, the user may increase the difficulty level of the exercise device. Consequently, manual override button 142 provides the user with a safety switch during operation of treadmill 12a. In an alternate configuration of treadmill 12a, the functionality of manual override button 142 is activated upon manual activation of one of the other input devices, such as but not limited to, time controls 126, distance controls 128, speed controls 130, incline controls 132, stop/pause button 136, and the like.

Similar to the operation of manual override button 142, scaling control 144 enables a user to vary the operating parameters of treadmill 12a during an exercise program run by treadmill 12a. A user may activate scaling control 144 and vary the intensity of an exercise program. The scaling control 144, therefore, enables a user to select a value representative of the proportional change to be made to the control signal received by the communicating mechanism of treadmill 12a from communication system 14. For example, if an exercise program requires a maximum speed of 6 mph with a maximum incline of 15 degrees for a period of 30 minutes, an individual may activate scaling control 144 to require only 66% intensity of the exercise program; stated otherwise, reduce the intensity by one third. Therefore, the exercise program is varied to a maximum speed of 4 mph, with a maximum incline of 10 degrees, for a period of 20 minutes. Optionally, scaling control 144 may enable the user to set maximum values for each operating parameter of treadmill 12a. In another configuration, scaling control 144 may enable the user to scale only one operating parameter of treadmill 12a while leaving other parameters unchanged. Hence, the user may vary the exercise program to their particular abilities, while obtaining the beneficial effects of exercising.

In addition to the output devices described above, the present invention may include various other output devices to provide information and data to the user of treadmill 12a. In one embodiment of treadmill 12a, control panel 22 includes one or more operating parameter displays. The one or more operating parameter displays give a visual display of some of the more important exercise device operating parameters, such as, but not limited to, speed, incline, distance traveled, calories used, elevation climbed, wheel resistance, and the like. The one or more operating parameter displays may use a numerical display, a graphical display, combinations thereof, or such other displays known to one skilled in that art. For example, the operating parameter display may be incorporated within video output device 152.

According to yet another aspect of the present invention, the exercise device is capable of being controlled by signals from the communication system and/or physical controls integrated onto the exercise device. The physically integrated controls and the controls from the communication system may be passed through a buffer that controls the exercise device. In this way, in the event that connectivity to the communication system is lost, a user of the exercise device would still be capable of controlling the exercise device.

As used in this specification and the appended claims, the phrases "communicating with," and "in communication with" and similar phrases shall mean any type of applicable communication known to one skilled in the art in light of the disclosure herein, such as electrical communication, optical communication, physical communication, magnetic communication, software communication, hardware communication, data communication, and the like.

An exercise system according to one embodiment of the present invention is configured to simulate a real world exercise route. The exercise system of the present embodiment comprises an exercise device including a movable element for movement in performance of exercise by a user and at least one actuator for controlling one or more operating parameters of the exercise device. The exercise device is adapted to receive exercising programming and use the exercise programming to substantially simulate one or more aspects of the real world exercise route. The exercise programming includes one or more control signals representative of changes to be made to the one or more operating parameters to substantially simulate the real world exercise route. The exercise system also includes a remote communication system adapted to use data relating to the real world exercise route to generate the exercise programming. The data is stored external to the remote communication system. The system also includes a network adapted to facilitate communication of the exercise programming from the remote communication system to the exercise device.

According to the present embodiment, the data used to generate the exercise programming comprises map data, topographical data, video or image data, or a combination thereof. The communication system is adapted to communicate with at least one third party to obtain the data used to generate the exercise programming. The at least one third party comprises a database or website. The exercise device of the exercise system is adapted to communicate with the network either directly or through a separate computer. The exercise device is selected from the group consisting of a treadmill, an exercise cycle, a climber, a hiker, an elliptical, and a stepper.

The exercise programming includes display programming including images of the real world exercise route. Furthermore, the control signals are adapted to control the one or more operating parameters to substantially simulate topographical characteristics of the real world exercise route. The control signals control the one or more operating parameters while the user views the images provided by the display programming on an exercise device display.

In another embodiment of the present invention, an exercise system is configured to simulate a real world exercise route and comprises an exercise device comprising a movable element for movement in performance of exercise by a user. The exercise device has one or more operating parameters that are controlled by exercise programming. The exercise system also includes a remote communication system adapted to communicate with a user of the exercise device to enable the user to select a starting point and an ending point for the real world exercise route of user defined exercise programming and generate the user defined exercise programming that includes one or more control signals representative of changes to be made to the one or more operating parameters to substantially simulate topographical characteristics of the real world exercise route, and display programming including images of the real world exercise route. The remote communication system generates the exercise programming from data stored external to the remote communication system. Additionally, the exercise system includes a network in communication with the exercise device and the remote communication system, the network being configured to communicate the exercise programming from the remote communication system to the exercise device.

In the present embodiment, the exercise device comprises a treadmill having a base frame, a treadbase mounted on the base frame, and an endless belt trained around the treadbase to enable the user to ambulate thereon. The treadbase is pivotally mounted on the base frame so that the treadbase can be selectively inclined or declined to simulate for the user the experience of ambulating up and down hills of the real world exercise route. Additionally, the treadbase is pivotally mounted on the base frame so that the treadbase can be selectively tilted from one side to the other side to substantially simulate for the user the experience of ambulating on an uneven surface of the real world exercise route.

According to the present embodiment, the one or more control signals control the operating parameters of the exercise device while the display programming is presented to the user on an exercise device display. Also, the data stored external to the remote communication system comprises data stored by at least one third party.

In a further embodiment of the present invention, an exercise system configured to simulate a remote, real world exercise route comprises an exercise device having a movable element for movement in performance of exercise by a user. The exercise device is receptive to control signals that adjust one or more operating parameters associated with the movable element to substantially simulate topographical characteristics of the remote, real world exercise route, while simultaneously presenting images of the remote, real world exercise route on an exercise device display. The exercise system also includes a remote communication system that generates exercise programming and communicates the exercise programming to the exercise device. The remote communication system uses data relating to the appearance and topographical characteristics of the remote, real world exercise route to generate the exercise programming. The exercise programming includes i) one or more control signals that are adapted to cause a change in the one or more operating parameters to substantially simulate the topographical characteristics of the remote, real world exercise route, and ii) display programming including the images of the remote, real world exercise route presented on the exercise device display. Moreover, the exercise system includes at least one database external to the remote communication system, the at least one database storing the data used by the remote communication system to generate the exercise programming.

In the present embodiment, the exercise device comprises an exercise cycle that includes: a support base adapted to rest upon a support surface; an upright support structure mounted to the support base, the upright support structure having a seat, a handle bar assembly, and a control panel; a pedal assembly adapted to be engaged and rotated by the user's feet, the pedal assembly being coupled to the upright support structure; and a resistance assembly adapted to provide resistance to the rotation of the pedal assembly, the resistance assembly being coupled to the upright support structure, the resistance assembly being controlled by the one or more control signals of the exercise programming.

The upright support structure is pivotally mounted to the support base, the upright support structure being selectively tilted forward or backward to substantially simulate for the user the experience of riding a bicycle up or down a hill. The resistance provided by the resistance assembly can be associated with the tilt of the upright support structure to substantially simulate for the user the experience of riding a bicycle up or down a hill on the remote, real world exercise route. The exercise programming is adapted to adjust the tilt of upright support structure and the resistance provided by the resistance assembly based upon the topographical characteristics of the remote, real world exercise route and the user's weight.

Yet a further embodiment of the present invention relates to an exercise system configured to simulate a remote, real world exercise route. The exercise system includes a network and an exercise device in communication with the network. The exercise device is receptive to exercise programming that is adapted to control one or more selectively adjustable operating parameters of the exercise device to substantially simulate the remote, real world exercise route. The system also includes at least one external database in communication with the network, the at least one database storing data relating to one or more characteristics of the remote, real world exercise route, and a remote communication system adapted to generate the exercise programming and communicate the exercise programming to the exercise device. The remote communication system is adapted to allow a user of the exercise device to define the remote, real world exercise route. The remote communication system is also adapted to communicate with the at least one database via the network to retrieve the data relating to the one or more characteristics of the remote, real world exercise route. Further, the remote communication system is adapted to use the user defined remote, real world exercise route and the data retrieved from the at least one database to generate the exercise programming, wherein the at least one database is external to the remote communication system.

In the present embodiment, the data stored by the at least one database comprises map data, topographical data, image data, or a combination thereof. The remote communication system is adapted to generate one or more control signals for incorporation in the exercise programming, the one or more control signals being generated based on the topographical data retrieved from the at least one database. The one or more control signals are representative of changes to be made to the one or more selectively adjustable operating parameters of the exercise device to substantially simulate the remote, real world exercise route. Furthermore, the remote communication system is adapted to generate display programming for incorporation in the exercise programming, the display programming including the image data retrieved from the at least one database. Additionally, the at least one database is external to and remote from the remote communication system.

In another embodiment of an exercise system configured to simulate a remote, real world exercise route, the exercise system comprises an exercise device and a remote communication system. The exercise device is adapted to substantially simulate the remote, real world exercise route in response to exercise programming, wherein the exercise device comprises a user interface that enables a user to define the remote, real world exercise route by selecting one or more parameters of the remote, real world exercise route. The one or more user selectable parameters of the remote, real world exercise route include a starting point, an ending point, a total distance, a total elevation change, or a combination thereof. The remote communication system in is communication with the exercise device. The remote communication system is adapted to receive the one or more user defined parameters of the remote, real world exercise route and communicate with at least two third parties to retrieve data stored by the at least two third parties relating to the remote, real world exercise route. The remote communication system is also adapted to use the data retrieved from the at least two third parties to generate the exercise programming that includes control signals for controlling the operation of the exercise device and display programming synchronized with the control signals.

The remote communication system communicates with the at least two third parties via a network. The at least two third parties comprise at least two databases external to and remote from the remote communication system. The at least two databases are accessible via one or more websites. The remote communication system uses topographical data stored by one of the at least two third parties to generate the control signals that are configured to adjust one or more operating parameters of the exercise device. Similarly, the remote communication system uses image data stored by another one of the at least two third parties to generate the display programming. The image data comprises a plurality of sequential static images of the remote, real world exercise route.

The synchronization of the display programming and the control signals provides the user with the ability to view images of the real world exercise route while substantially experiencing, by way of the one or more changing operating parameters, the topographical characteristics of the real world environment viewed in the images of the display programming. The remote communication system synchronizes the control signals and the display programming so that there is a temporal relationship between changes in the control signals and the display programming.

A first third party of the at least two third parties of the present embodiment stores topographical data relating to the remote, real world exercise route, a second third party of the at least two third parties stores a plurality of sequential static images of the remote, real world exercise route, and the remote communication system synchronizes the plurality of sequential static images with control signals representative of the topographical data. Alternatively, a first third party of the at least two third parties stores topographical data relating to the remote, real world exercise route, a second third party of the at least two third parties stores one or more video images of the remote, real world exercise route, and the remote communication system synchronizes the one or more video images with control signals representative of the topographical data.

Another embodiment of the present invention relates to a method for generating exercise programming for substantially simulating a remote, real world exercise route on an exercise device. The method can be practiced in an exercise system having a remote communication system adapted to communicate with the exercise device and at least two third party databases. The method includes the steps of: receiving one or more parameters for defining the remote, real world exercise route; retrieving a first type of data relating to the remote, real world exercise route from a first third party database of the at least two third party databases; retrieving a second type of data relating to the remote, real world exercise route from a second third party database the at least two third party databases; generating one or more control signals using the first type of data retrieved from the first third party database, the control signals being adapted to cause the exercise device to substantially simulate topographical characteristics of the remote, real world exercise route; generating display programming using the second type of data retrieved from the second third party database, the display programming including images of the remote, real world exercise route; and synchronizing the one or more control signals and the display programming.

The method can also include communicating the one or more remote, real world exercise route defining parameters to the at least two third party databases, or communicating the one or more remote, real world exercise route defining parameters from the exercise device to the remote communication system. The method can also include generating a remote, real world exercise route based on the one or more remote, real world exercise route defining parameters. The step of synchronizing the one or more control signals and the display programming comprises temporally relating the one or more control signals and the display programming. The step of synchronizing the one or more control signals and the display programming correlates changes in the one or more control signals to changes in the display programming.

Each of the first and second third party databases comprises one or more databases accessible by the remote communication system via a website. The first type of data comprises topographical data, and the second type of data comprises image data and the second type of data used to generate the display programming includes image data. The image data comprises one or more static images and/or one or more video images.

In still yet another embodiment, an exercise system configured to substantially simulate a remote, real world exercise route comprises a network, an exercise device, a plurality of third parties, and a remote communication system. The exercise device is in communication with the network, the exercise device being receptive to exercise programming that is adapted to control one or more selectively adjustable operating parameters of the exercise device to substantially simulate the remote, real world exercise route. The plurality of third parties is in communication with the network, the plurality of third parties storing data relating to one or more characteristics of the remote, real world exercise route. The plurality of third parties comprises one or more databases that store topographical data relating to the remote, real world exercise route, and one or more other databases that store image data relating to the remote, real world exercise route. The remote communication system is external to and remote from the plurality of third parties, the remote communication system is adapted to allow a user of the exercise device to define the remote, real world exercise route. The remote communication system is adapted to communicate with the plurality of third parties via the network to retrieve the data relating to the one or more characteristics of the remote, real world exercise route. The remote communication system is also adapted to use the data retrieved from the plurality of databases to generate the exercise programming. Generating the exercise programming includes (i) using the image data to generate display programming; (ii) using the topographical data to generate control signals; and (iii) synchronizing the display programming with the control signals, the remote communication system being adapted to communicate the exercise programming to the exercise device.

The remote communication system generates the control signals using the topographical data. The control signals control the one or more selectively adjustable operating parameters of the exercise device to substantially simulate the terrain of the remote, real world exercise route. The image data comprises a plurality of sequential static images of the remote, real world exercise route and the exercise device comprises a display adapted to display the plurality of sequential static images.

Synchronization of the control signals and the plurality of sequential static images enables the user of the exercise device to substantially experience the terrain of the remote, real world exercise route on the exercise device while simultaneously viewing images of the remote, real world exercise route associated with the simulated terrain. The image data comprises video images of the remote, real world exercise route and the exercise device comprises a display adapted to display the video images of the remote, real world exercise route. The plurality of third parties are external to and remote from the remote communication system.

Certain features relating to embodiments of the present invention are further disclosed in: U.S. patent application Ser. No. 11/849,068, entitled "Exercise Device with On Board Personal Trainer," filed Aug. 31, 2007, U.S. Patent Publication No. 2008-0051256, which is incorporated herein in its entirety by reference; U.S. patent application Ser. No. 11/429,725, entitled "Systems and Methods for Enabling Two-Way Communication Between One or More Exercise Devices and Computer Devices and for Enabling Users of the One or More Exercise Devices to Competitively Exercise," filed May 8, 2006, U.S. Patent Publication No. 2006-0205569, which is incorporated herein in its entirety by reference; U.S. patent application Ser. No. 09/641,627, entitled "System for interaction with Exercise Device," filed Aug. 18, 2000, now U.S. Pat. No. 7,166,062, which is hereby incorporated herein by reference in its entirety; U.S. patent application Ser. No. 09/496,560, entitled "System and Method for Selective Adjustment of Exercise Apparatus," filed on Feb. 2, 2000, now U.S. Pat. No. 6,447,424, which is incorporated herein in its entirety by reference; and U.S. patent application Ser. No. 09/349,608, entitled "Systems and Methods for Providing an Improved Exercise Device with Motivational Programming," filed on Jul. 8, 1999, now U.S. Pat. No. 6,312,363, which is hereby incorporated herein by reference in its entirety. Each of the foregoing patents and patent applications is hereby incorporated herein in its entirety by reference.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An exercise system that simulates a real world exercise route, the exercise system comprising:
an exercise device comprising a movable element that is movable in performance of exercise by a user, the exercise device having one or more operating parameters that are controllable by user defined exercise programming, the exercise device comprising a support base that rests upon a support surface, an upright support structure mounted on the support base, and a resistance assembly that provides resistance to movement of the movable element;
a display that presents display programming to the user during performance of exercise;
a remote communication system that communicates with a user of the exercise device to enable the user to select a starting point and an ending point for a real world exercise route of the user defined exercise programming and generates the user defined exercise programming, the user defined exercise programming including (i) one or more control signals representative of changes to be made to the one or more operating parameters to substantially simulate topographical characteristics of the real world exercise route, and (ii) the display programming that includes images of the real world exercise route, wherein the one or more control signals control the operating parameters of the exercise device while the display programming is presented to the user on the display, and wherein the remote communication system generates the exercise programming from data stored external to the remote communication system;
wherein the exercise programming is adapted to adjust a tilt of the upright support structure and the resistance provided by the resistance assembly based upon the topographical characteristics of the real world exercise route and the user's weight such that the remote communication system changes the tilt based on the topographical characteristics and the user's weight at the same time the display programming of the simulated real world exercise route depicts a change in terrain.

2. An exercise system as recited in claim 1, further comprising a network that facilitates communication of the user defined exercise programming from the remote communication system to at least one of the exercise device and the display.

3. An exercise system as recited in claim 1, wherein the exercise device comprises an exercise cycle, wherein the upright support structure includes a seat, a handle bar assembly, and a pedal assembly that is rotatable by the user's feet; and the resistance assembly provides resistance to the rotation of the pedal assembly.

4. An exercise system as recited in claim 3, wherein the upright support structure is pivotally mounted on the support base, the upright support structure being selectively tilted forward or backward to substantially simulate for the user the experience of riding a bicycle up or down a hill.

5. An exercise system as recited in claim 4, wherein the resistance provided by the resistance assembly can be associated with the tilt of the upright support structure to substantially simulate for the user the experience of riding a bicycle up or down a hill on the remote, real world exercise route.

6. An exercise system as recited in claim 1, wherein the data stored external to the remote communication system comprises data stored by at least one third party.

7. An exercise system as recited in claim 1, wherein the display is separate from the exercise device.

8. An exercise system as recited in claim 1, wherein the display is incorporated into the exercise device.

9. An exercise system as recited in claim 1, wherein the remote communication system communicates with the user of the exercise device via the exercise device or a separate computer to enable the user to select the starting point and the ending point for the real world exercise route.

10. An exercise system that simulates a real world exercise route, the exercise system comprising:
an exercise device comprising a movable element that is movable during performance of exercise by a user, at least one actuator that controls one or more operating parameters of the exercise device, an upright support structure, and a resistance assembly operable to apply resistance to movement of the movable element, the exercise device being receptive to control signals representative of changes to be made to the one or more operating parameters to substantially simulate topographical characteristics of the real world exercise route, the changes to the one or more operating parameters corresponding to one or more aspects of the real world exercise route;
a remote communication system that communicates with a user of the exercise device to enable the user to select a starting point and an ending point for the real world exercise route, wherein the remote communication system uses data relating to the one or more aspects of the real world exercise route to generate exercise programming, the exercise programming including one or more control signals and display programming, the display programming including images of the real world exercise route synchronized with the one or more control signals; and a local computer in communication with the remote communication system and the exercise device, wherein the local computer receives the exercise programming from the remote communication system, wherein the local computer communicates the one or more control signals to the exercise device, and wherein the local computer comprises a display that presents the display programming to the user during performance of exercise;

wherein the exercise programming is adapted to adjust a tilt of the upright support structure and the resistance provided by the resistance assembly based upon the topographical characteristics of the real world exercise route and the user's weight such that the remote communication system changes the tilt based on the topographical characteristics and the user's weight at the same time the display programming of the simulated real world exercise route depicts a change in terrain.

11. An exercise system as recited in claim 10, wherein the local computer communicates with the remote communication system via a network.

12. An exercise system as recited in claim 10, wherein the control signals control the one or more operating parameters while the user views the images provided by the display programming on the display.

13. An exercise system as recited in claim 10, wherein the data used to generate the exercise programming comprises map data, topographical data, video or image data, or a combination thereof relating to the one or more aspects of the real world exercise route.

14. An exercise system as recited in claim 10, wherein the exercise device is selected from the group consisting of a treadmill, an exercise cycle, a climber, a hiker, an elliptical, and a stepper.

15. An exercise system as recited in claim 10, wherein the remote communication system communicates with at least one third party to obtain the data used to generate the exercise programming.

16. An exercise system as recited in claim 15, wherein the at least one third party comprise a database or website.

17. In a computerized exercise environment including an exercise device, a remote communication system that generates exercise programming, and a local computer, a method of controlling the exercise device, the exercise device comprising a movable element that is movable during performance of exercise by a user, an upright support structure, and a resistance assembly operable to apply resistance to movement of the movable element, the method comprising:

receiving one or more user inputs at the remote communication system, the one or more user inputs defining at least a starting point and an ending point for a real world exercise route, wherein the remote communication system generates and synchronizes one or more control signals with one or more images of the real world exercise route to generate exercise programming, the one or more control signals being adapted to control one or more operating parameters, which include at least a tilt of the upright support structure and the resistance provided by the resistance assembly of the exercise device based upon topographical characteristics of the real world exercise route and the user's weight such that the remote communication system changes the tilt based on the topographical characteristics and the user's weight at the same time the display programming of the simulated real world exercise route depicts a change in terrain;

communicating the exercise programming from the remote communication system to the local computer;

communicating the one or more control signals from the local computer to the exercise device to control the one or more operating parameters of the exercise device; and displaying the one or more images of the real world exercise route as the one or more control signals control the one or more operating parameters of the exercise device.

18. A method as recited in claim 17, wherein the one or more images of the real world exercise route are displayed on a display associated with the local computer or the exercise device.

19. A method as recited in claim 17, wherein the one or more control signals are communicated from the local computer to the exercise device via a wireless connection.

* * * * *